(12) United States Patent
Zhao et al.

(10) Patent No.: US 11,358,970 B2
(45) Date of Patent: Jun. 14, 2022

(54) ARTEMISININ-DERIVED TRIMERS AND TETRAMERS AND THEIR USE THEREOF

(71) Applicants: Ming Zhao, Darien, IL (US); Li-Ming Zhou, Darien, IL (US)

(72) Inventors: Ming Zhao, Darien, IL (US); Li-Ming Zhou, Darien, IL (US)

(*) Notice: Subject to any disclaimer, the term of this patent is extended or adjusted under 35 U.S.C. 154(b) by 0 days.

(21) Appl. No.: 16/755,562

(22) PCT Filed: Nov. 21, 2018

(86) PCT No.: PCT/US2018/062356
§ 371 (c)(1),
(2) Date: Apr. 15, 2020

(87) PCT Pub. No.: WO2019/104247
PCT Pub. Date: May 31, 2019

(65) Prior Publication Data
US 2021/0079011 A1     Mar. 18, 2021

Related U.S. Application Data

(60) Provisional application No. 62/588,921, filed on Nov. 21, 2017.

(51) Int. Cl.
*C07D 493/18*     (2006.01)
*A61P 35/02*      (2006.01)
*A61P 35/00*      (2006.01)

(52) U.S. Cl.
CPC .......... *C07D 493/18* (2013.01); *A61P 35/00* (2018.01); *A61P 35/02* (2018.01)

(58) Field of Classification Search
CPC ......... C07D 493/18; A61P 35/02; A61P 35/00
USPC ........................................................ 514/450
See application file for complete search history.

(56) References Cited

U.S. PATENT DOCUMENTS

| | | | |
|---|---|---|---|
| 8,883,765 | B2 | 11/2014 | Arav-Boger et al. |
| 9,603,831 | B2 | 3/2017 | Thiemermann |
| 2006/0074251 | A1 | 4/2006 | Jung |
| 2016/0228457 | A1 | 8/2016 | Chigaev et al. |

FOREIGN PATENT DOCUMENTS

| | | | | |
|---|---|---|---|---|
| CN | 102153564 | B | 7/2013 | |
| CN | 105078964 | B | 11/2015 | |
| CN | 109467565 | A | 8/2018 | |
| WO | WO2010110747 | A1 | 3/2010 | |
| WO | WO2012168450 | A1 | 12/2012 | |
| WO | WO-2013177978 | A1 * | 12/2013 | ............ A61P 33/06 |
| WO | WO2014090306 | A1 | 6/2014 | |

OTHER PUBLICATIONS

Desmond Slade et al. Antiprotozal, anticancer and antimicrobial activities of Hydroartemisinin acetal dimers and monomers. (Year: 2009).*
Bhatia et al, A review on Bioisosterism : A rational approach for Drug Design and Molecular Modification. (Year: 2011).*
Chaturvedi, Chem Soc Rev, 210, DOI: 10.1039/b816679, 1-40. (Year: 2010).*
Efferth et al. "The Anti-malarial Artesunate is also Active Against Cancer", Int. J. Oncol. Apr. 2001, 18(4):767-773.
Chen et al. "Inhibition of Human Cancer Cell Line Growth and Human Umbilical Vein Endothelial Cell Angiogenesis by Artemisinin Derivatives in vitro", Pharmacol. Res. Sep. 2003, 48(3):231-236.
Sun et al. "Effect of Artesunate on Rat Corneal Neovascularization" J. Ocular Trauma Occup. Eye Dis. Mar. 25, 2007, 29(3)172-175 (English abstract only).
Sun et al. "Effect of Artemisinin on Ischemia/Reperfusion Injury of Isolated Rat Myocardium", China J. Chinese Materia Medica, Aug. 2007, 32(15):1547-1511 (with English abstract).
Li et al. "Antimalarial Artesunate Protects Sepsis Model Mice Against Heat-Killed *Escherichia coli* Challenge by Decreasing TLR4, TLR9 mRNA Expressions and Transcription Factor NF-Kb Activation", Int. Immunopharmacol. Mar. 2008, 8(3):379-389.
He et al. "An Artemisinin-Derived Dimer Has Highly Potent Anti-Cytomegalovirus (CMV) and Anti-Cancer Activities", PLoS One. 2011, 6(8):e24334.
Wang et al. "Effect of Artesunate on Endotoxin-Induced Uveitis in Rats", Invest. Ophthalmol. Vis. Sci. Feb. 16, 2011, 52(2):916-919.
Cheng et al. "The Artemisinin Derivative Artesunate inhibits Corneal Neovascularization by Inducing ROS-Dependent Apoptosis In Vascular Endothelial Cells", Invest. Ophthalmol. Vis. Sci. May 15, 2013, 54(5):3400-3409.
Ho et al. "Artemisinins: Pharmacological Actions Beyond Aantimalarial", Pharmacol. Ther. Apr. 2014, 142(1):126-139.
Lai et al. "Artesunate Alleviates Hepatic Fibrosis Induced by Multiple Pathogenic Factors and Inflammation Through the Inhibition of LPS/TLR4/NF-κB Signaling Pathway in Arats", Eur. J. Pharmacol. Oct. 15, 2015, 765:234-241.
Reiter et al. "Highly Potent Artemisinin-Derived Dimers and Trimers: Synthesis and Evaluation of Their Antimalarial, Antileukemia and Antiviral Activities", Bioorg. Med. Chem. Sep. 1, 2015, 23(17):5452-5458.
Fox et al. "Artemisinin-Derived Dimer ART-838 Potently Inhibited Human Acute Leukemias, Persisted In Vivo, and Synergized With Antileukemic Drugs", Oncotarget. Feb. 9, 2016, 7(6):7268-7279.
Frchlich et al. "Artemisinin-Derived Dimers: Potent Antimalarial and Anticancer Agents", J Med Chem. Aug. 25, 2016, 59(16):7360-788.
Zong et al., "Small Molecular-Sized Artesunate Attenuates Ocular Neovascularization via VEGFR2, PKCα, and PDGFR Targets", Sci. Rep. Aug. 2, 2016, 6:30843.
Subedi et al. "High-Throughput Screening Identifies Artesunate as Selective Inhibitor of Cancer Stemness: Involvement of Mitochondrial Metabolism", Biochem. Biophys. Res. Commun. Sep. 2, 2016, 477(4):737-742.

(Continued)

*Primary Examiner* — D Margaret M Seaman

(57) ABSTRACT

The present disclosure provides compositions comprising artemisinin-derived trimers and tetramers; methods of preparing these compositions; and methods for their use as medicaments.

19 Claims, No Drawings

(56) References Cited

OTHER PUBLICATIONS

Reid et al. "Discovery of Novel Small Molecule Inhibitors of Cardiac Hypertrophyusing High Throughput, High Content Imaging", J. Mol. Cell Cardiol. Aug. 2016, 97:106-113.

Khan et al. "The Antimalarial Drug Artesunate Attenuates Cardiac Injury in a Rodent Model of Myocardial Infarction", Shock. Jun. 2018, 49(6):675-681.

Frohlich et al. "Synthesis of Artemisinin-Derived Dimers, Trimers and Dendrimers: Investigation of Their Antimalarial and Antiviral Activities Including Putative Mechanisms of Action", Chem. Eur. J. Mar. 23, 2018, 24(32):8103-8113.

Pearce, A. N. et al. (Sep. 2017). "Synthesis and Antimalarial Evaluation of Artesunate-polyamine and Trioxolane-polyamine Conjugates", European Journal of Medicinal Chemistry, 140:595-603.

* cited by examiner

ARTEMISININ-DERIVED TRIMERS AND TETRAMERS AND THEIR USE THEREOF

CROSS-REFERENCE TO RELATED APPLICATION AND INCORPORATION BY REFERENCE

This application is a U.S National Phase filing of International Application Serial No. PCT/US2018/062356 filed 21 Nov. 2018 and claims the benefit of U.S. Provisional Application No. 62/588,921, filed Nov. 21, 2017, the entireties of which are incorporated herein by reference.

FIELD

The present disclosure relates to artemisinin-derived trimers and tetramers, methods of their preparation, and methods for their use as medicaments.

BACKGROUND

Artemisinin is an active antimalarial component isolated from herb *Artemisia annua* (qinghao) in 1972. Early investigation on structure-activity relationships of artemisinin has identified artesunate, dihydroartemisinin and artemether to be more active and less toxic than the parental drug artemisinin in the treatment of malarial infections. Up to date, these artemisinin derivatives have proven to be the most important antimalarial agents in artemisinin combination therapy (ACT). In particular, intravenous injection of artesunate has been recommended by the WHO as first line treatment of severe and cerebral malaria (World Health Organization, Guidelines for the treatment of malaria, Second edition 2010). Furthermore, numerous studies have shown that artemisinin and its derivatives (artemisinins) possess a wide variety of biological activities beyond antimalarial, including anticancer, antivirus, treating inflammatory and immune disorders, organ protection caused by hemorrhage-reperfusion and sepsis, anti-other parasite related infections (e.g. *Schistosoma japonicum* and toxoplasma), antifungals (reviewed by Ho et al, Pharmacol Ther, 2014, 142(1):126-139), and anti-ocular neovascularization.

Efferth et al. reported anticancer activity of artesunate against 55 cancer cell lines from the Departmental Therapeutics Program of the National Institutes of Health and cancer cell lines resistant to doxorubicin, vincristine, methotrexate and hydroxyurea (Int J Oncol, 2001, 18(4); 767-773). Yu et al. described the treatment of patients with systemic lupus erythematosus with artesunate (Chinese J Derm, 1997, 30(1); 51-52). Chen et al. described antiangiogenetic effects of artesunate and dihydroartemisinin on cancer cells and human umbilical vein endothelial cell angiogenesis (Pharmacol Res, 48(3):231-6).

Sun et al. described protective effects of artemisinin on ischemia/reperfusion injury of isolated rat myocardium (Zhongguo Zhong Yao Za Zhi, 2007, 32(15); 1547-51). Zhang et al. described the use of artesunate in combination with a chemotherapy regimen of vinorelbine and cisplatin for patients with advanced non-small cell lung cancers (Zhong Xi Yi Jie He Xue Bao, 2008, 6(2):134-138). Li et al. reported artesunate for use in the treatment of sepsis against heat-killed *E. coli* challenges in mice (Int Immunopharmacol, 2008, 8(3):379-389). Liu et al. described the use of artesunate for the treatment of patients with sepsis or organ damages caused by malarial infection (J Trop Med, 2009, 9(7): 755-756). WO2012168450 describes the use of artemisinin and its analogs for the treatment of organ injury caused by trauma hemorrhage and in stoke and burns injury. WO2014090306 describes the use of artesunate for the treatment of acute, chronic kidney injury, uremia and in surgery that results in ischemia-reperfusion (kidney transplantation, kidney and pancreas transplantation, coronary artery bypass graft).

Reid et al. described the ability of artesunate to block left ventricular hypotrophy and improve cardiac function in adult mice subjected to transverse aortic constriction (J Mol Cell Cardiol, 2016, 97:106-13).

WO 2010/0137246 relates to the use of artesunate for the treatment of asthma and respiratory distress syndrome. CN 20151513816 describes the use of artesunate for the treatment of idiopathic pulmonary fibrosis. Lai et al. described the use of artesunate to alleviate hepatic fibrosis induced by multiple pathogenic factors (Eur J Pharmacol, 2015, 765, 234-241).

Wang et al. described inhibitory effects of artesunate on endotoxin lipopolysaccharide-induced uveitis in rats (Invest Ophthalmol Vis Sci, 2011; 52:916-919). Subedi el al. described inhibitory effects of artesunate on cancer stemness in induced cancer stem-like cells (Biochem Biophys Res Commun, 2016 Sep. 2; 477(4):737-742). Khan et al. describe the use of artesunate and dihydroartemisinin for the treatment of myocardial infarction (Shock, 2018, 49(6):675-681).

Scheme 1

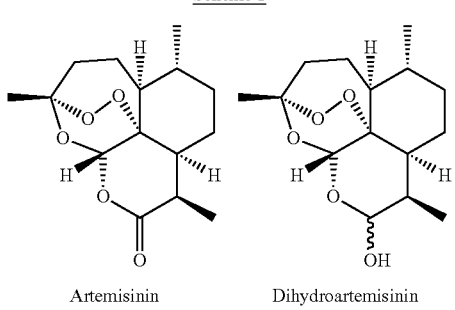

Artemisinin                Dihydroartemisinin

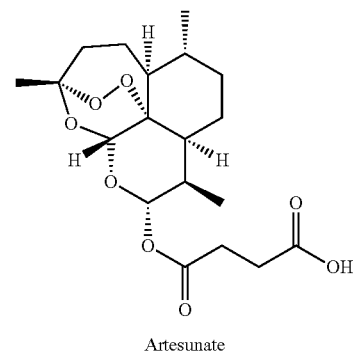

Artesunate

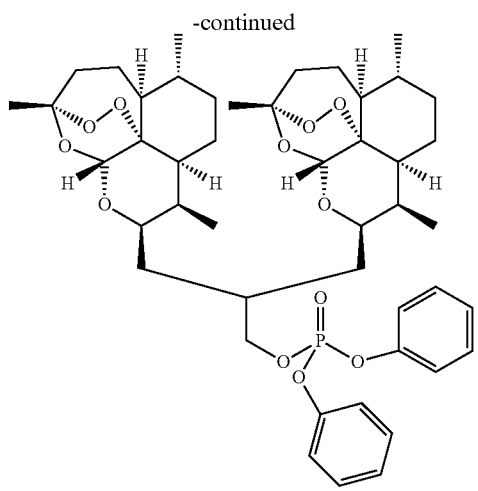

Art-838

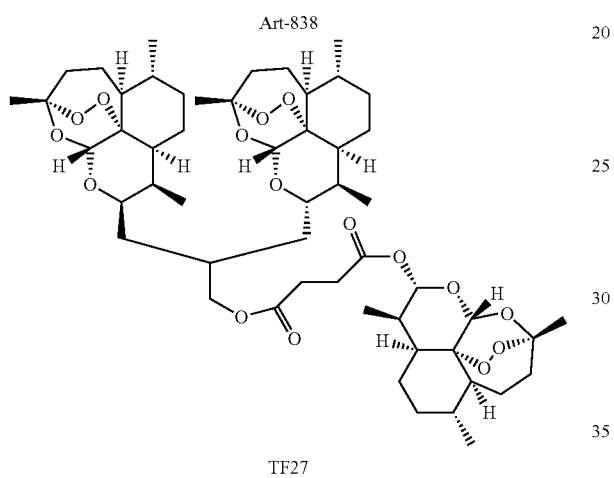

TF27

Sun et al. described inhibitory effects of artesunate on corneal neovascularization in rats with alkali-burned corneal (Chinese Journal of Ocular Trauma & Occupational Eye Disease, 2007, 29(3):172-174). Delivered by conjunctival injection or by eye drops, two independent research groups described artesunate attenuating corneal damage and inflammation in rabbits alkali-induced corneal (J South Med Univ, 2008, 28(12):2281-2283; Inv. Ophthmal Vis Sci, 2013, 3400-09). Zong at al. described artesunate as an inhibitor of ocular neovascularization and fluorescein leakage in rabbits and monkeys pretreated with intraocular injection of $VEFG_{185}$ and basicFGF (Sci Reports, 2016, 6:30843, 1-12).

The versatile biological activities of artemisinin and its derivatives, in particular artesunate, have led to design and synthesis of new artemisinin analogs to develop more efficacious molecules. In this regard, one proven strategy has been to couple two or three artemisinin or its analogs into one molecule via a linker. Frohlich et al. reviewed artemisinin-derived dimmers with potent antimalarial, antiviral and anticancer activities (J Med Chem, 2016, 59:7360-7388). Fox et al described that ART838 (Scheme 1), an artemisinin-derived diphenylphosphate dimer, exhibits 11 to 315 folds (average 88) more potent than artesunate in inhibiting 23 leukemia cell lines (Oncotarget, 2016, 7(6):7268-7279). He et al. described that ART838 is 165-fold more potent in inhibiting growth of cytomegalovirus than artesunate (PloS ONE, 2011, 6(8):e24334). Li et al described dimers of dihydroartemisinin coupled by a nitrogen-containing linker and their enhanced anticancer activity in reference to artesunate (CN 102153564). Reiter et al described trimer compound TF27 (Scheme 1) to exhibit increased in vitro activity against *Plasmodium falciparum* 3D7 strain, leukemia CCRF-CEM and multidrug-resistant subline CEM/ADR5000 cells, human cytomegalovirus (Bioorg Med Chem, 2015, 23(17):5452-5458). Frohlich et al described artemisinin-derived dimeric, trimeric and dendrimeric derivatives and their significantly enhanced activities against malaria parasite *Plasmodium falciparum* and human cytomegalovirus (Chem Eur J, 2018, 24, 1-12). All references described herein are incorporated by reference.

SUMMARY

The present disclosure provides novel artemisinin-derived trimers or tetramers, methods for their preparation, pharmaceutical compositions comprising these compounds, and methods for treating subjects afflicted with cancer, subjects infected with malaria or other parasite infections including, but not limited to, toxoplasma infection; subjects affected with virus; subjects afflicted with inflammation and autoimmune disorders and conditions; subjects afflicted with ocular neovascularization conditions; subjects afflicted with organ damages; subjects afflicted with sepsis and subjects afflicted with stroke and myocardial infarction, using these compounds and compositions.

In one aspect, the present disclosure relates to compounds of formula (I):

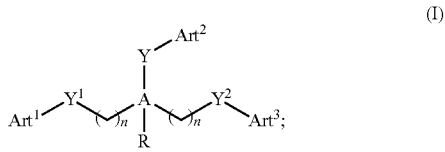

wherein:
n is an integer from 0 to 6;
$Art^1$, $Art^2$ and $Art^3$ are each independently selected from:

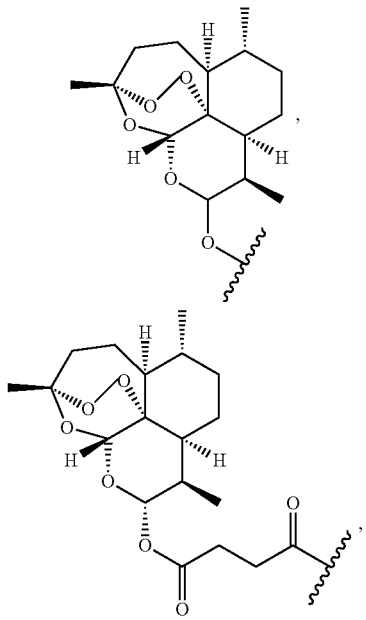

-continued

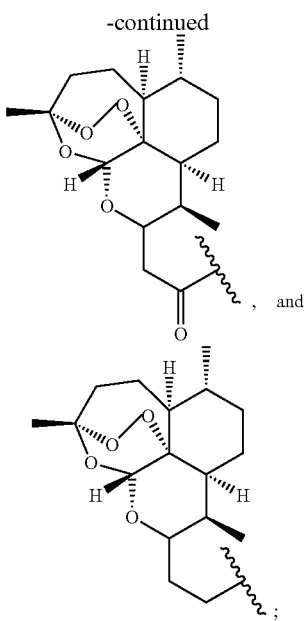
, and wherein A is selected from carbon, nitrogen, and

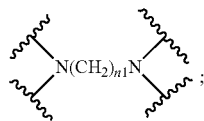
;

wherein n1 is an integer selected from 0 to 12;

Y, $Y^1$, and $Y^2$ are each independently selected from absent, O, NH, $NR^1$, $S(O)_m$, —$(CHR^1)_{n2}$—, —$(CHR^1)_{n2}O$—, —$(CHR^1)_{n2}N$—, —$(CHR^1)_{n2}C(=O)$—, —$(CHR^1)_{n2}C(=O)O$—, —$(CHR^1)_{n2}C(=O)NR^1$—, —$(CHR^1)_{n2}S(O)_m$, and —$(CHR^1)_{n2}C(=O)S$—; wherein n2 is an integer selected from 0 to 6; and m is an integer selected from 0 to 2; and R is selected from absent, hydrogen, —$OR^1$, —$C(O)R^1$, —$C(O)OR^1$, —$(CHR^2)_{n3}R^1$, —$(CHR^2)_{n3}OR^1$, —$NR^2R^1$, —$(CHR^2)_{n3}NR^2R^1$, —$NR^2C(O)R^1$, —$NR^2C(O)OR^1$, —$NR^2C(O)NHR^1$, —$(CHR^2)_{n3}OC(O)R^1$, —$(CHR^2)_{n3}C(O)OR^1$, —$N=BR^1$, and —$NHS(O)_mR^1$; wherein n3 is an integer selected from 0 to 8; and m is an integer selected from 0 to 2; and wherein B is selected from N and C; $R^1$ and $R^2$ are each independently selected from hydrogen, $Art^1$, $Art^2$, $Art^3$, $C_{1-10}$alkyl, $C_{1-6}$haloalkyl, $C_{1-6}$haloalkoxyl, $C_{2-6}$alkenyl, $C_{2-6}$alkynyl, $C_{1-6}$alkylene, $COOC_{1-6}$alkyl, $C_{1-6}$alkyleneCOOH, $C_{3-12}$cycloalkyl, 3-12 membered heterocyclyl, $C_{6-12}$aryl, and 5-12 membered heteroaryl;

wherein each $C_{1-6}$alkyl, $C_{2-6}$alkenyl, $C_2$-alkynyl, $C_{1-6}$alkyleneCOOC$_{1-6}$alkyl, $C_{1-6}$alkyleneCOOH, $C_{6-12}$aryl, 3-12 membered heterocyclyl, and 5-12 membered heteroaryl of $R^1$ and $R^2$ is independently optionally substituted with one to ten groups selected from halo, hydroxyl, amino, cyano, $C_{1-6}$alkyl, $C_{1-6}$haloalkyl, $C_{1-6}$alkoxyl, $C_{1-6}$haloalkyl, $C_{3-6}$cycloalkyl, and 3-6 membered heterocyclyl.

The compounds of the present disclosure can also exist in the form of enantimers, diastereomers, racemates, pharmaceutically acceptable salts, prodrugs, or solvates, namely in the form of associations with one or more molecules of water or a solvent.

In another aspect, the present disclosure provides a pharmaceutical composition comprising a therapeutically effective amount of a compound described herein and a pharmaceutically acceptable carrier or excipient.

In another aspect, the present disclosure provides a method for treatment.

Representative compounds from the present disclosure exhibit significantly enhanced activities to inhibit the proliferation of Hela, MOLT4, A549 and HepG2 cell lines. The products according to the present disclosure may therefore be used for the preparation of medicaments.

DETAILED DESCRIPTION

Definitions

Any terms in the present application, unless specifically defined, will take the ordinary meanings as understood by a person of ordinary skill in the art.

As used herein, the singular forms "a", "an", and "the" include plural reference unless the context clearly dictates otherwise.

Unless stated otherwise, all aryl, cycloalkyl, heteroaryl, and heterocyclyl groups of the present disclosure may be substituted as described in each of their respective definitions. For example, the aryl part of an arylalkyl group, such as benzyl, may be substituted as described in the definition of the term "aryl."

A squiggly line on a chemical group as shown below, for example,

indicates a point of attachment, i.e., it shows the broken bond by which the group is connected to another described group.

The prefix "$C_{u-v}$" indicates that the following group has from u to v carbon atoms. For example, "$C_{1-8}$ alkyl" indicates that the alkyl group has from 1 to 8 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —$(CH_2)_3CH_3$), sec-butyl (i.e. —$CH(CH_3)CH_2CH_3$), isobutyl (i.e. —$CH_2CH(CH_3)_2$) and tert-butyl (i.e. —$C(CH_3)_3$); and "propyl" includes n-propyl (i.e. —$(CH_2)_2CH_3$) and isopropyl (i.e. —$CH(CH_3)_2$).

"Alkylene" (including those which are part of other groups) refers to branched and unbranched divalent "alkyl" groups. As used herein, alkylene has 1 to 20 carbon atoms (i.e., $C_{1-20}$alkylene), 1 to 8 carbon atoms (i.e., $C_{1-8}$ alkylene), 1 to 6 carbon atoms (i.e., $C_{1-6}$ alkylene), or 1 to 4 carbon atoms (i.e., $C_{1-4}$ alkylene). Examples include: methylene, ethylene, propylene, 1-methylethylene, butylene, 1-methylpropylene, 1,1-dimethylethylene or 1,2-dimethylethylene. Unless stated otherwise, the definitions propylene and butylene include all the possible isomeric forms of the groups in question with the same number of carbons. Thus, for example, propylene also includes 1-methylethylene and butylene includes 1-methylpropylene, 1,1-dimethylethylene, and 1,2-dimethylethylene.

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy. "Haloalkoxy" refers to an alkoxy group as defined above, wherein one or more hydrogen atoms are replaced by a halogen.

The term "cyano," as used herein, refers to CN.

The term "cycloalkyl," as used herein, refers to a group derived from a monocyclic saturated carbocycle, having preferably three to eight, more preferably three to six, carbon atoms, by removal of a hydrogen atom from the saturated carbocycle. Representative examples of cycloalkyl groups include, but are not limited to, cyclopropyl, cyclopentyl, and cyclohexyl. When a cycloalkyl group contains one or more double bond(s) in the ring, yet not aromatic, it forms a "cycloalkenyl" group.

The terms "halo" and "halogen," as used herein, refer to F, Cl, Br, or I.

The term "haloalkyl," as used herein, refers to alkyl group substituted by at least one halogen atom. The haloalkyl group can be an alkyl group of which all hydrogen atoms are substituted by halogens.

The term "heteroaryl," as used herein, monocyclic or bicyclic aromatic group comprising one or more, preferably one to three, heteroatoms independently selected from nitrogen, oxygen, and sulfur in the aromatic ring(s). As is well known to those skilled in the art, heteroaryl rings have less aromatic character than their all-carbon counterparts. Illustrative examples of heteroaryl groups include, but are not limited to, pyridyl, pyridazinyl, pyrimidyl, pyrazyl, triazinyl, pyrrolyl, pyrazolyl, imidazolyl, pyrimidinyl, furyl, thienyl, isoxazolyl, thiazolyl, isoxazolyl, oxazolyl, indolyl, quinolinyl, isoquinolinyl, benzisoxazolyl, benzothiazolyl, and benzothienyl.

The term "heterocyclyl," as used herein, refers to monocyclic or bicyclic nonaromatic group comprising one or more, preferably one to three, heteroatoms independently selected from nitrogen, oxygen, and sulfur in the nonaromatic ring(s). The heterocyclyl groups of the present disclosure can be attached to the parent molecular moiety through a carbon atom or a nitrogen atom in the group. A heterocylcyl group can be saturated or unsaturated, for example, containing one or more double bond(s) in the ring. Examples of heterocyclyl groups include, but are not limited to, morpholinyl, oxazolidinyl, piperazinyl, piperidinyl, pyrrolidinyl, tetrahydrofuryl, thiomorpholinyl, and indolinyl, or the like.

The terms "hydroxy" or "hydroxyl," as used herein, refers to OH.

The term "nitro," as used herein, refers to $NO_2$.

The term "substituted" as used herein, refers to independent replacement of one, two, or three or more of the hydrogen atoms thereon with substituents including, but not limited to, —F, —Cl, —Br, —I, —OH, protected hydroxy, —$NO_2$, —CN, —$NH_2$, —$N_3$, protected amino, alkoxy, thioalkoxy, oxo, hydroxyalkyl, hydroxyalkenyl, hydroxyalkynyl, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH-alkyl, —NH-alkenyl, —NH-alkynyl, —NH-cycloalkyl, —NH-aryl, —NH-heteroaryl, —NH-heterocycloalkyl, -dialkylamino, -diarylamino, -diheteroarylamino, —O-alkyl, —O-alkenyl, —O-alkynyl, —O-cycloalkyl, —O-aryl, —O-heteroaryl, —O-heterocycloalkyl, —C(O)-alkyl, —C(O)-alkenyl, —C(O)-alkynyl, —C(O)-cycloalkyl, —C(O)-aryl, —C(O)-heteroaryl, —C(O)-heterocycloalkyl, —$CONH_2$, —CONH-alkyl, —CONH-alkenyl, —CONH-alkynyl, —CONH-cycloalkyl, —CONH-aryl, —CONH-heteroaryl, —CONH-heterocycloalkyl, —$OCO_2$-alkyl, —$OCO_2$-alkenyl, —$OCO_2$-alkynyl, —$OCO_2$-cycloalkyl, —$OCO_2$-aryl, —$OCO_2$-heteroaryl, —$OCO_2$-heterocycloalkyl, —$OCONH_2$, —OCONH-alkyl, —OCONH-alkenyl, —OCONH-alkynyl, —OCONH-cycloalkyl, —OCONH-aryl, —OCONH-heteroaryl, —OCONH-heterocycloalkyl, —NHC(O)-alkyl, —NHC(O)-alkenyl, —NHC(O)-alkynyl, —NHC(O)-cycloalkyl, —NHC(O)-aryl, —NHC(O)-heteroaryl, —NHC(O)-heterocycloalkyl, —$NHCO_2$-alkyl, —$NHCO_2$-alkenyl, —$NHCO_2$alkynyl, —$NHCO_2$-cycloalkyl, —$NHCO_2$aryl, —$NHCO_2$-heteroaryl, —$NHCO_2$-heterocycloalkyl, —$NHC(O)NH_2$, —NHC(O)NH-alkyl, —NHC(O)NH-alkenyl, —NHC(O)NH-alkynyl, —NHC(O)NH-cycloalkyl, —NHC(O)NH-aryl, —NHC(O)NH-heteroaryl, —NHC(O)NH-heterocycloalkyl, $NHC(S)NH_2$, —NHC(S)NH-alkyl, —NHC(S)NH-alkenyl, —NHC(S)NH-alkynyl, —NHC(S)NH-cycloalkyl, —NHC(S)NH-aryl, —NHC(S)NH-heteroaryl, —NHC(S)NH-heterocycloalkyl, —$NHC(NH)NH_2$, —NHC(NH)NH-alkyl, —NHC(NH)NH-alkenyl, —NHC(NH)NH-alkynyl, —NHC(NH)NH-cycloalkyl, —NHC(NH)NH-aryl, —NHC(NH)NH-heteroaryl, —NHC(NH)NH-heterocycloalkyl, —NHC(NH)-alkyl, —NHC(NH)-alkenyl, —NHC(NH)-alkynyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-alkynyl, —S(O)-cycloalkyl, —S(O)-aryl, —S(O)-heteroaryl, —S(O)-heterocycloalkyl-$SO_2NH_2$, —$SO_2$NH-alkyl, —$SO_2$NH-alkenyl, —$SO_2$NH-alkynyl, —SO$_2$NH-cycloalkyl, —SO$_2$NH-aryl, —SO$_2$NH-heteroaryl, —SO$_2$NH-heterocycloalkyl, —NHSO$_2$-alkyl, —NHSO$_2$-alkenyl, —NHSO$_2$-alkynyl, —NHSO$_2$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, -cycloalkyl, -polyalkoxyalkyl, -polyalkoxy, -methoxymethoxy, -methoxyethoxy, —SH, —S-alkyl, —S-alkenyl, —S-alkynyl, —S-cycloalkyl, —S-aryl, —S-heteroaryl, —S-heterocycloalkyl, methythiomethyl, or -L'-R', wherein L' is C$_1$-C$_6$alkylene, C$_2$-C$_6$alkenylene or C$_2$-C$_6$alkynylene, and R' is aryl, heteroaryl, heterocyclic, C$_3$-C$_{12}$cycloalkyl or C$_3$-C$_{12}$cycloalkenyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —NO$_2$, —CN, or —NH$_2$.

When any group, for example, alkyl, alkenyl, "cycloalkyl," "aryl," "heterocyclyl," or "heteroaryl", is said to be "optionally substituted," unless specifically defined, it means that the group is or is not substituted by from one to five, preferably one to three, substituents independently selected from halogen, alkyl, alkoxy, haloalkyl, haloalkoxy, hydroxy, oxo, acyl, cyano, nitro, and amino group, or the like, provided that such substitution would not violate the conventional bonding principles known to a person of ordinary skill in the art. When the phrase "optionally substituted" is used before a list of groups, it means that each one of the groups listed may be optionally substituted.

The term "artemisinin-derived dimers, trimers and tetramers", "artesunate-derived dimers, trimers and tetramers", "dihydroartemisinin-derived dimers, trimers and tetramers" and "deoxoartemisinin-derived dimers, trimers and tetramers" as used in this specification encompasses any of the individual enantiomers of artemisinin, artesunate, dihydroartemisinin or deoxoartemisinin; the term may refer to just a single enantiomer, or a racemic or non-racemic mixture of the enantiomers. The terms "artemisinin-derived dimers, trimers and tetramers", "artesunate-derived dimers, trimers and tetramers", "dihydroartemisinin-derived atives dimers, trimers and tetramers" and "deoxoartemisinin-derived dimers, trimers and tetramers" also include polymorphs and hydrates of these compounds. The terms "artemisinin-derived dimers, trimers and tetramers", "artesunate-derived dimers, trimers and tetramers", "dihydroartemisinin-derived dimers, trimers and tetramers" or "deoxoartemisinin-derived dimers, trimers and tetramers" also include salts and esters of these compounds. The term "artemisinin", "artesunate", "dihydroartemisinin" or "deoxoartemisinin" also includes prodrugs of these compounds, and enantiomers, racemic mixtures, non-racemic mixtures, polymorphs, hydrates, salts and esters of said prodrugs.

The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously.

The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

The term "buffering agent" as used herein denotes a pharmaceutically acceptable excipient, which stabilizes the pH of a pharmaceutical preparation. Suitable buffering agents are well known in the art and can be found in the literature.

The term "subject" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

Compounds

In one aspect, the present disclosure relates to compounds of formula (I):

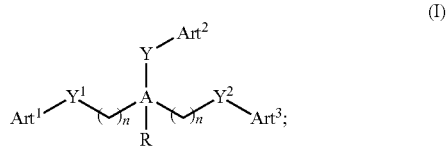

wherein:

n is an integer from 0 to 6;

Art$^1$, Art$^2$ and Art$^3$ are each independently selected from:

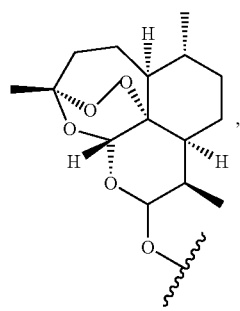

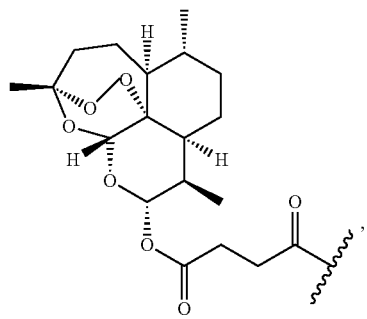

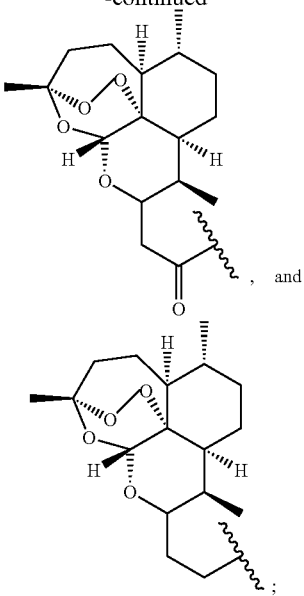

wherein A is selected from carbon, nitrogen, and

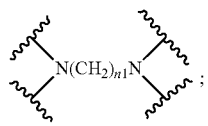

wherein n1 is an integer selected from 0 to 12;
Y, Y¹, and Y² are each independently selected from absent, O, NH, NR¹, S(O)$_m$, —(CHR¹)$_{n2}$—, —(CHR¹)$_{n2}$O—, —(CHR¹)$_{n2}$N—, —(CHR¹)$_{n2}$C(=O)—, —(CHR¹)$_{n2}$C(=O)O—, —(CHR¹)$_{n2}$C(=O)NR¹—, —(CHR¹)$_{n2}$S(O)$_m$—, and —(CHR¹)$_{n2}$C(=O)S—; wherein n2 is an integer selected from 0 to 6; and m is an integer selected from 0 to 2; and R is selected from absent, hydrogen, —OR¹, —C(O)R¹, —C(O)OR¹, —(CHR²)$_{n3}$R¹, —(CHR²)$_{n3}$OR¹, —NR²R¹, —(CHR²)$_{n3}$NR²R¹, —NR²C(O)R¹, —NR²C(O)OR¹, —NR²C(O)NHR¹, —(CHR²)$_3$OC(O)R¹, —(CHR²)$_{n3}$OC(O)OR¹, —N=BR¹, and —NHS(O)$_m$R¹; wherein n3 is an integer selected from 0 to 4; and m is an integer selected from 0 to 2; and wherein B is selected from N and C; R¹ and R² are each independently selected from hydrogen, Art¹, Art², Art³, C$_{1-6}$alkyl, C$_{1-6}$haloalkyl, C$_{1-6}$haloalkoxyl, C$_{2-6}$alkenyl, C$_{2-6}$alkynyl, C$_{1-6}$alkylene, COOC$_{1-6}$alkyl, C$_{1-6}$alkyleneCOOH, C$_{3-12}$cycloalkyl, 3-12 membered heterocyclyl, C$_{6-12}$aryl, and 5-12 membered heteroaryl;

wherein each C$_{1-6}$alkyl, C$_{2-6}$alkenyl, C$_{2-6}$alkynyl, C$_{1-6}$alkyleneCOOC$_{1-6}$alkyl, C$_{1-6}$alkyleneCOOH, C$_{6-12}$aryl, 3-12 membered heterocyclyl, and 5-12 membered heteroaryl of R¹ and R² is independently optionally substituted with one to ten groups selected from halo, hydroxyl, amino, cyano, C$_{1-6}$alkyl, C$_{1-6}$haloalkyl, C$_{1-6}$alkoxyl, C$_{1-6}$haloalkyl, C$_{3-6}$cycloalkyl, and 3-6 membered heterocyclyl.

The compounds of the present disclosure can also exist in the form of enantimers, diastereomers, racemates, pharmaceutically acceptable salts, prodrugs, or solvates, namely in the form of associations with one or more molecules of water or a solvent.

In some embodiments, R is absent; and n is 1. In some embodiments, Y¹ and Y² are —CH₂O—; Y is —CH₂CH₂O—; and A is selected from nitrogen and carbon. In some embodiments, Y¹ and Y² are —CH₂—. In some embodiments, the compound of formula (I) is selected from:

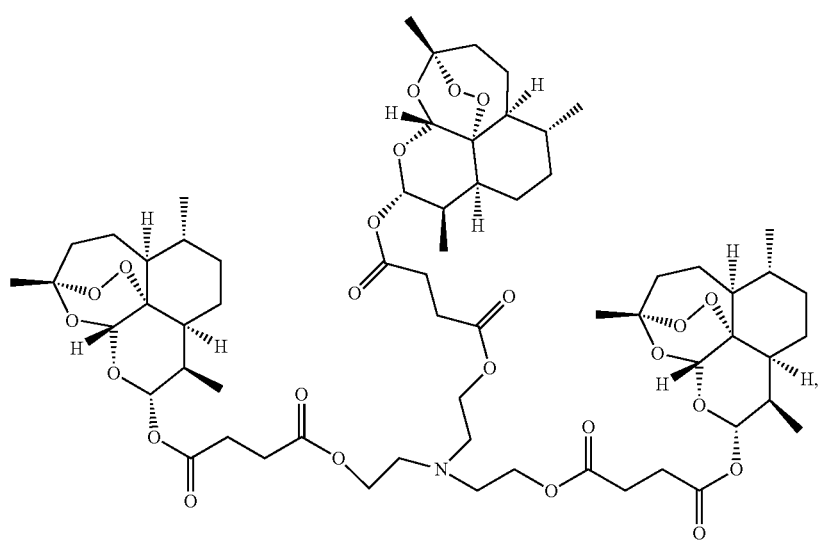

-continued
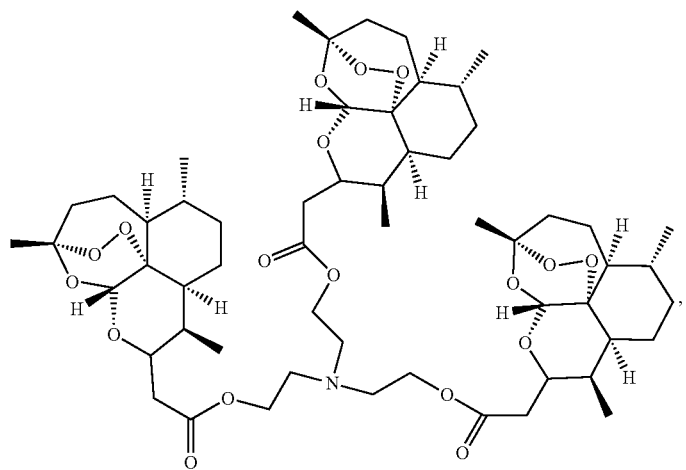
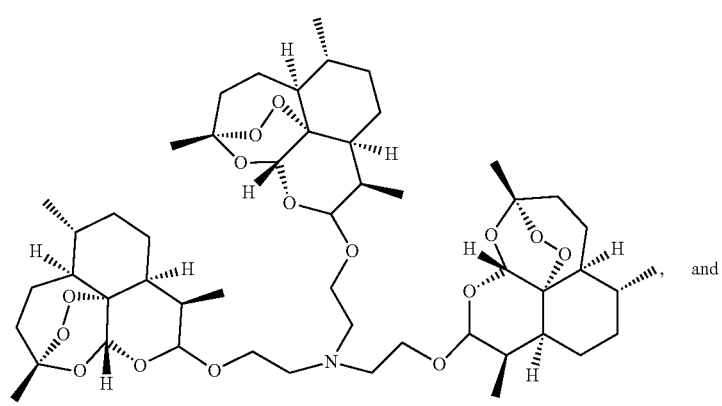, and
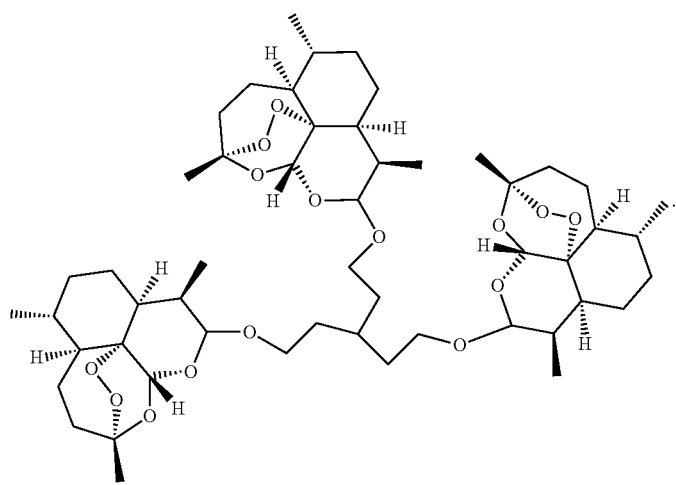

In some embodiments, $Y^1$ and $Y^2$ are —C(=O)O—; Y is —CH$_2$C(=O)O—; A is nitrogen; R is absent; and n is 1. In some embodiments, $Y^1$ and $Y^2$ are —C(=O)—. In some embodiments, the compound of formula (I) is selected from:
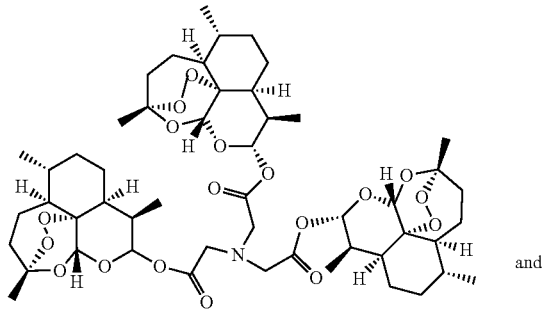
and
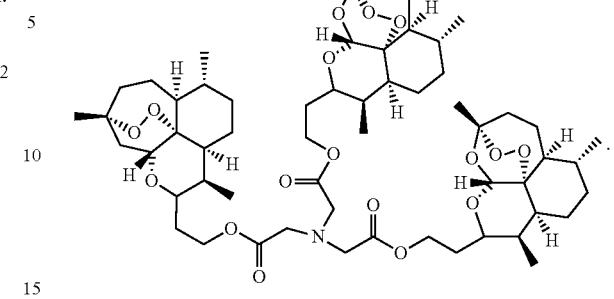
In some embodiments, A is nitrogen; Y, $Y^1$, and $Y^2$ are each a bond; R is absent; and n is 0. In some embodiments, the compound of formula (I) is selected from:
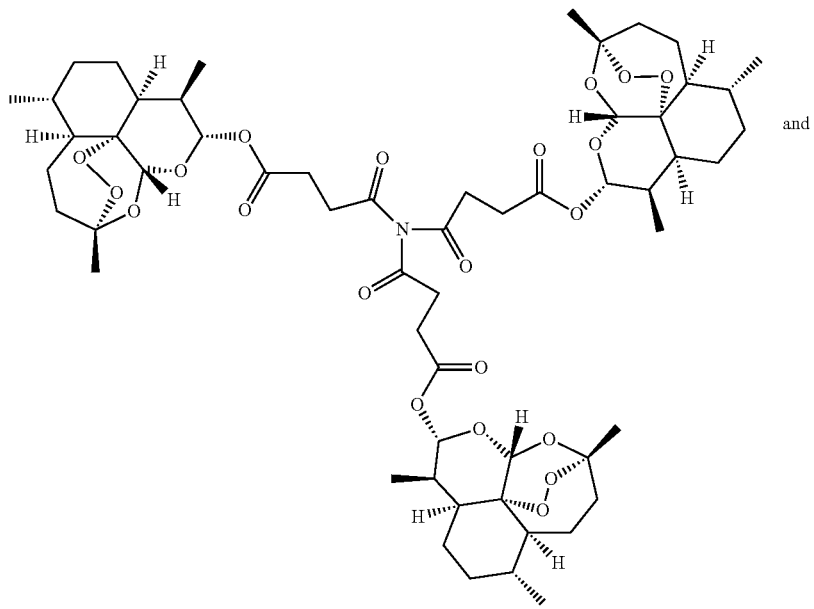
and
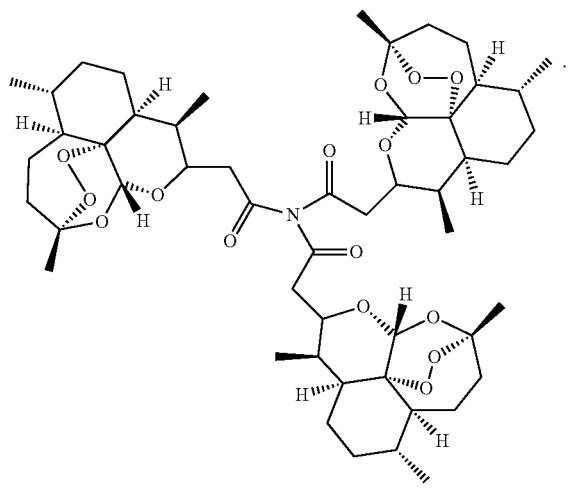

In some embodiments, A is carbon; Y, Y¹ and Y² are —O—; n is 1; and R is hydrogen. In some embodiments, at least two of Y, Y¹, and Y² are —O—. In some embodiments, at least one of Y, Y¹, and Y² is —NH—. In some embodiments. Y¹ and Y² are absent. In some embodiments, the compound of formula (I) is selected from:
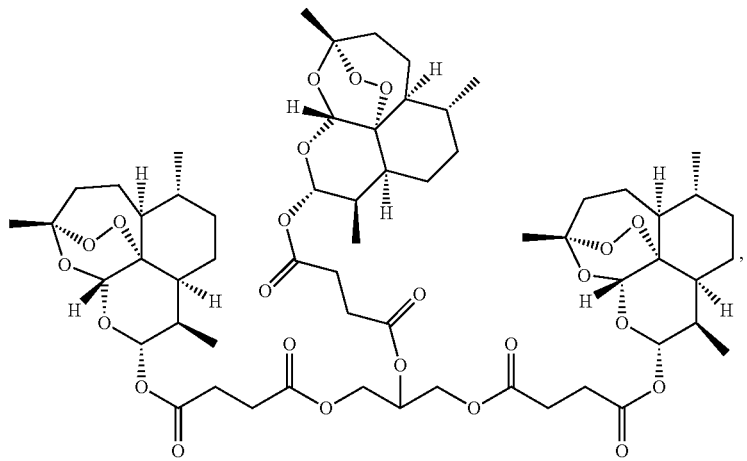
3
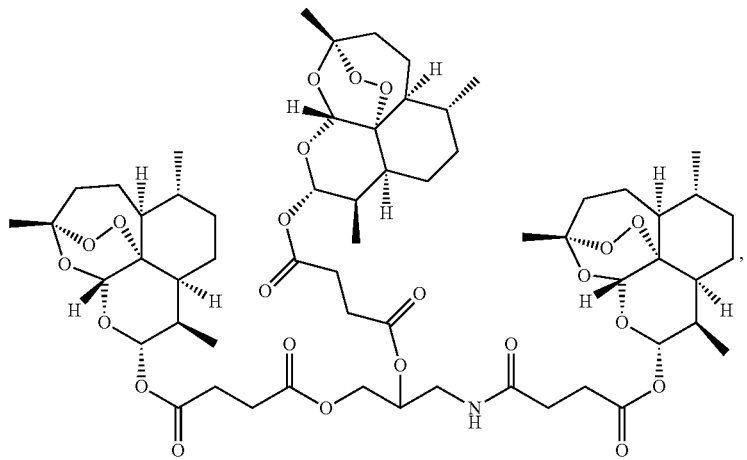
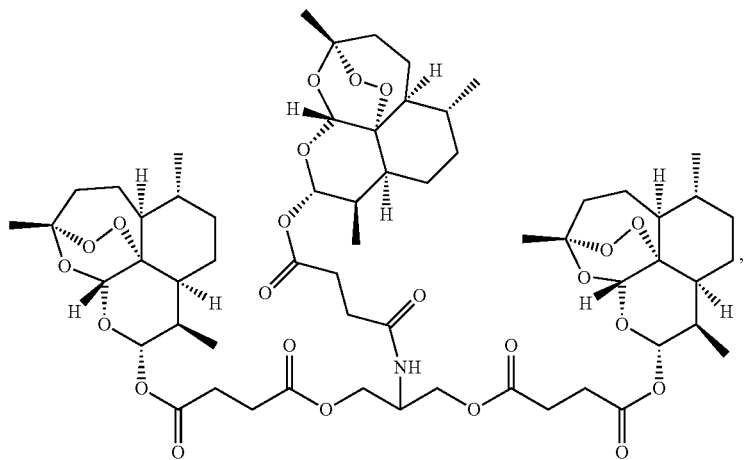
4

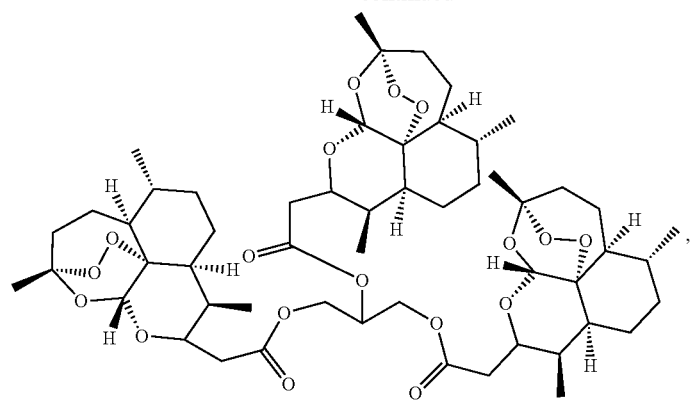
,
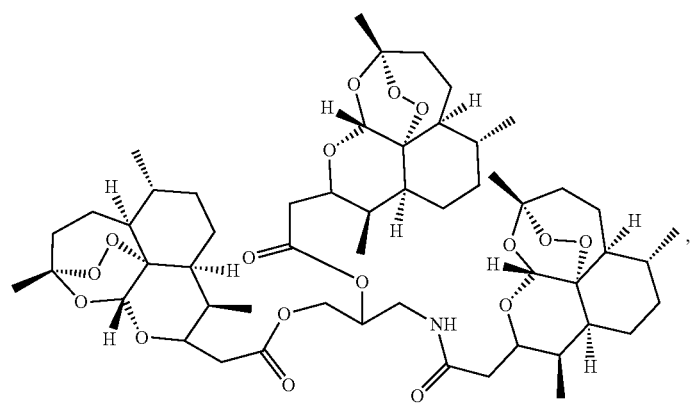
,
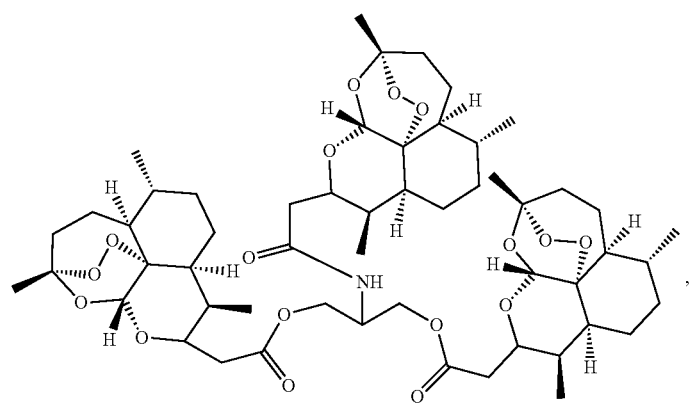
,
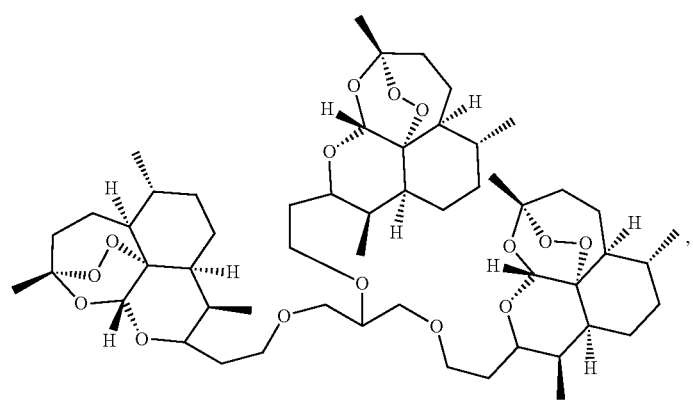
,

-continued
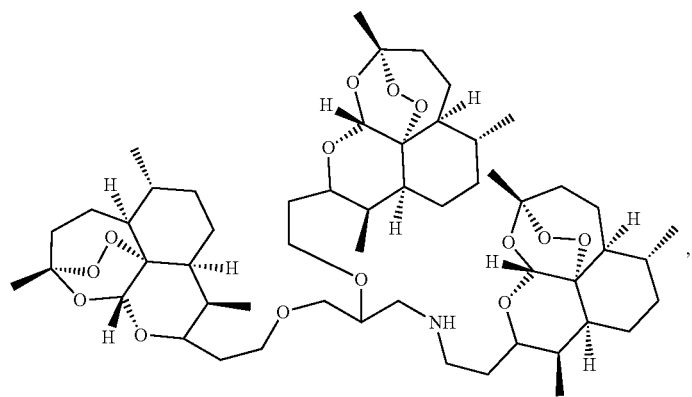
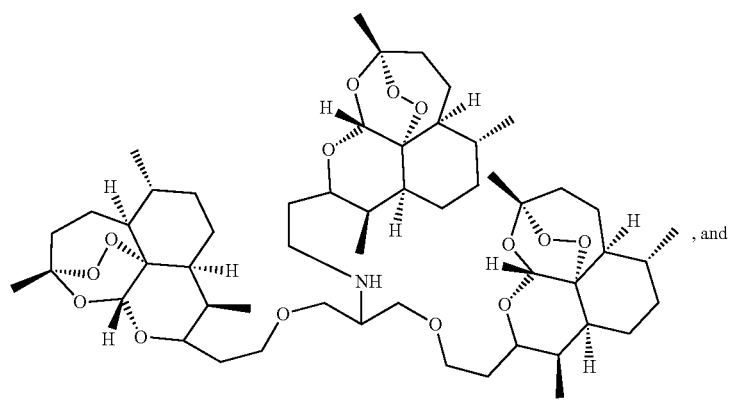
, and
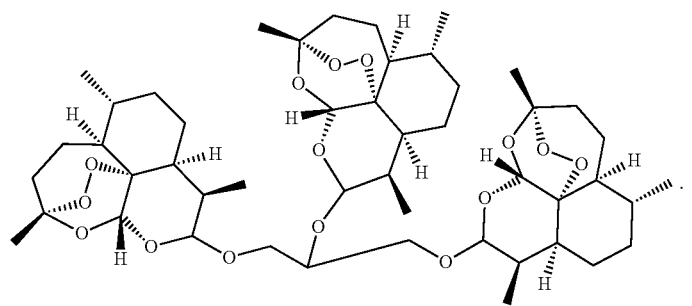
.

In some embodiments, A is carbon; n is 1; $Y^1$ and $Y^2$ are oxygen; Y is —CH$_2$O—; R is —CH$_2$OR$^1$, wherein R$^1$ is selected from hydrogen, —C(=O)CH$_2$CH$_2$COOH, Art$^1$, Art$^2$ and Art$^3$. In some embodiments, $Y^1$ and $Y^2$ are absent; and $Y^3$ is —CH$^2$—. In some embodiments, the compound of formula (I) is selected from:
5
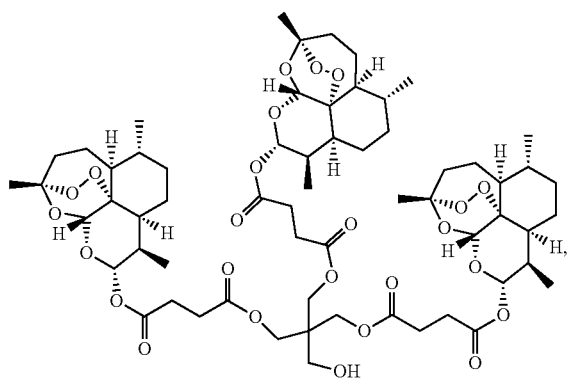
6
-continued
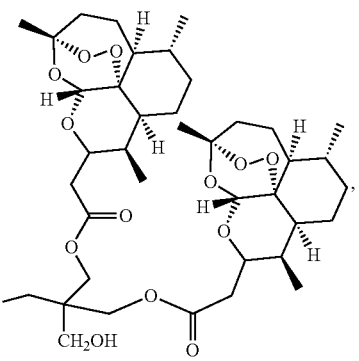
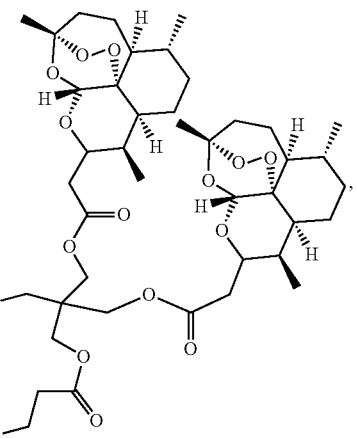
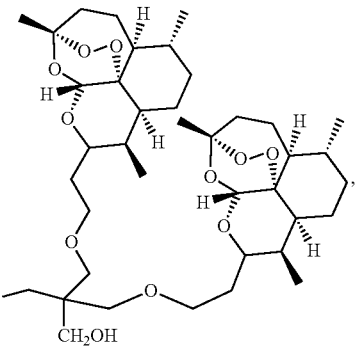
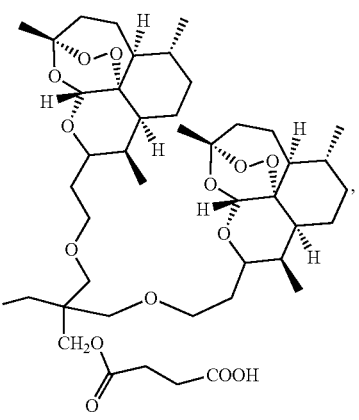

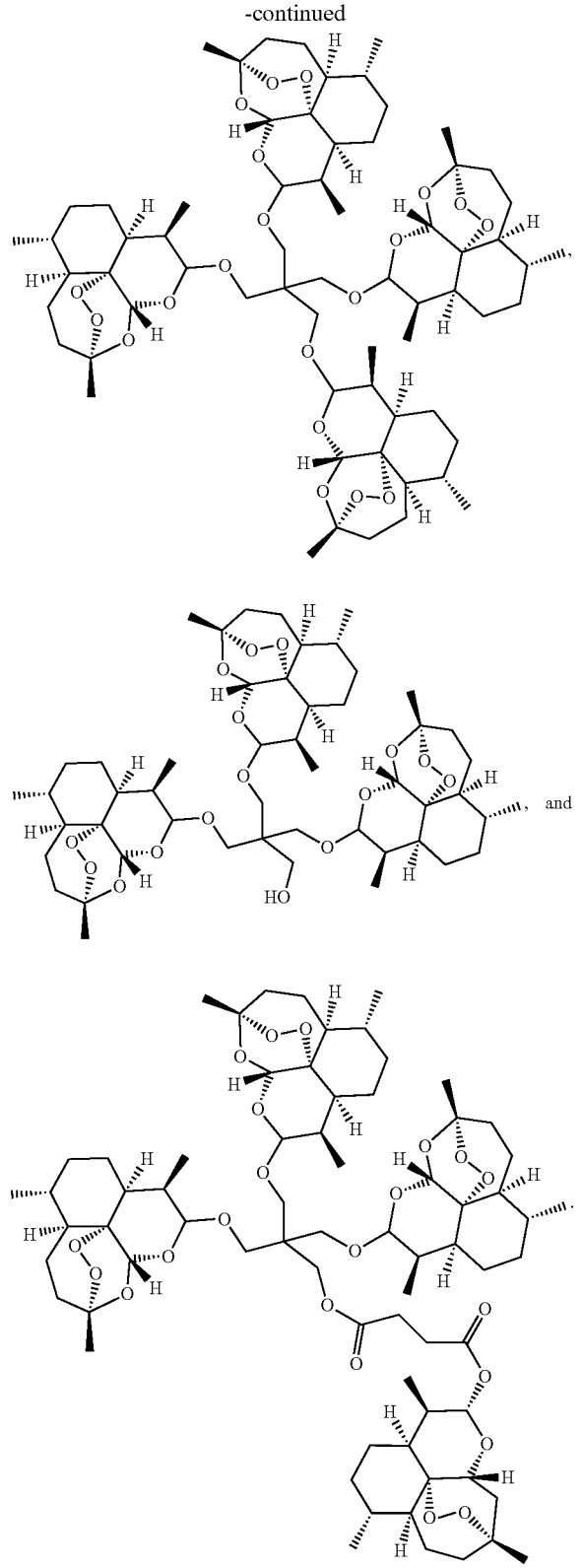
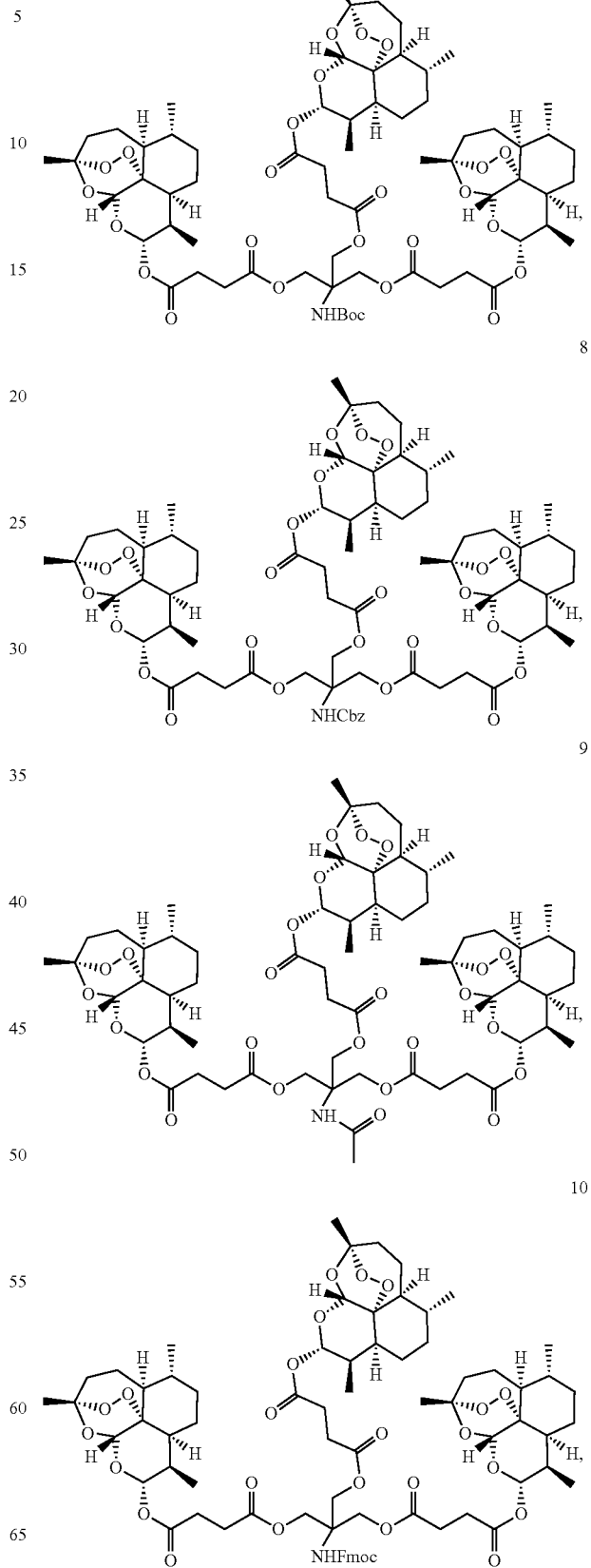
In some embodiments, R is —NHR[1]. In some embodiments, R is —NHC(=O)R[1]. In some embodiments, R is —NHC(=O)OR[1]. In some embodiments, R is —NHC(=O)NHR[1]. In some embodiments, the compound of formula (I) is selected from:

27
-continued
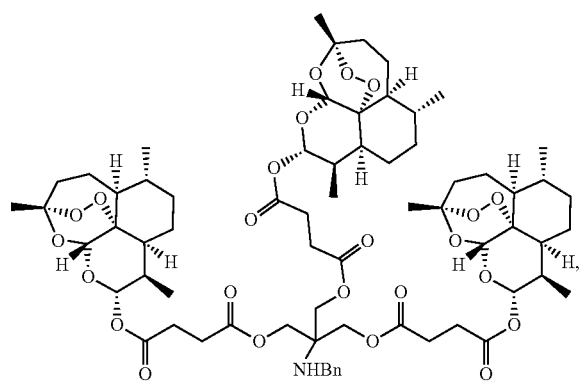
11
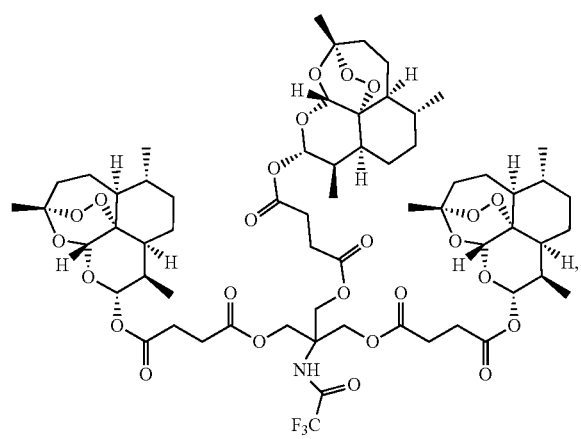
28
-continued
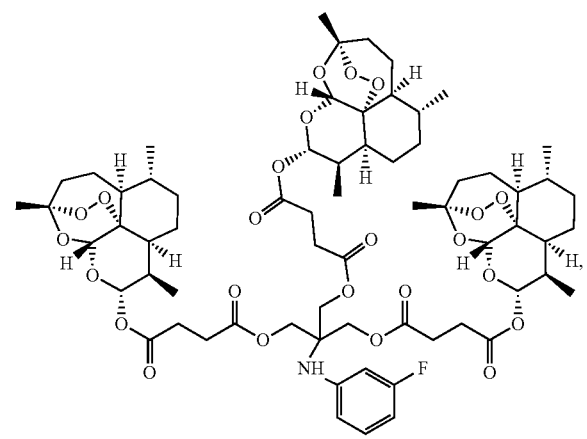
12
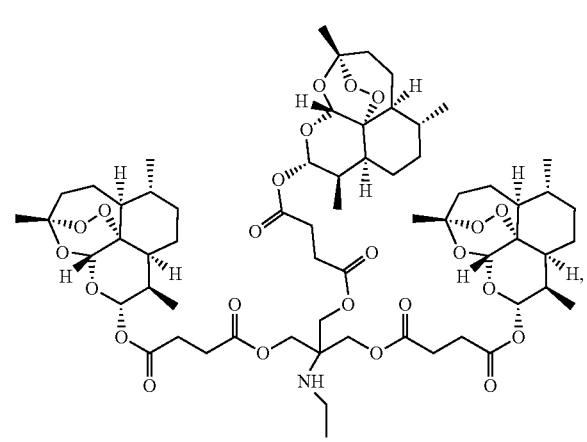

29
-continued
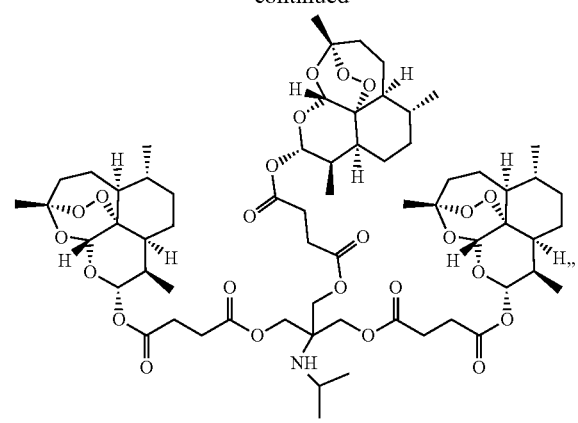
30
-continued
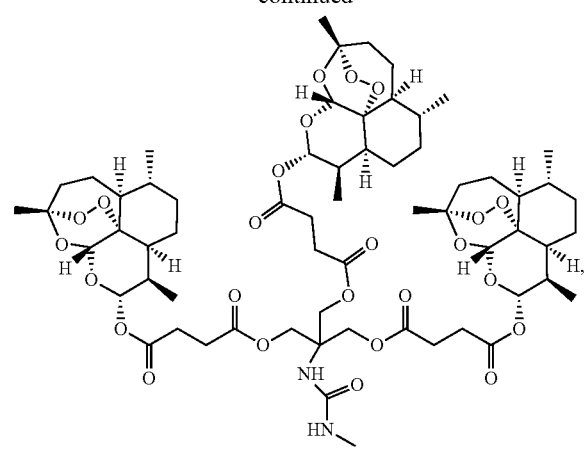

31
-continued
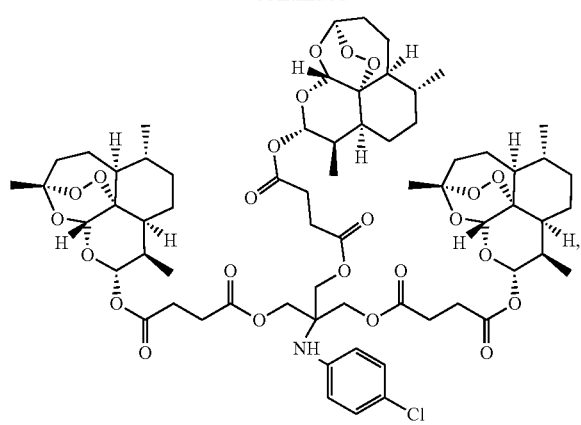
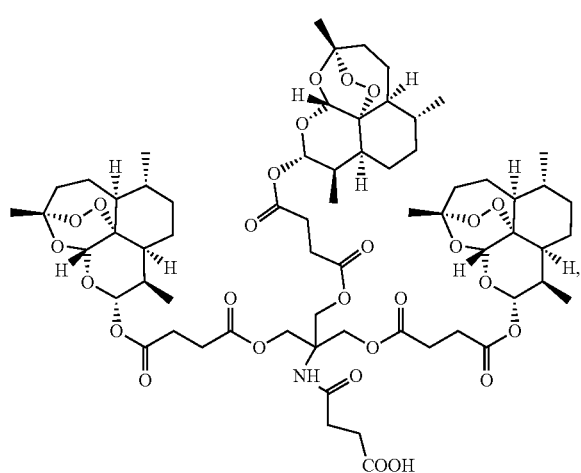
32
-continued
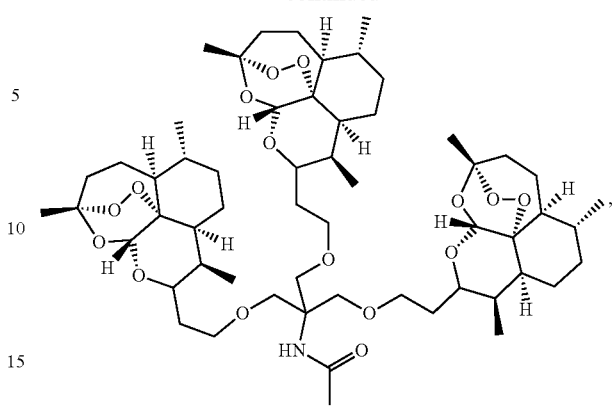
and
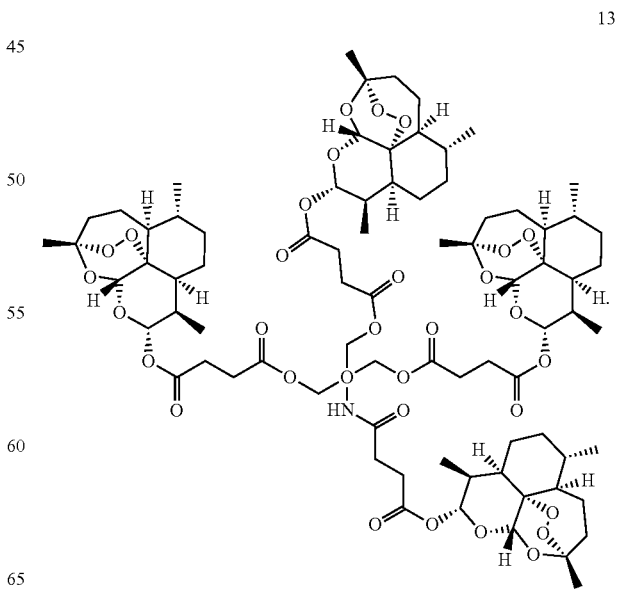

In some embodiments, R is N=BR$_1$. In some embodiments, the compound of formula (I) is selected from:
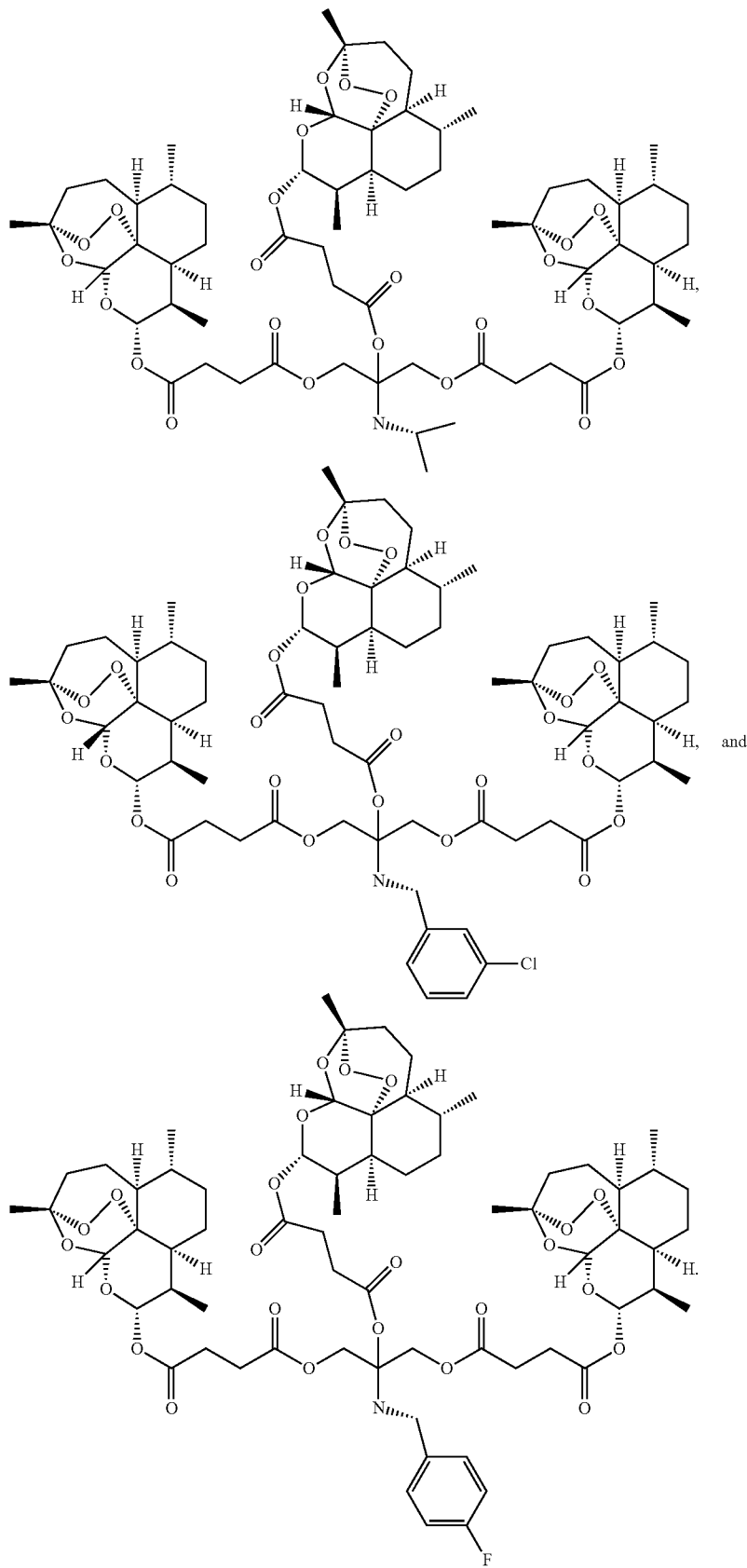

In some embodiments, R is —NHS(O)$_2$R$^1$. In some embodiments, the compound of formula (I) is selected from:
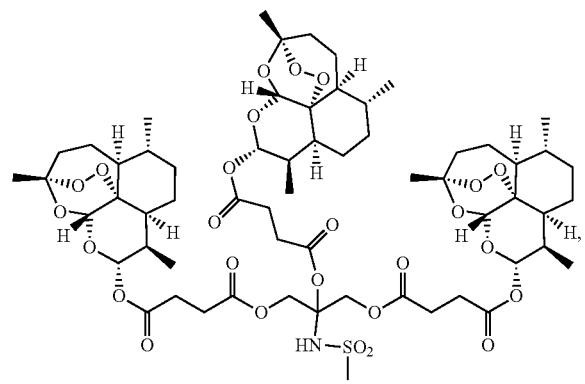
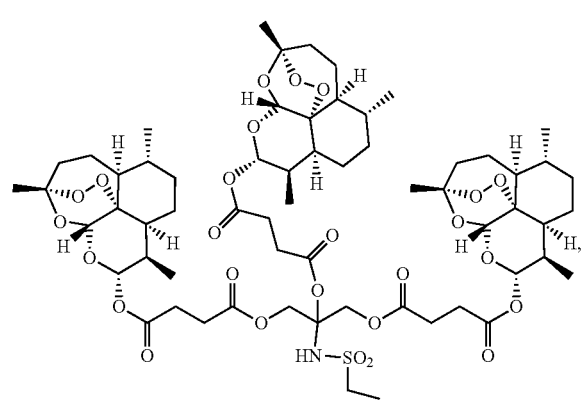
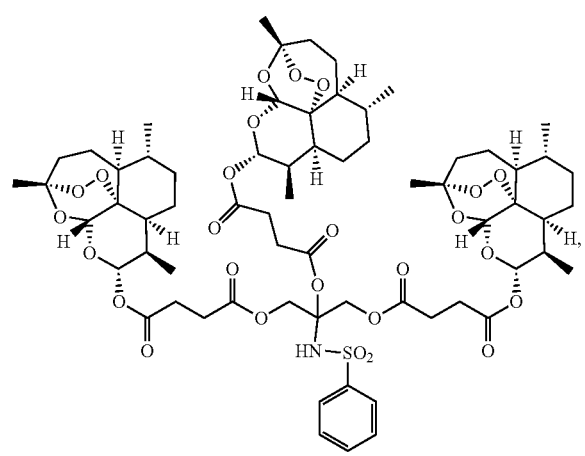
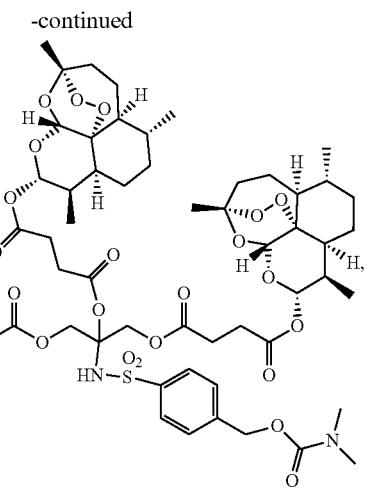
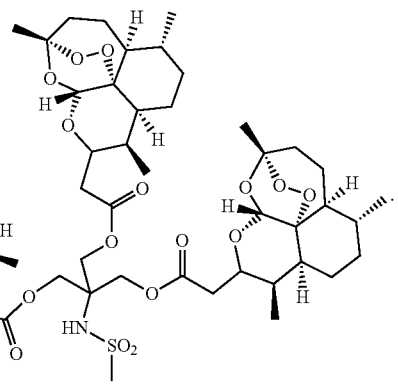
and In some embodiments, A is carbon; R is absent; $Y^1$, $Y^2$ and Y are oxygen; and n is 0. In some embodiments, $Y^1$, $Y^2$ are absent. In some embodiments, the compound of formula (I) is selected from:

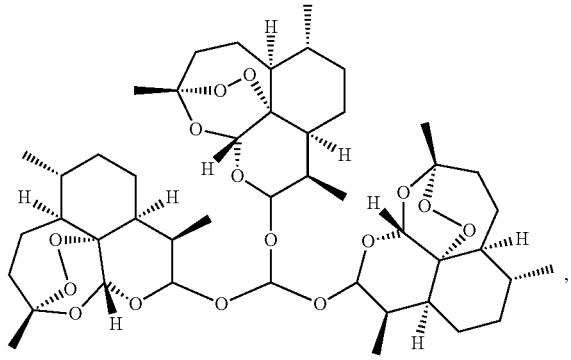

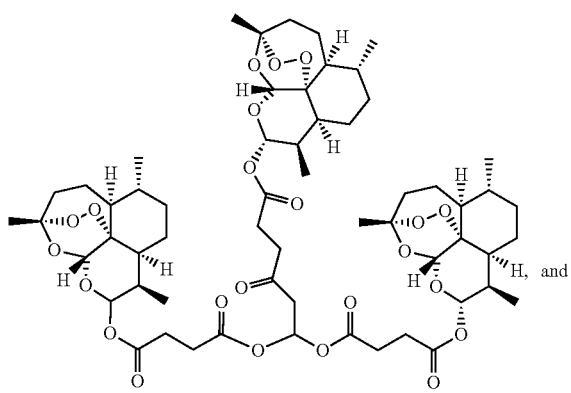

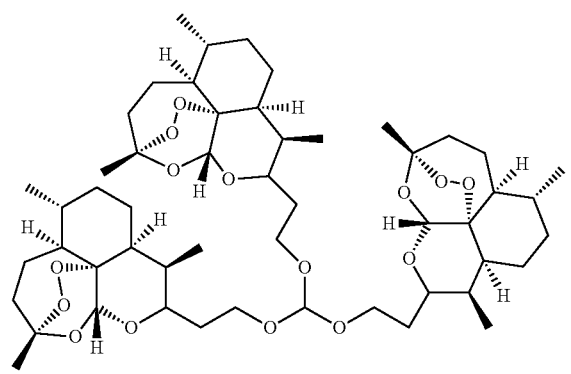

In some embodiments, A is carbon; Y, Y1 and Y2 are —C(═O)—; n is 1; and R is hydrogen. In some embodiments, Y1 and Y2 are —C(═O)—. In some embodiments, the compound of formula (1) is selected from:

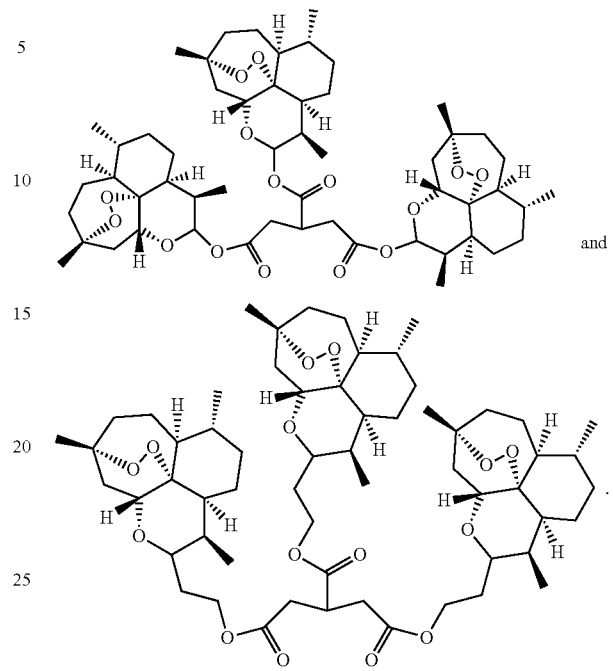

In some embodiments, $Y^1$ and $Y^2$ are —C(═O)O—; Y is $CH_2C$(═O)O—. In some embodiments, R is $NHR^1$. In some embodiments, $Y^1$ and $Y^2$ are —C(═O)—. In some embodiments, R is OH. In a particular embodiment, the compound of formula (1) is selected from:

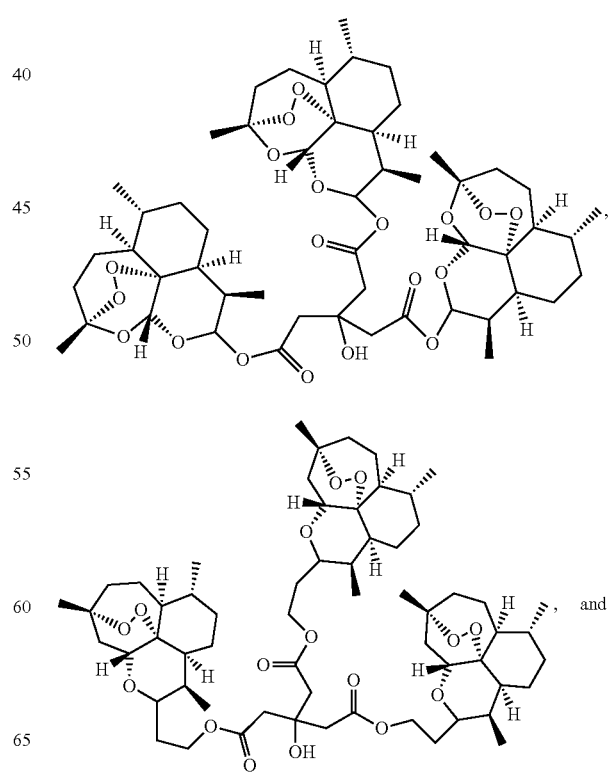

-continued
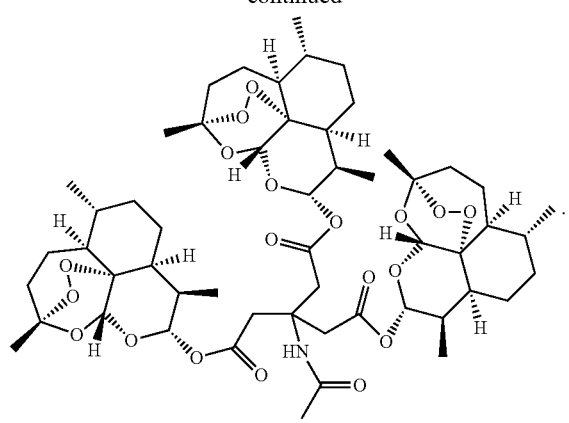
In some embodiments, A is
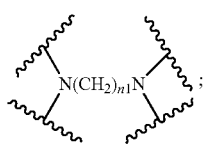
$Y^1$ and $Y^2$ are —$CH_2O$—; Y is —$CH_2CH_2O$—; n1 is 2; and R is —$CH_2CH_2OR^1$. $R^1$ is selected from hydrogen, $Art^1$, $Art^2$, and $Art^3$. In some embodiments, $Y^1$ and $Y^2$ are —$CH_2$—. In some embodiments, the compound of formula (I) is selected from:
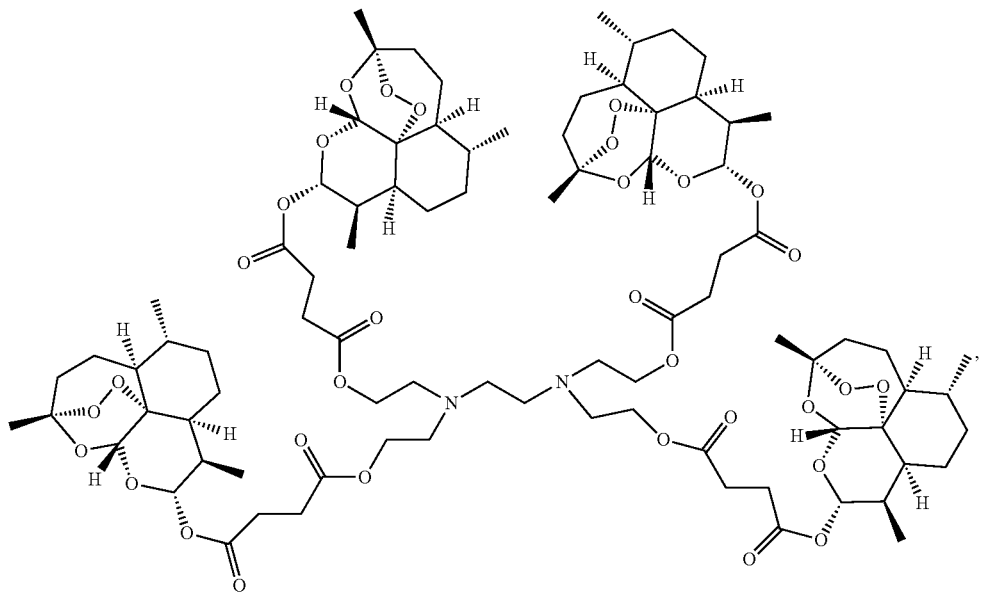
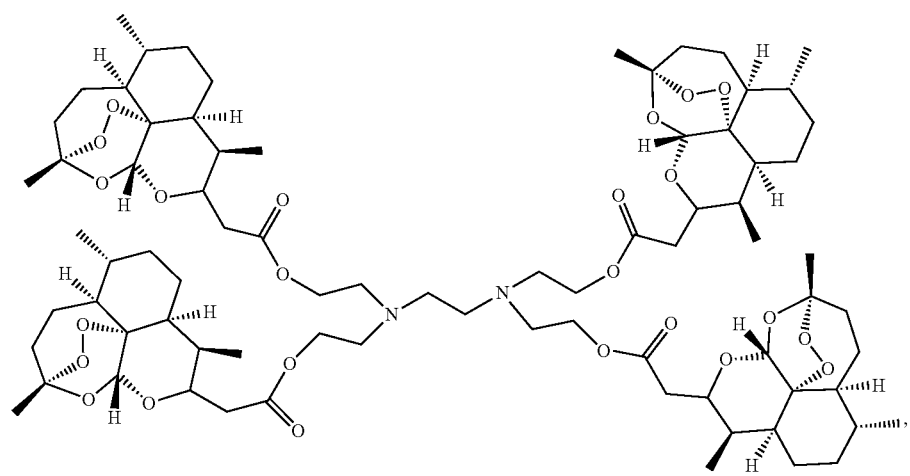

-continued
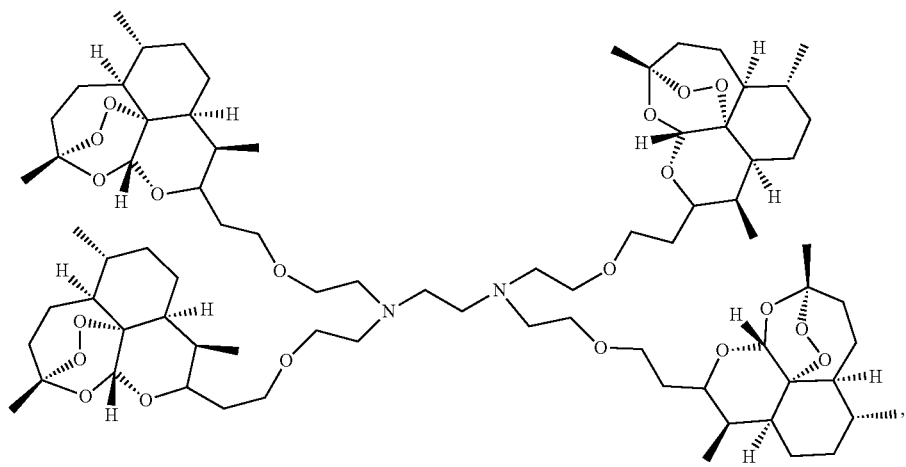
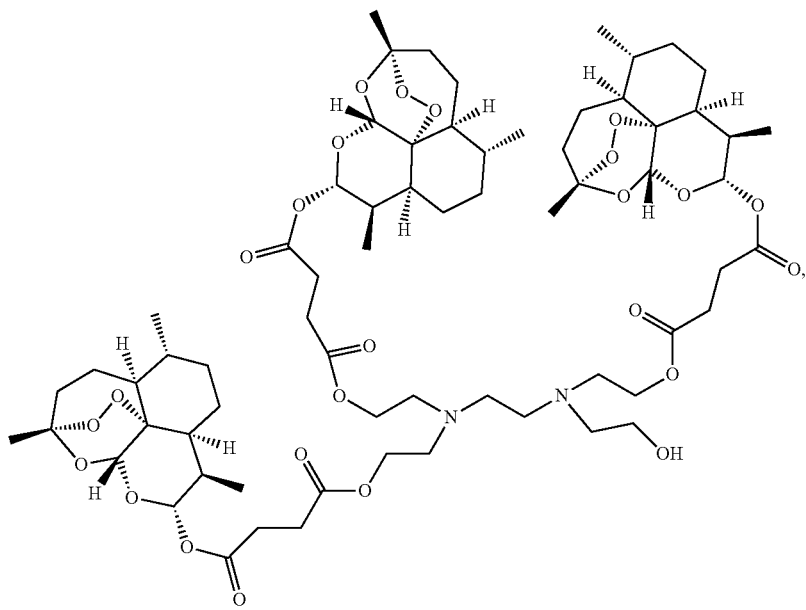
16
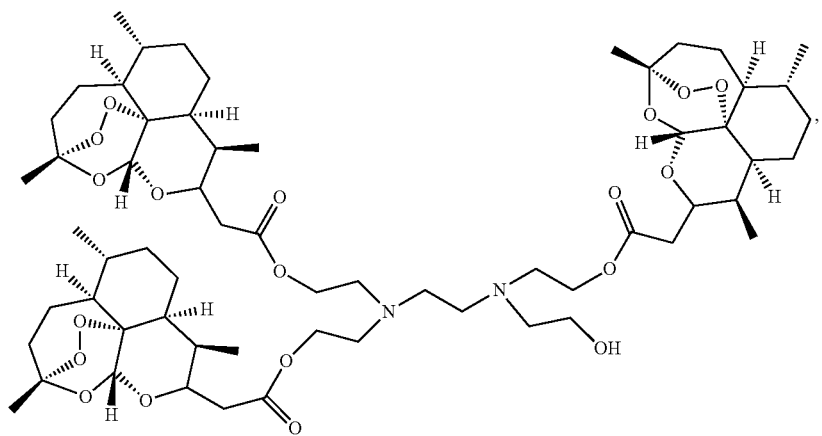

-continued
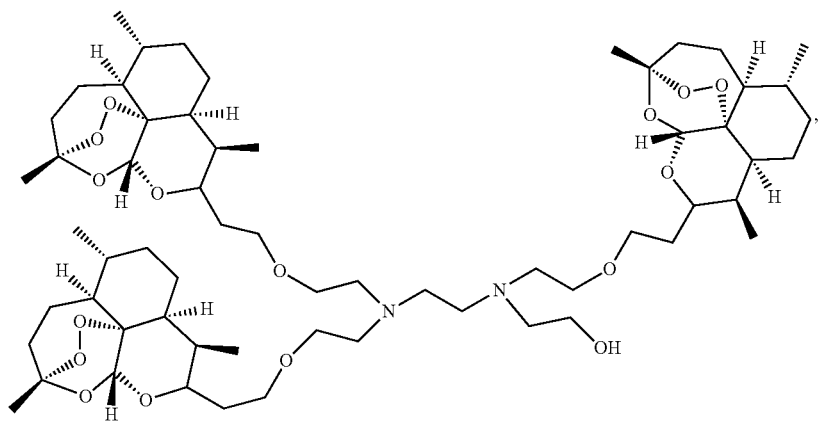
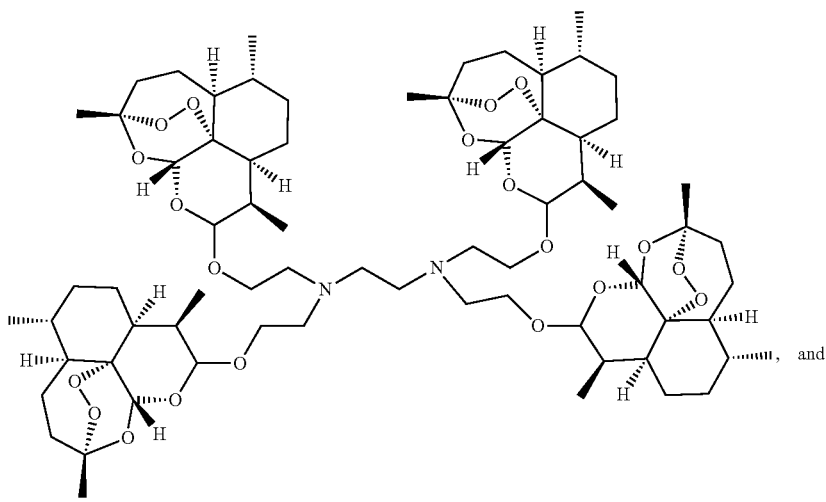, and
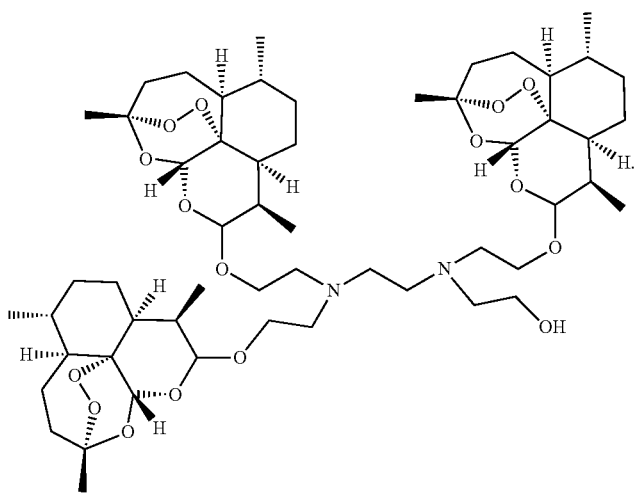

In some embodiments, $Y^1$ and $Y^2$ are —C(=O)O—; Y is —CH$_2$C(=O)O—; and R is —CH$_2$C(=O)R$^1$. In some embodiments, the compound of formula (1) is selected from:

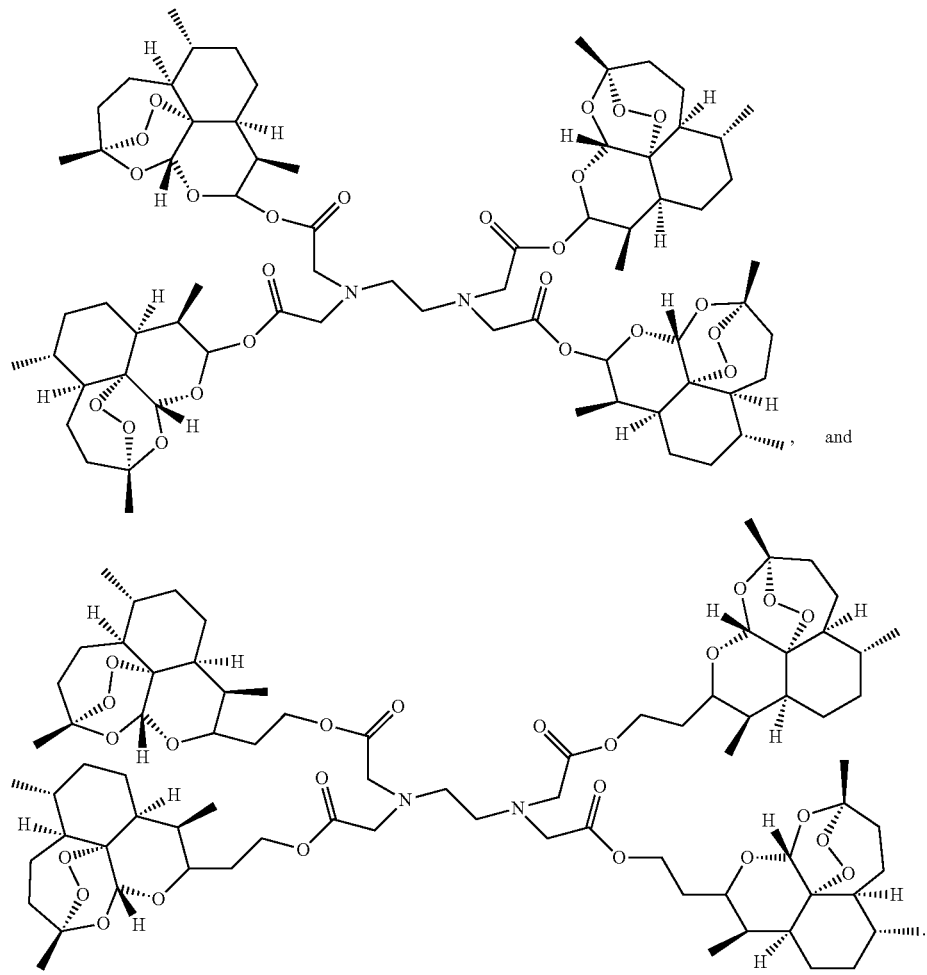

Compositions and Administration

The compounds of the present disclosure can be administered as pharmaceutical composition. According to a further aspect, the present disclosure provides pharmaceutical composition including one compound described herein, or a pharmaceutically acceptable salt or solvate thereof, in admixture with a pharmaceutically carrier/excipient thereof and optionally one or more other therapeutic ingredients.

In some embodiments, compositions include those suitable for oral, parenteral (including subcutaneous, intradermal, intramuscular, intravenous and intraarticular), rectal and topical (including dermal, buccal, sublingual, eye drop, conjunctival and intraocular) administration. The most suitable route may depend upon the condition and disorder of the recipient. The compositions may conveniently be presented in unit dosage form and may be prepared by any of the methods well known in the art of pharmacy. Techniques and formulations generally may be found in The Science and Practice of Pharmacy (Remington, 22$^{nd}$ edition, Lippincott, Williams &Wilkins, 2013).

The excipient or carrier in the composition described herein include an aqueous or oil base, thickening or gelling agents, hydrogels, emulsifying, nanoemulsifying, dispersing, solubilizing, stabilizing, suspending, and dispersing agents, coloring agents, or preservative agents. All the excipients mentioned herein are commercially available and published in literature (e.g. Hoepfner et al, Fiedler Encyclopedia of Excipients for Pharmaceuticals, Cosmetics and Related Areas, Edito-Cantor-Verlag, 2007).

Examples of suitable pharmaceutically acceptable carriers comprising excipients and auxiliaries include, but not limited to, water, ethanol, glycerol, sorbitol, corn starch, lactose, sucrose, microcrystalline cellulose, magnesium stearate, dextrose. polyvinylpyrrolidone, citric acid, tartaric acid, propyleneglycol, stearylalcohol, propyleneglycol, stearylalcohol, polyethyleneglycol, carboxymethylcellulose or fatty substances, saline and buffer solutions, edible oils (e.g. olive oil, soybean oil, sesame oil, or corn oil), cyclodextrins and lethicin.

For injection, the agents of the present disclosure may be formulated and diluted in aqueous solutions, such as in physiologically compatible buffers, physiological saline buffer, Tham's solution, Hank's solution, or Ringer's solution. Use of pharmaceutically acceptable inert carriers to formulate the compounds of the present disclosure in dosage forms suitable for systemic administration is within the scope of the disclosure. With proper carrier and suitable manufacturing practice, the compositions of the present disclosure may be administered parenterally, such as by intravenous injection.

For oral administration, the compound can be formulated as tablets, pills, capsules, solutions, gels, syrups, slurries, suspensions and the like using pharmaceutically acceptable carriers well known in the art. The pharmaceutical composition can be prepared by combining the active compounds from the present disclosure with excipients. Suitable excipients are fillers (such as sugars, including lactose, sucrose, mannitol, or sorbitol); cellulose preparations (e.g. maize starch, wheat starch, rice starch, potato starch, gelatin, gum tragacanth, methyl cellulose, hydroxypropylmethyl-cellulose, sodium carboxymethyl-cellulose, and/or polyvinylpyrrolidone). In addition, disintegrating agents may be added, such as the cross-linked polyvinylpyrrolidone, agar, or alginic acid or a salt thereof.

For nasal or inhalation delivery, the agents of the disclosure may also be formulated by methods known to those of skill in the art, and may include, but not limited to, examples of solubilizing, diluting, or dispersing substances, such as saline, preservatives, such as benzyl alcohol, absorption promoters, and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In some embodiments, compositions suitable for oral administration may be presented as discrete units such as capsules, cachets or tablets each containing a predetermined amount of the active ingredient; as a powder (including micronized and nanoparticulate powders) or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

In some embodiments, a tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

In some embodiments, the dose range for a subject is generally from about 0.00001 g to about 10 g/day, or 0.001 to 0.05 g/day. The precise effective amount of compound administered to a subject is well within the capability of those skilled in the art. For instance, the dose employed will depend on a number of factors, including age and body weight of the patient, the precise disorder being treated, and its severity. The frequency of administration will depend on the pharmacodynamics of the individual compound and the formulation of the dosage form, which may be optimized by methods well known in the art (e.g. controlled or extended release tablets, enteric coating, etc.).

In some embodiments, combination therapy can be achieved by administering two or more agents, each of which is formulated and administered separately, or by administering two or more agents in a single formulation.

In some embodiments, the composition comprises a compound from the present disclosure as a first therapeutic agent and a second therapeutic agent. In some embodiments, the second therapeutic agent is other antimalarial agents including, but not limited to, pyronaridine, mefloquine, piperaguine, primaquine, amodiaquine, sulfadoxine-pyrimethanmine, and lumefantrine.

In some embodiments, the second therapeutic agent is anticancer agents. Examples of known chemotherapeutic agents include, but are not limited to, doxorubicin, dexamethasone, vincristine, bleomycin, actinomycin D, cyclophosphamide, fluorouracil, topotecan, taxol, interferons, platinum derivatives, hydroxyurea, arsenic trioxide or other anticancer agents published in the literature.

The content of the compound from the present disclosure in the composition may be in the range of about 0.0001 to about 95% by weight/weight. In one example, the content is in the range of about 0.0001 to about 75% by weight/weight. In another example, the concentration is in the range of about 0.1 to about 5% by weight/weight. The desired content for use can be determined by people skilled in the art.

Methods of Treatment

A method for treating diseases or disorders associated with cancer comprises administrating a pharmaceutically effective amount of the disclosed composition or formulation to a subject. In some embodiments, the cancer includes, but not limited to, leukemia, colorectal cancer, brain/CNS cancer, bladder cancer, breast cancer, ovarian cancer, cervical cancer, endometrial cancer, lung cancer, melanoma, sarcoma, oral cavity and oropharyngeal cancer, renal cancer, pancreatic cancer, liver cancer and bone cancer.

In some embodiments, formulation of agents from the present disclosure can be used to treat parasitic infectious diseases including, but not limited to, malaria, *Schistosoma japonicum* and toxoplasma infections. In some examples, the malarial infection is caused by *Plasmodium falciparum*.

In some embodiments, the pharmaceutically effective amount of a compound from the present disclosure administered to a subject is about 0.002-10 mg/kg body weight once or twice per day or per week for about 1 to 180 days. The effective dosage may be affected by age, body weight or diseases to be treated, and can be selected by people skilled in the art.

In some embodiments, the disclosed composition or formulation is also can be used to treat virus infections, bacterial infections, organ injury, inflammatory and autoimmune disorders, eye diseases, heart diseases, sepsis, stroke, burns injury, liver diseases, lung disorders. In some embodiments virus infections include, but not limited to, cytomegalovirus, papillomavirus (HPV) and herpes viral infections. Bacterial infections include Gram-positive and Gram-negative bacterial infections. In some embodiments, the heart disease includes, but not limited to, cardiac hypertrophy, heart failure, myocardial infarct and coronary heart disease.

In some embodiments, the kidney disease includes, but not limited to, acute kidney disease, chronic kidney disease, lupus nephritis, glomerulus nephritis, kidney failure and uremia. In some embodiments, the inflammatory and autoimmune diseases include, but not limited to, rheumatoid arthritis, nephrotic syndrome, lupus, dermatomyositis, and pancreatitis. In some embodiments, eye diseases include, but not limited to, age-related macular degeneration, corneal neovascularization, diabetic retinopathy, diabetic macular edema, uveitis and retinal inflammation.

In some embodiments, the organ injury is induced by haemorrhage and the organ injury includes, but not limited to, trauma injury, pancreatitis injury, intestinal injury, brain and head injury, lung injury, kidney injury, liver injury, spinal cord injury and respiratory distress syndrome.

In some embodiments, a method of treating ischemia-reperfusion in a surgery comprises administrating to a subject a pharmaceutically effective amount of the disclosed composition or formulation. In some embodiments, the surgery includes, but not limited to kidney transplantation, kidney and pancreas transplantation, and coronary artery bypass graft.

Preparations

In some embodiments, compounds of the present disclosure can be prepared by coupling artesunate or its analogs with an appropriate optionally substituted compound (e.g. with hydroxyl, amino substituents). In some embodiments, compounds of the present disclosure can be prepared by coupling dihydroartemisinin or its analogs with an appropriate optionally substituted carboxylic acid (e.g. tricarboxyl or tertacarboxyl). The coupling reagents described herein is to form esters, ether or amides and examples of these agents include, but not limited to, N,N'-Dicyclohexylcarbodiimide (DCC), Diisopropylcarbodiimide (DIC), 1-Ethyl-3-(3-dimethylaminopropyl)carbodiimide hydrochloride (EDC) or other coupling reagents published in literature. The coupling reaction can be carried out in the presence of hydroxybenzotriazol (HOBt) or the like as published in literature. Optionally, an alkaline compound can be employed to catalyze the coupling reaction, such as dimethylaminopyridine (DMAP), triethylamine, pyridine, 1,8-Diazabicyclo[5.4.0]undec-7-ene (DBU) or the ones published in literature or known by the person skilled in the art. Reactions from present disclosure can be carried out in one solvent or a mixture of solvents from acetone, dichloromethane, chloroform, ethyl acetate, ether, hexane, petroleum ether, tetrahydrofuran, N,N-dimethyl formamide or dimethyl sulphoxide or the like, which are well known in the art. The new compounds from the disclosure can be purified by liquid chromatography, crystallization, or triturating using a solvent or a mixture of solvents mentioned herein. The reaction temperature may be from about −15 to about 60° C. and optimal conditions can be chosen according to solvents used and reaction conditions.

The examples and embodiments described herein are for illustrative purposes only and various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

The compounds of the present disclosure may be prepared by the methods described below, or by modifications thereof, using readily available starting materials, reagents and conventional synthesis procedures. The following specific non-limiting examples are illustrative of the disclosure.

Example 1. Synthesis of Artesunate Trimer 1

To the solution of artesunate (0.6 g, 1.56 mmol) and triethanolamine (0.39 g, 0.26 mmol) in dry dichloromethane (10 mL) on ice-bath was added DIC (96 mg, 0.78 mmol) and DMAP (25 mg). The mixture was stirred at ambient temperature for 12 hr. The reaction mixture was filtered and chromatographed over silica gel column eluting with mixtures of hexane-EtOAC from 90:10 to 50:50. The desired fractions were combined according to TLC similarities and concentrated to yield 0.52 g of compound 1 as colorless foam. $^1$HNMR (CDCl$_3$, 360 MHz): δ 5.78 (d, J=9.7 Hz, 3H), 5.43 (s, 3H), 2.83 (t, J=5.7 Hz, 6H), 2.75-2.50 (m, 15H), 2.36 (dd, J=13.9, 3.9 Hz, 3H), 2.07-1.98 (m, 3H), 1.94-1.85 (m, 3H), 1.84-1.67 (m, 6H), 1.68-1.53 (m, 9H), 1.52-1.24 (m, 21H), 1.05-0.94 (m, 3H), 0.95 (d, J=5.7 Hz, 9H), 0.85 (d, J=7.2 Hz, 9H). MS (ESI): m/z 1249 (M+1).

Example 2. Synthesis of Dihydroartemisinin Trimer 2

To the solution of dihydroartemisinin (1.2 g, 4.2 mmol) and nitrilotriacetic acid (0.27 g, 1.4 mmol) in dry dichloromethane (10 mL) on ice-bath was added DIC (66 mL, 4.2 mmol) and DMAP (50 mg). The mixture was then stirred at ambient temperature for 12 hr. The reaction mixture was filtered and chromatographed over silica gel column eluting with mixtures of hexane-EtOAC from 90:10 to 50:50. The desired fractions were combined according to TLC similarities and concentrated to yield 0.92 g of compound 2 as colorless foam. $^1$HNMR (CDCl$_3$, 360 MHz): δ 5.80 (d, J=9.7 Hz, 3H), 5.42 (s, 3H), 3.85-3.66 (m, 6H), 2.60-2.47 (m, 3H), 2.35 (dd, J=14.1, 4.0,Hz, 3H), 2.08-1.95 (m, 3H), 1.92-1.80 (m, 3H), 1.82-1.57 (m, 9H), 1.55-1.24 (m, a singlet at 1.42, 21), 1.08-0.94 (m, 3H), 0.95 (d, J=5.7, 9H), 0.83 (d, J=7.2 Hz, 9H). MS (ESI): m/z 991 (M+1).

Example 3. Synthesis of Artesunate Trimer 3

To the solution of artesunate (1 g, 2.6 mmol) and glycerol (80 mg, 0.86 mmol) in dry dichloromethane (15 mL) on ice-bath was added DIC (0.42 mL, 2.6 mmol) and DMAP (32 mg). The mixture was then stirred at ambient temperature for 12 hr and filtered. The reaction mixture was chromatographed over silica gel column eluting with hexane-EtOAc from 95:5 to 85:15. The desired fractions were combined based on TLC similarities and concentrated to yield 0.96 g of compound 3 as colorless foam. $^1$HNMR (CDCl$_3$, 360 MHz): δ 5.78 (d, J=9.4 Hz, 3H), 5.43 (s, 3H), 5.30-5.23 (m, 1H), 4.35-4.28 (m, 2H), 4.22-4.14 (m, 2H), 2.76-2.50 (m, 15H), 2.36 (dd, J=14.0, 4.0 HZ, 3H), 2.04-1.98 (m, 3H), 1.93-1.85 (m, 3H), 1.82-1.64 (m, 6H), 1.65-1.57 (m, 3H), 1.50-1.17 (m, a singlet at 1.42, 21H), 1.06-0.97 (m, 3H), 0.95 (d, J=5.8 Hz, 9H), 0.85 (d, J=6.9 Hz, 9H). MS (ESI): m/z 1192 (M+1). MS (ESI): m/z 1192 (M+1).

Example 4. Synthesis of Artesunate Trimer 4

To the solution of artesunate (1 g, 2.63 mmol) and 2-amino-1,3-propandiol (0.12 g, 1.3 mmol) in dry dichloromethane and dry DMF (15 mL) on ice-bath was added EDC (0.75 g, 3.9 mmol) and DMAP (12 mg). The mixture was stirred at ambient temperature for 12 hr and filtered. The mixture was chromatographed over silica gel column eluting with hexane-EtOAc from 95:5 to 80:20. The desired fractions were combined based on TLC similarities and concentrated to yield 0.89 g of compound 4 as colorless foam. $^1$HNMR (CDCl$_3$, 900 MHz): δ 6.38 (m, 1H), 5.81-5.75 (m, 3H), 5.48-5.43 (m, 3H), 4.42 (m, 1H), 4.28-4.16 (m, 4H), 2.82-2.50 (m, 15), 2.37 (dd, J=13.3, 3.7 Hz, 3H), 2.04-1.99 (m, 3H), 1.93-1.87 (m, 3H), 1.81-1.71 (m, 6H), 1.64-1.60 (m, 3H), 1.52-1.25 (m, a singlet at 1.42, 21H), 1.07-0.98 (m, 3H), 0.97 (d, J=5.2 Hz, 9H), 0.86 (d, J=6.7 Hz, 9H). MS(EMI): m/z 1177 (M+1)

Example 5. Synthesis of Artesunate Trimer 5

To the solution of artesunate (1 g, 2.6 mmol) and pentaerythritol (0.118 g, 0.87 mmol) in dry dichloromethane (15 mL) on ice-bath was added DIC (0.42 mL, 2.6 mmol) and DMAP (36 mg). The mixture was stirred at ambient temperature for 36 hr. The reaction mixture was filtered and chromatographed over silica gel column eluting with mixtures of hexane-EtOAC from 90:10 to 50:50. The desired fractions were combined according to TLC similarities and concentrated to yield 0.51 g of compound 5 as colorless foam. MS (ESI): m/z 1236 (M+1).

Example 6. Synthesis of Artesunate Tetramer 6

To the solution of artesunate (1 g, 2.6 mmol) and pentaerythritol (0.88 g, 0.65 mmol) in dry dichloromethane (15 mL) on ice-bath was added DIC (0.42 mL, 2.6 mmol) and DMAP (33 mg). The reaction was stirred at ambient temperature for 12 hr and then filtered. The reaction mixture was chromatographed over silica gel column eluting with solvents of hexane-EtOAc from 90:10 to 75:25. The desired fractions were combined according to TLC similarities and concentrated to yield 0.63 g of compound 6 as colorless foam. $^1$HNMR (CDCl$_3$, 360 MHz): δ 5.76 (d, J=9.9 Hz, 4H), 5.43 (s, 4H), 4.11 (s, 8H), 2.68-2.50 (m, 20H), 2.35 (dd, J=14.0, 3.9, 4H), 2.04-1.96 (m, 4H), 1.93-1.80 (m, 4H), 1.81-1.67 (m, 8H), 1.64-1.57 (m, 4H), 1.51-1.21 (m, a singlet at 1.42, 28H), 1.05-0.94 (m, 4H), 0.95 (d, J=5.7 Hz, 12H), 0.84 (d, J=7.2 Hz, 12H). MS (ESI): m/z 1602 (M+1).

Example 7. Synthesis of Artesunate Trimer 7

To a solution of artesunate (1 g, 2.6 mmol) and N-Boc-tris(hydroxymethyl)aminomethane (0.19 g, 0.87 mmol) in dry dichloromethane (10 mL) on ice-bath was added DIC (0.40 mL, 2.6 mmol) and DMAP (50 mg). The mixture was then stirred at ambient temperature for 12 hr. The reaction mixture was filtered and chromatographed over silica gel column eluting with mixtures of hexane-EtOAC from 90:10 to 50:50. The desired fractions were combined according to TLC similarities and concentrated to yield 1.12 g of compound 7 as colorless foam. $^1$HNMR (CDCl$_3$, 360 MHz): δ 5.78 (d, J=9.7 Hz, 3H), 5.43 (s, 3H), 5.10 (br, 1H), 4.34 (s, 6H), 2.71-2.65 (m, 12H), 2.66-2.50 (m, 3H), 2.37 (dd, J=14.2, 3.9 Hz, 3H), 2.06-1.97. (m, 3H), 1.92-1.85 (m, 3H), 1.78-1.65 (m, 6H), 1.64-1.57 (m, a singlet at 1.63, 12H), 1.48-1.22 (m, a singlet at 1.42, 21H), 1.11-0.94 (m, 3H), 0.95 (d, J=6.1 Hz, 9H), 0.84 (d, J=6.8 Hz, 9H). MS (ESI): m/z 1321 (M+1).

Example 8. Synthesis of Artesunate Trimer 8

To the solution of artesunate (1 g, 2.6 mmol) and N-Cbz-tris(hydroxymethyl)aminomethane (0.22 g, 0.87 mmol) in dry dichloromethane (15 mL) on ice-bath was added DIC (0.41 mL, 2.6 mmol) and DMAP (32 mg). The mixture was stirred at ambient temperature for 12 hr and then filtered. The reaction mixture was chromatographed over silica gel column eluting with mixtures of hexane-EtOAC from 95:5 to 85:15. The desired fractions were combined according to TLC similarities and concentrated to yield 1.2 g of compound 8 as colorless foam. $^1$HNMR (CDCl$_3$, 360 MHz): δ 7.41-7.29 (m, 5H), 5.77 (d, J=10.0 Hz, 3H), 5.66 (b, 1H), 5.37 (s, 3H), 5.08-5.05 (m, 2H), 4.42-4.31 (m, 6H), 2.72-2.62 (m, 12H), 2.58-2.48 (m, 3H), 2.36 (dd, J=13.7, 3.9 Hz, 3H), 2.04-1.97 (m, 3H), 1.92-1.83 (m, 3H), 1.75-1.65 (m, 6H), 1.65-1.55 (m, 3H), 1.48-1.21 (m, a singlet at 1.42, 21H), 1.05-0.93 (m, 3H), 0.93 (d, J=5.0 Hz, 9H), 0.82 (d, J=7.2 Hz, 9H). MS (ESI): m/z 1355 (M+1).

Example 9. Synthesis of Artesunate Trimer 9

To the solution of artesunate (1 g, 2.6 mmol) and N-acetyl-tris(hydroxymethyl)aminomethane (0.14 g, 0.87 mmol) in dry dichloromethane (10 mL) on ice-bath was added DIC (0.41 mL, 2.6 mmol) and DMAP (25 mg). The mixture was stirred at room temperature for 12 hr and then filtered. The reaction mixture was chromatographed over silica gel column eluting with mixtures of hexane-EtOAc from 90:10 to 85:15. The desired fractions were combined according to TLC similarities and concentrated to yield 1.12 g of compound 9 as colorless foam. $^1$HNMR (CDCl$_3$, 360 MHz): δ 6.38 (s, 1H), 5.76 (d, J=9.7 Hz, 3H), 5.43 (s, 3H), 4.41-4.33 (m, 6H), 2.72-2.60 (m, 12H), 2.60-2.51 (m, 3H), 2.34 (dd, J=13.5, 3.8 Hz, 3H), 2.03-1.98 (m, a singlet at 2.02, 6H), 1.92-1.81 (m, 3H), 1.78-1.65 (m, 6H), 1.63-1.55 (m, 3H), 1.52-1.18 (m, a singlet at 1.42, 21H), 1.05-0.93 (m, 3H), 0.94 (d, J=5.3 Hz, 9H), 0.83 (d, J=6.9 Hz, 9H). MS(ESI): m/z 1263 (M+1).

Example 10. Synthesis of Artesunate Trimer 10

To the solution of artesunate (1 g, 2.6 mmol) and N-Fmoc-tris(hydroxymethyl)aminomethane (0.29 g, 0.87 mmol) in the mixture of dry dichloromethane and dry DMF (15 mL) on ice-bath was added DCI (0.41 g, 2.6 mmol) and DMAP (35 mg). The mixture was stirred at ambient temperature for 12 hr. The reaction was filtered and chromatographed over silica gel column eluting with hexane-EtOAc from 90:10 to 30:70. Desired fractions were combined according to TLC similarities and concentrated to yield 0.89 g of compound 10 as colorless foam. (CDCl$_3$, 360 MHz): δ 7.81-7.63 (m, 4H), 7.45-7.28 (m, 4H), 5.77 (d, J=10.1 Hz, 3H), 5.63 (b, 1H), 5.35 (s, 3H), 4.42 (m, 6H), 4.24 (m, 2H), 2.81-2.64 (m, 12H), 2.64-2.50 (m, 3H), 2.35 (dd, J=13.5, 3.4 Hz, 3H), 2.09-1.99 (m, 3H), 1.91-1.82 (m, 3H), 1.81-1.21 (m, a singlet at 1.42, 30H), 1.01-0.92 (m, 12H), 0.83 (d, J=7.2 Hz, 9H). MS (ESI): m/z 1442 (M+1).

Example 11. Synthesis of Artesunate Trimer 11

To the solution of artesunate (1 g, 2.6 mmol) and N-formyl-tris(hydroxymethyl)aminomethane (0.5 g, 0.87 mmol) in the mixture of dry dichloromethane and dry DMF (15 mL) on ice-bath was added EDC HCl (0.5 g, 2.6 mmol) and DMAP (14 mg). The mixture was stirred at ambient temperature for 12. The reaction was quenched with water and extracted with EtOAc. The EtOAc extraction was washed with brine, dried over NaSO4 and concentrated under reduced pressure. The residue was chromatographed over silica gel column eluting with hexane-EtOAc from 90:10 to 30:70. Desired fractions were combined according to TLC similarities and concentrated to yield 0.88 g of compound 11 as colorless foam. $^1$HNMR (CDCl$_3$, 900 MHz): δ 8.06 (S, 1H), 6.61 (s, 1H), 5.76 (d, J=9.4 Hz, 3H), 5.45 (s, 3H), 4.39-4.46 (m, 6H), 2.78-2.65 (m, 12H), 2.60-2.53 (m, 3H), 2.34 (dd, J=13.3, 3.7 Hz, 3H), 2.04 (s, 3H), 1.93-1.84 (m, 3H), 1.81-1.71 (m, 6H), 1.65-1.60 (m, 3H), 1.50-1.23 (m, a singlet at 1.43, 21H), 1.06-9.98 (m, 3H), 0.96 (d, J=5.2 Hz, 9H), 0.83 (d, J=6.7 Hz, 9H). MS(EMI): m/z 1249 (M+1).

Example 12. Synthesis of Artesunate Trimer 12

To the solution of artesunate (1 g, 2.63 mmol) and N-trifluroacetyl-tris(hydroxymethyl)aminomethane (0.2 g, 0.9 mmol) in a mixture of dry dichloromethane and dry DMF (15 mL) on ice-bath was added EDC HCl (0.53 g, 2.63 mmol) and DMAP (14 mg). The mixture was stirred at ambient temperature for 12. Workup and purification is similar to Example 11 to yield 0.59 g of compound 12 as colorless foam. ¹HNMR (CDCl₃, 900 MHz): δ 6.44 (s, 1H), 5.78 (d, J=9.4 Hz, 3H), 5.46 (s, 3H), 4.43-4.33 (m, 6H), 2.78-2.56 (m, 15H), 2.37 (dd, J=13.3, 3.7 Hz, 3H), 2.08-2.02 (m, 3H), 1.93-1.86 (m, 3H), 1.82-1.69 (m, 6H), 1.63-1.59 (m, 3H), 1.54-1.26 (m, a singlet at 1.42, 21H), 1.03-0.98 (m, 3H), 0.97 (d, J=5.2 Hz, 9H), 0.86 (d, J=6.7 Hz, 9H). MS(EMI): m/z 1317 (M+1).

Example 13. Synthesis of Artesunate Tetramer 13

To the solution of artesunate (1 g, 2.6 mmol) and tris(hydroxymethyl)aminomethane (0.79 g, 0.65 mmol) in dry dichloromethane (15 mL) on ice-bath was added DIC (0.41 mL, 2.6 mmol) and DMAP (25 mg). The mixture was then stirred at ambient temperature for 12 hr. The reaction mixture was filtered and chromatographed over silica gel column eluting with mixtures of hexane-EtOAc from 90:10 to 75:25. The desired fractions were combined according to TLC similarities and concentrated to yield 0.62 g of compound 13 as colorless foam. ¹HNMR (CDCl₃, 360 MHz): δ 6.41 (s, 1H), 5.77-5.74 (m, J=9.7 Hz, 4H), 5.44 (s, 3H), 5.41 (s, 1H), 4.40-4.32 (m, 6H), 2.78-2.50 (m, 20H), 2.35 (dd, J=13.3, 3.8 Hz, 4H), 2.10-2.01 (m, 4H), 1.91-1.81 (m, 4H), 1.78-1.68 (m, 8H), 1.67-1.57 (m, 4H), 1.51-1.22 (m, a singlet at 1.42, 28H), 1.05-0.94 (m, 4), 0.95 (d, J=5.4 Hz, 12H), 0.84 (d, J=6.8 Hz, 12H). MS (ESI): m/z 1587 (M+1).

Example 14. Synthesis of Dihydroartemisinin Trimer 14

To the solution of dihydroartemisinin (0.58 g, 2.0 mmol) and tricarbollylic acid (0.12 g, 0.68 mmol) in dry dichloromethane (15 mL) on ice-bath was added DIC (0.31 mL, 2.0 mmol) and DMAP (70 mg). The mixture was stirred at ambient temperature for 12 hr and filtered. The reaction mixture was chromatographed over silica gel column eluting with solvents of hexane-EtOAc from 90:10 to 30:70. The desired fractions were combined according to TLC similarities and concentrated to yield 0.31 g of compound 14 as colorless foam. (CDCl₃, 360 MHz): δ 5.68-5.82 (m, 3H), 5.45-5.36 (m, 3H), 3.42-3.31 (m, 1H), 2.93-2.85 (m, 4H), 2.62-2.51 (m, 3H), 2.36 (dd, J=13.7, 3.9 Hz, 3H), 2.06-1.94 (m, 3H), 1.92-1.82 (m, 3H), 1.81-1.66 (m, 6H), 1.65-1.58 (m, 3H), 1.57-1.22 (m, 21H), 1.07-0.92 (m, 12H), 0.87-0.81 (m, 9H). MS (ESI): m/z 976 (M+1).

Example 15. Synthesis of Artesunate Tetramer 15

To the solution of artesunate (1 g, 2.6 mmol) and N,N,N',N'-tetrakis(2-hydroxyethyl)ethylenediamine (0.154 g, 0.65 mmol) in dry dichloromethane (15 mL) on ice-bath was added DIC (0.41 mL, 2.6 mmol) and DMAP (59 mg). The mixture was then stirred at ambient temperature for 12 hr and filtered. The reaction mixture was chromatographed over silica gel column eluting with mixtures of hexane-EtOAC from 90:10 to 50:50. The desired fractions were combined according to TLC similarities and concentrated to yield 0.78 g of compound 15 as colorless foam. ¹HNMR (CDCl₃, 360 MHz): δ 5.78 (d, J=9.9 Hz, 4H), 5.43 (s, 4H), 4.12 (t, J=5.2 Hz, 8H), 2.78 (t, J=5.7 Hz, 8H), 2.74-2.50 (m, 24H), 2.36 (dd, J=14.2, 4.0 Hz, 4H), 2.07-1.97 (m, 4H), 1.94-1.85 (m, 4H), 1.83-1.68 (m, 8H), 1.65-1.58 (m, 4H), 1.50-1.19 (m, a singlet at 1.42, 28H), 1.05-0.94 (m, 4H), 0.95 (d, J=5.76 Hz, 12H), 0.85 (d, J=7.2 Hz, 12H). MS (ESI): m/z 1701 (M+1).

Example 16. Synthesis of Artesunate Trimer 16

To the solution of artesunate (1 g, 2.6 mmol) and N,N,N',N'-tetrakis(2-hydroxyethyl)ethylenediamine (0.20 mg, 0.87 mmol) in dry dichloromethane (15 mL) on ice-bath was added DIC (0.41 mL, 2.6 mmol) and DMAP (31 mg). The mixture was stirred at ambient temperature for 12 hr and filtered. The reaction mixture was chromatographed over silica gel column eluting with hexane-EtOAC from 90:10 to 30:70. The desired fractions were combined according to TLC similarities and concentrated to yield 0.35 g of compound 16 as colorless foam. ¹HNMR (CDCl₃, 360 MHz): δ 5.78 (d, J=9.7, 3H), 5.42 (s, 3H), 4.16 (t, J=6.12, 8H), 3.50 (b, 1H), 2.80-2.77 (m, 8H), 2.76-2.50 (m, 19), 2.36 (dd, J=13.8, 3.8 Hz, 3H), 2.08-1.98 (m, 3H), 1.92-1.86 (m, 3H), 1.82-1.66 (m, 6H), 1.64-1.57 (M, 3H). 1.54-1.19 (m, a singlet at 1.42, 21H), 1.09-0.97 (m, 3H), 0.95 (d, J=6.1 Hz, 9H), 0.84 (d, J=7.2 Hz, 9H). MS (ESI): m/z 1335 (M+1).

Example 17. Cytotoxicity Assays

Artesunate and dihydroartemisinin were purchased from AK Scientific (Union City, Calif.). CellTiter 96® Non-Radioactive Cell Proliferation Assay (MTT) reagent was purchased from Promega (Madison, Wis.). A549 (human lung carcinoma), HeLa (human cervical carcinoma), MOLT4 (human T-cell acute lymphoblastic leukemia) were purchased from American Type Culture Collection (Manassas, Va.) and cultured in Ham's F-12 K media supplemented with 10% FBS, 100 µg/ml of penicillin and 100 µg/ml of streptomycin. The culture was maintained at 37° C. in a humidified atmosphere of 5% CO₂ and 95% air.

Both reference and test compounds were dissolved in DMSO in a 10-concentration and 3-fold serial dilution format. 50 nl stock solution of test compounds or 25 nl of reference compounds were delivered from the source plate to the wells of 384-well cell culture plates. 25 µl of culture medium containing 2,000 corresponding cancer cells were added to the wells. The plates were incubated at 37° C. in a humidified atmosphere of 5% CO₂ and 95% air for 72 hours. 4 µl of MTT Dye Solution was added to each well and the plates were incubated at 37° C. in a CO₂ incubator for 4 hours. After incubation, the formazan was produced in the cells. 25 µl of Solubilization/Stop Solution was added to each well and the plates were incubated for another 1 hour at 37° C. in a CO₂ incubator to dissolve the formazan crystals.

The absorbance of each sample was measured at 590 nm using Envision 2104 Multilabel Reader (PerkinElmer, Santa Clara, Calif.). The cell viability was determined based on the quantification of the color intensity in each culture well. The inhibitory curves were plotted and the IC₅₀ values were calculated using GraphPad Prism 4 program based on a sigmoidal dose-response equation. The results are summarized in Table 1 and 2, respectively.

TABLE 1

Cytotoxicity of artemisinin-derived trimers on A549 cell line.

| | Inhibition (%) | | | |
|---|---|---|---|---|
| Compound | 0.1 µM | 0.25 µM | 0.5 µM | 1.0 µM |
| 1 | 10% | 14% | 20% | 47% |
| 2 | 12% | 20% | 21% | 40% |
| 7 | 12% | 14% | 21% | 40% |
| Dihydroartemisinin | ND | 5% | 10% | 20% |

TABLE 2

Cytotoxicity of artemisinin-derived trimers and tetramers on HeLa, MOLT4 and HepG2 cell lines.

| Compound | IC$_{50}$ (μm) | | |
|---|---|---|---|
| | HeLa | MOLT4 | HepG2 |
| Artesunate | 9.57 | 1.01 | 11.2 |
| Dihydroartemisinin | 9.34 | 0.68 | |
| 1 | 1.72 | 0.318 | |
| 2 | 1.14 | 0.32 | |
| 3 | 0.63 | 0.06 | 0.83 |
| 7 | 0.602 | 0.119 | |
| 9 | 0.36 | 0.066 | 0.31 |
| 13 | 14.2 | 0.15 | |
| 15 | 35.2 | 0.275 | |
| 16 | 1.11 | 0.217 | |
| 4 | | | 1.79 |
| 11 | | | 0.55 |
| 12 | | | 7.80 |
| 14 | | | 1.30 |

Data are from representative experiments of three in triplicates.

Abbreviations:
Ac: acetyl
Bn: benzyl
Boc: tert-butyloxycarbonyl
Cbz: carboxybenzyl
DHA: dihydroartemisinin
DMAP: 4-dimethylaminopyridine
DMSO: dimethyl sulfoxide
DMF: N,N-dimethyl formamide
EDC: 1-ethyl-3-(3-dimethylaminopropyl)carbodiimide hydrochloride
EtOAc: ethyl acetate
Fmoc: fluorenylmethyloxycarbonyl
MTT: 3-(4,5-dimethylthiazo-2-yl)-2,5-diphenyltetrazolium bromide
PBS: phosphate buffered saline
TLC: thin layer chromatography

The invention claimed is:

1. A compound of the general formula:

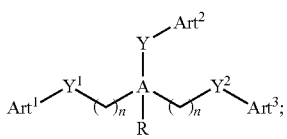

(I)

or a pharmaceutically acceptable salt thereof, wherein:
n is an integer from 0 to 6;
Art$^1$, Art$^2$ and Art$^3$ are each independently selected from:

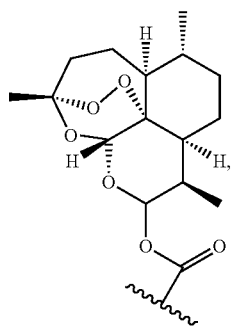

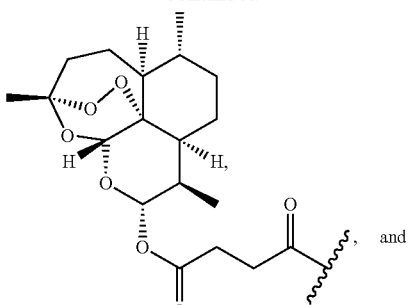

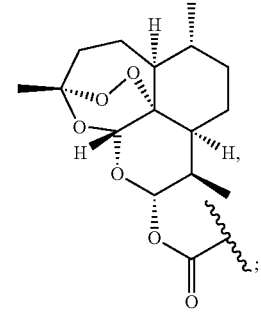

wherein A is selected from carbon, nitrogen, and

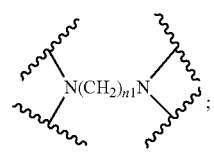

wherein n1 is an integer selected from 0 to 12;

Y, Y$^1$, and Y$^2$ are each independently selected from absent, O, NH, NR$^1$, S(O)$_m$, —(CHR$^1$)$_{n2}$—, —(CHR$^1$)$_{n2}$O—, —(CHR$^1$)$_{n2}$N—, —(CHR$^1$)$_{n2}$C(=O)—, —(CHR$^1$)$_{n2}$C(=O)O—, —(CHR$^1$)$_{n2}$C(=O)NR$^1$—, —(CHR$^1$)$_{n2}$S(O)$_m$, and —(CHR$^1$)C(=O)S—; wherein n2 is an integer selected from 0 to 6; and m is an integer selected from 0 to 2; and R is selected from absent, hydrogen, —OR$^1$, C(O)R$^1$, —C(O)OR$^1$, —(CHR$^2$)$_{n3}$R$^1$, —(CHR$^2$)$_{n3}$OR$^1$, —NR$^2$R$^1$, —(CHR$^2$)$_{n3}$NR$^2$R$^1$, —NR$^2$C(O)R$^1$, —NR$^2$C(O)OR$^1$, —NR$^2$C(O)NHR$^1$, —(CHR$^2$)$_{n3}$OC(O)R$^1$, —(CHR$^2$)$_{n3}$OC(O)OR$^1$, —N=BR$^1$, and —NHS(O)$_m$R$^1$; wherein n3 is an integer selected from 0 to 8; and m is an integer selected from 0 to 2; and wherein B is selected from N and C; R$^1$ and R$^2$ are each independently selected from hydrogen, Art$^1$, Art$^2$, Art$^3$, C$_{1-10}$alkyl, C$_{1-6}$haloalkyl, C$_{1-6}$haloalkoxyl, C$_{2-6}$alkenyl, C$_{2-6}$alkynyl, C$_{1-6}$alkylene, COOC$_{1-6}$alkyl, C$_{1-6}$alkyleneCOOH, C$_{3-12}$cycloalkyl, 3-12 membered heterocyclyl, C$_{6-12}$aryl, and 5-12 membered heteroaryl;

wherein each C$_{1-10}$alkyl, C$_{2-6}$alkenyl, C$_{2-6}$alkynyl, C$_{1-6}$alkyleneCOOC$_{1-6}$alkyl, C$_{1-6}$alkyleneCOOH, C$_{6-12}$aryl, 3-12 membered heterocyclyl, and 5-12 membered heteroaryl of R$^1$ and R$^2$ is independently optionally substituted with one to 10 groups selected from halo, hydroxyl, amino, cyano, C$_{1-6}$alkyl, C$_{1-6}$haloalkyl, C$_{1-6}$alkoxyl, C$_{1-6}$haloalkyl, C$_{3-6}$cycloalkyl, and 3-6 membered heterocyclyl.

2. A compound, or a pharmaceutically acceptable salt thereof, wherein the compound is selected from:
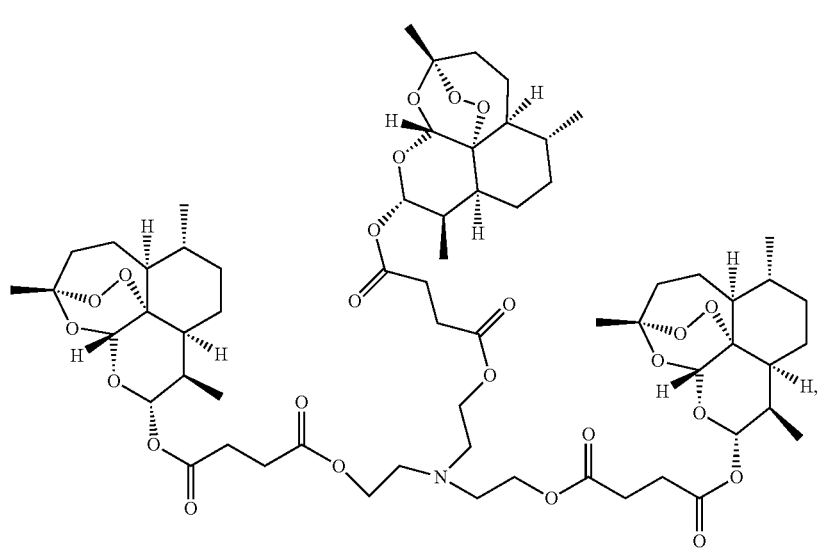
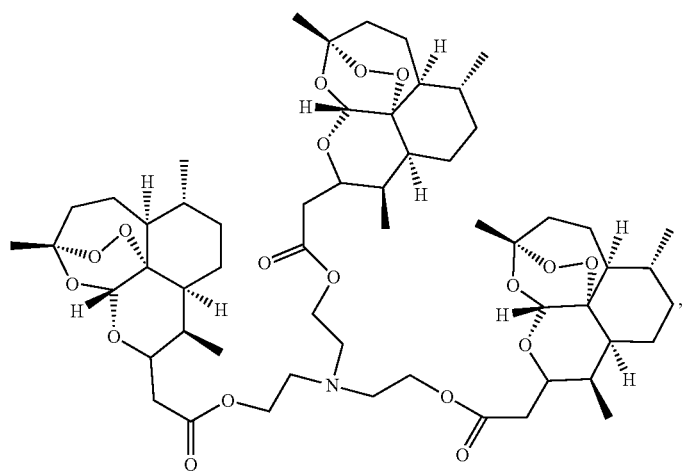
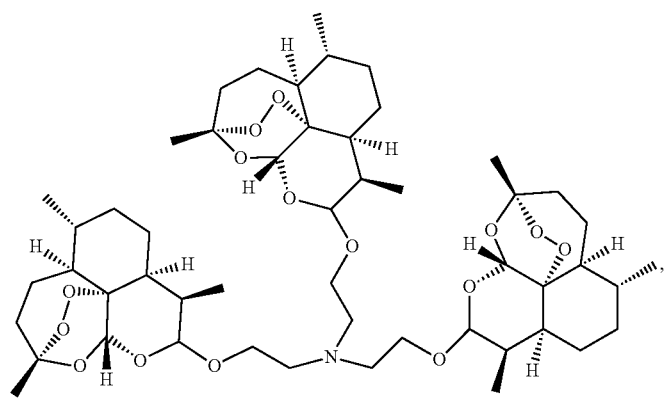

-continued
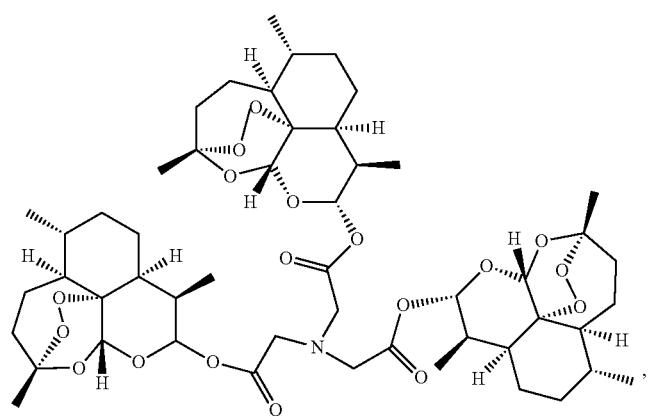
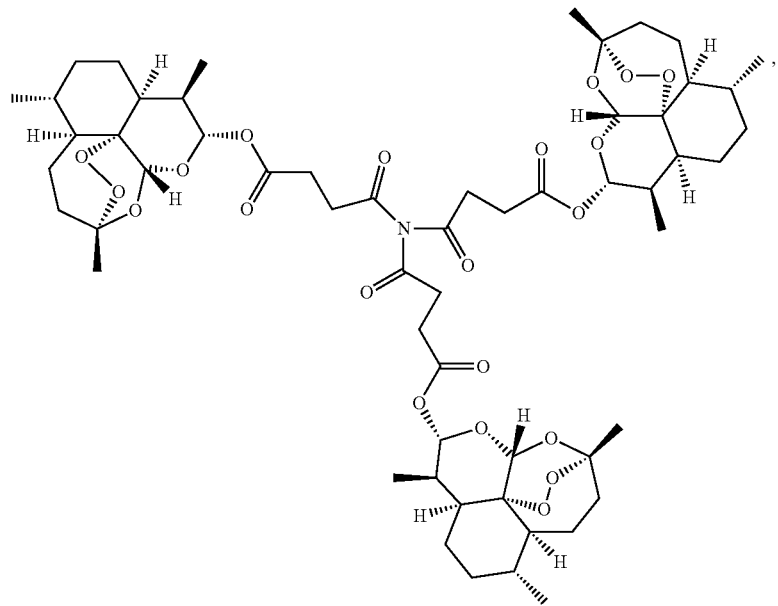
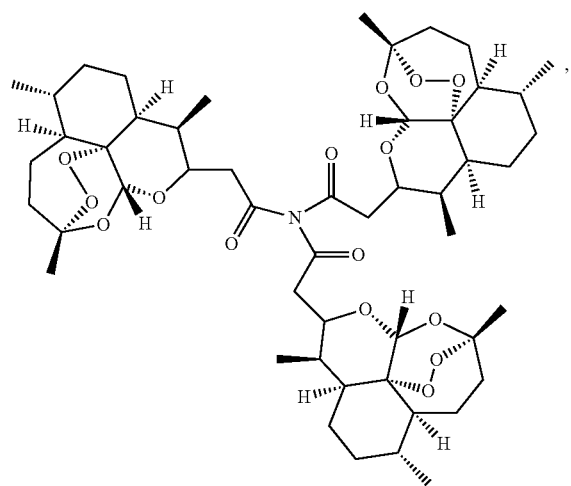

-continued
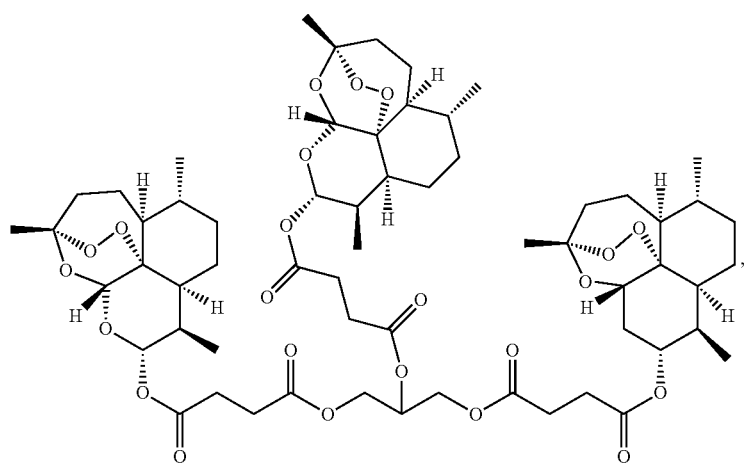
3
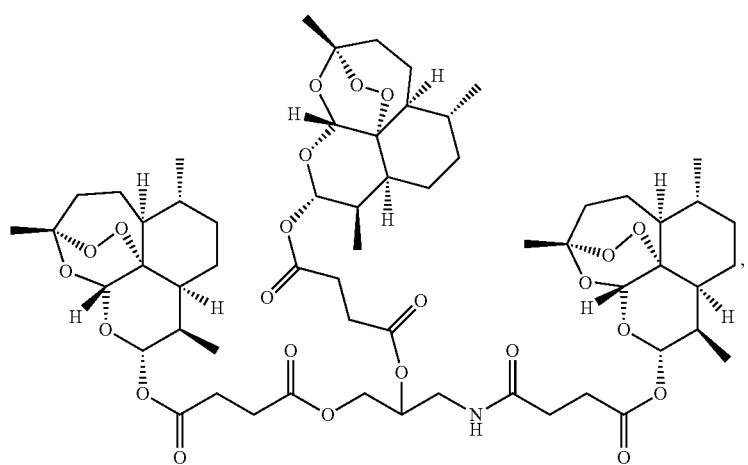
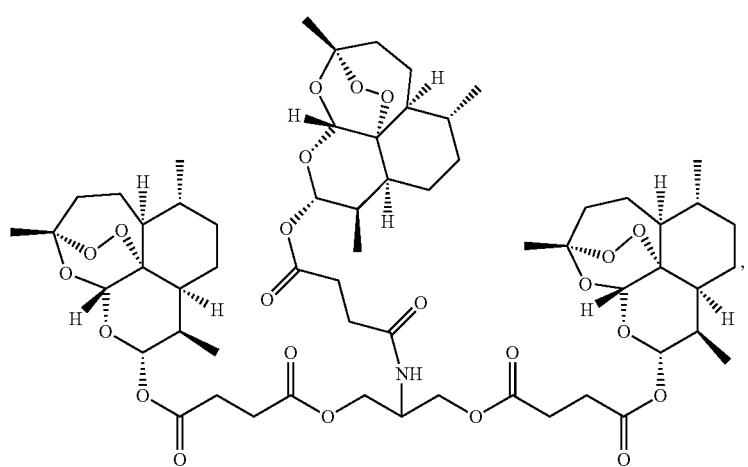
4

-continued
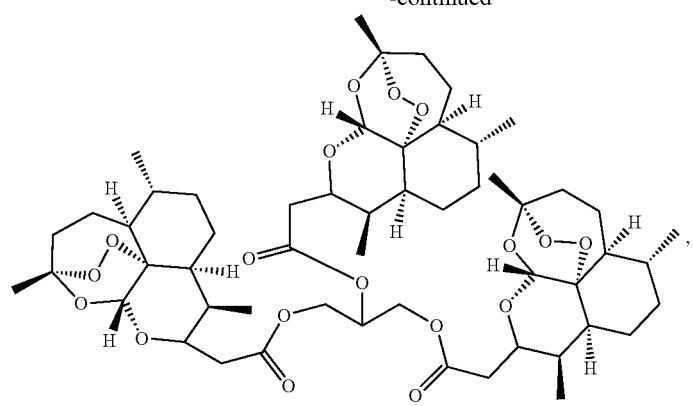
,
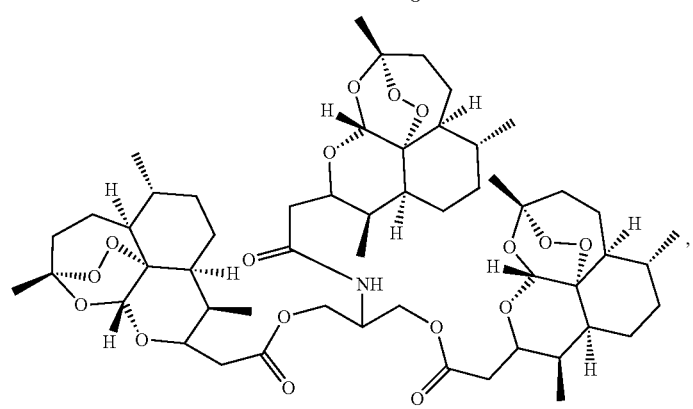
,
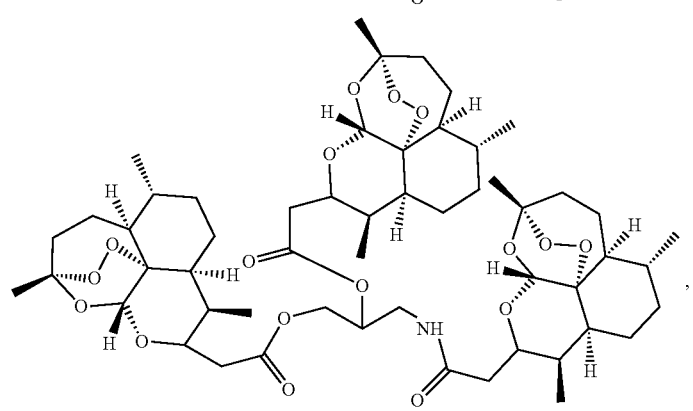
,
5
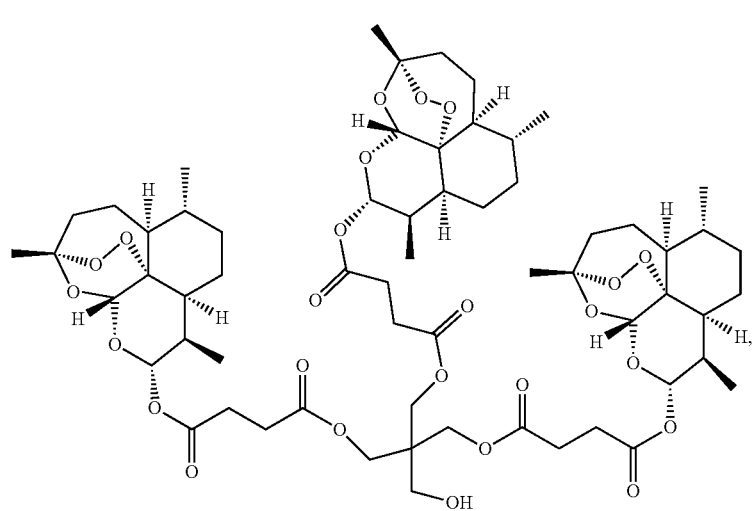

-continued
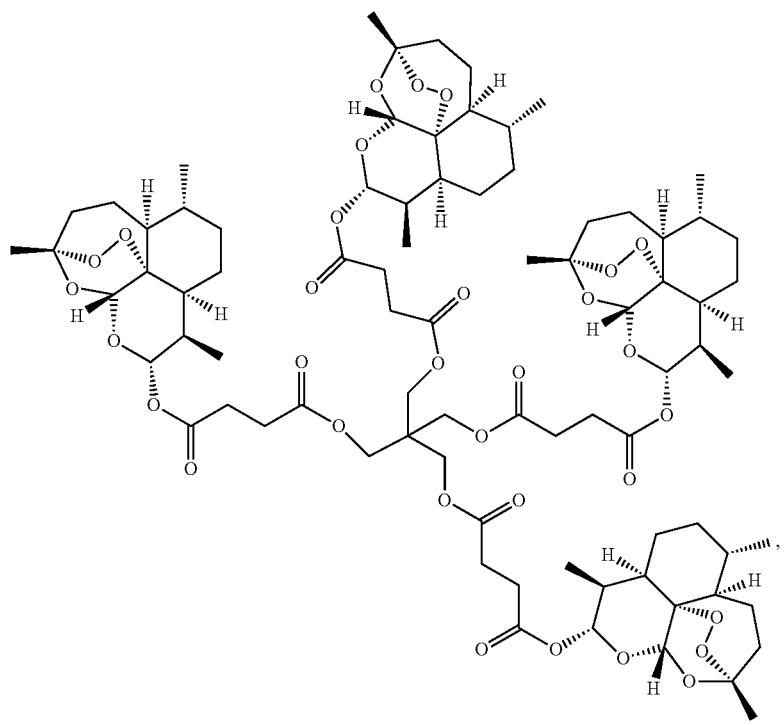
6
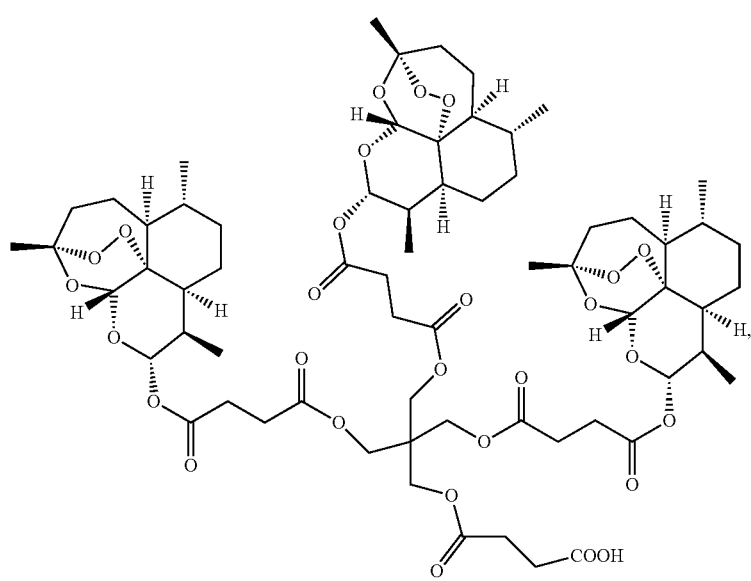

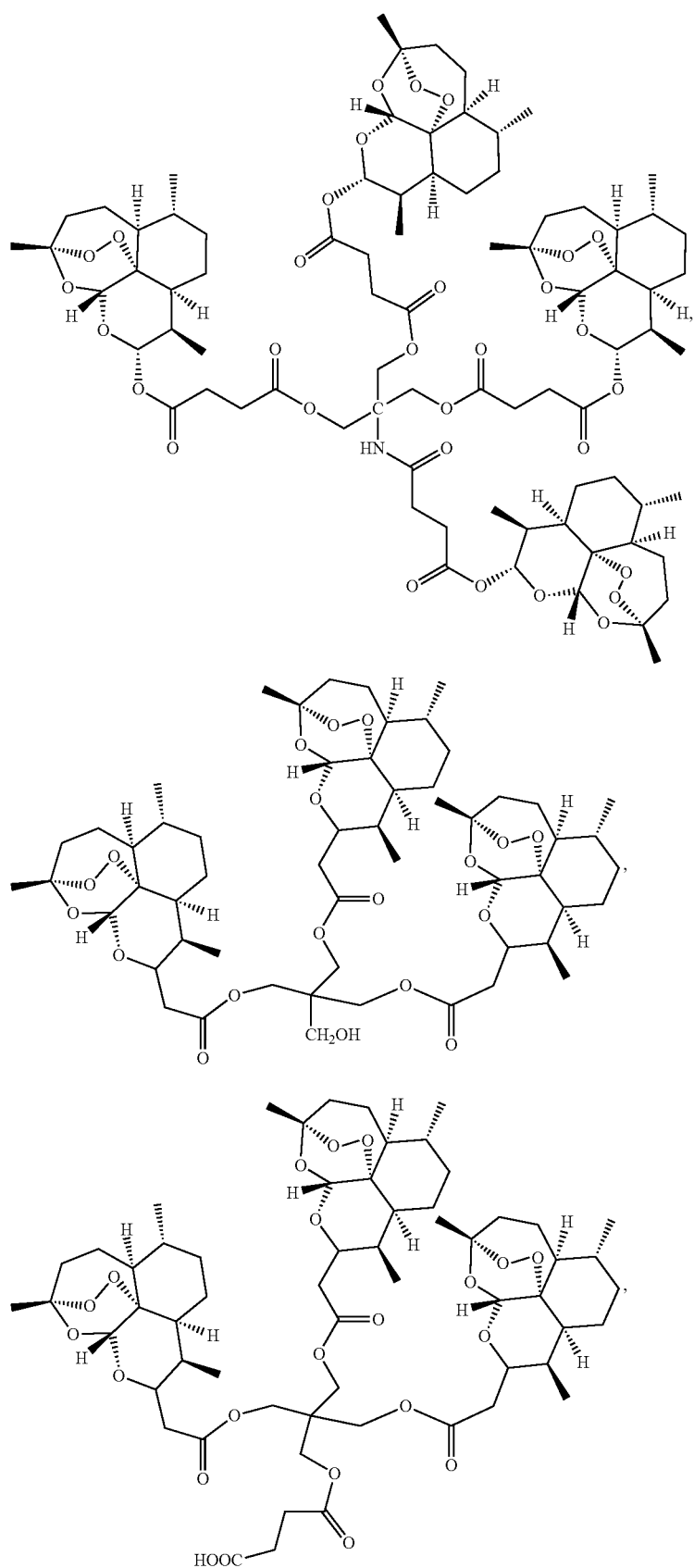

-continued
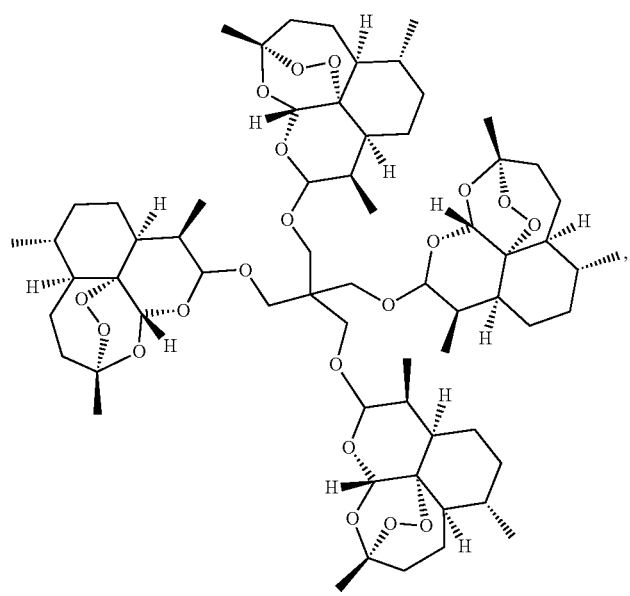
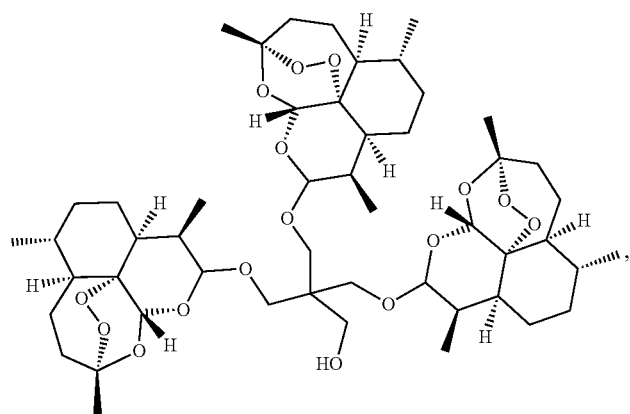
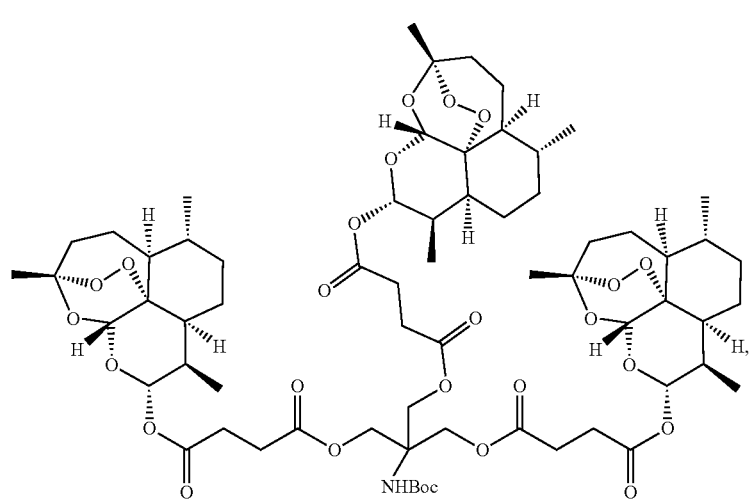

-continued
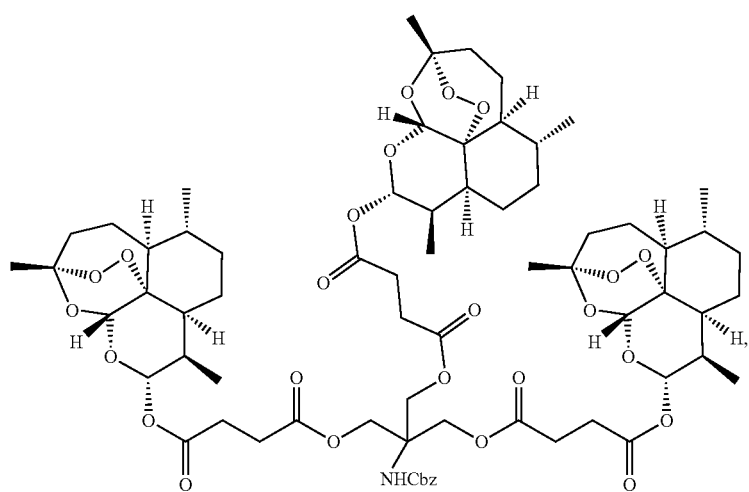
8
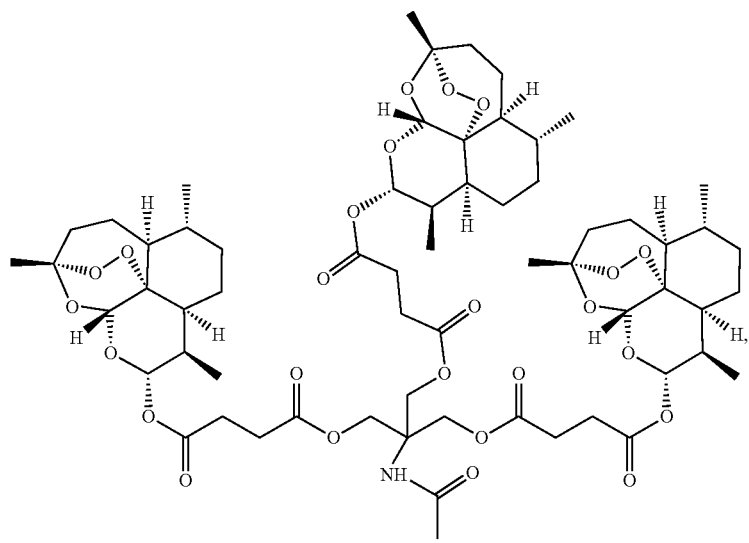
9
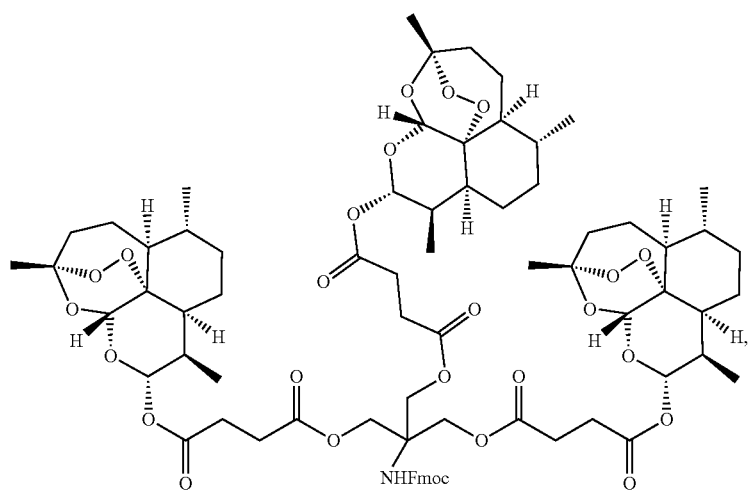
10

-continued
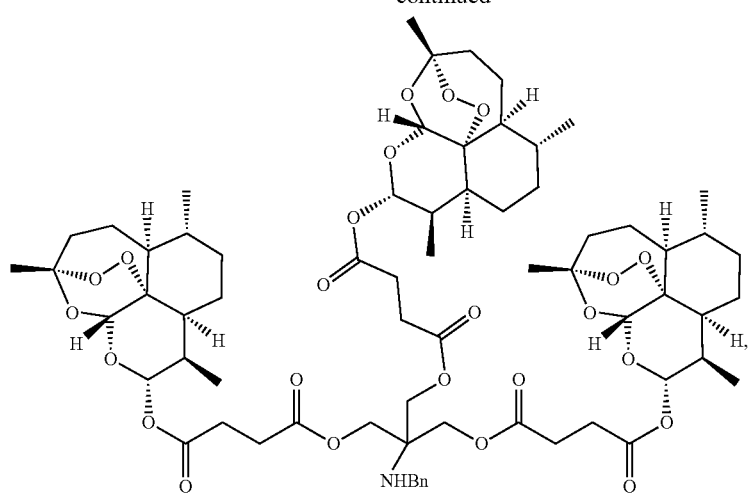
11
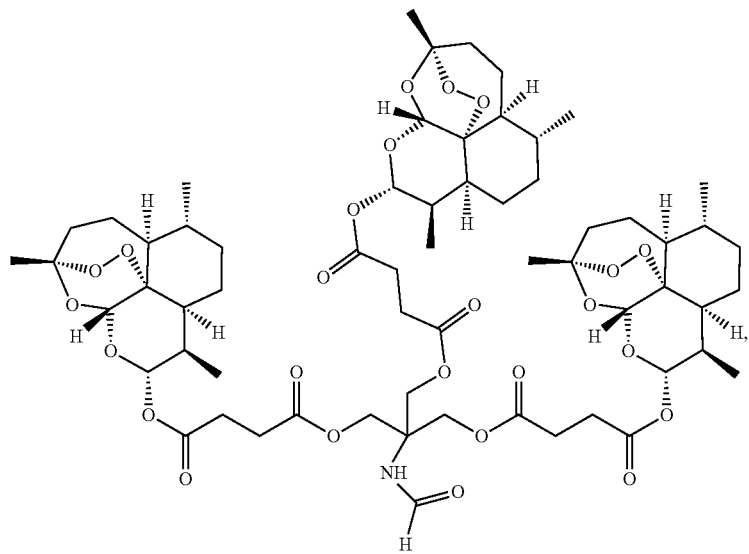
12
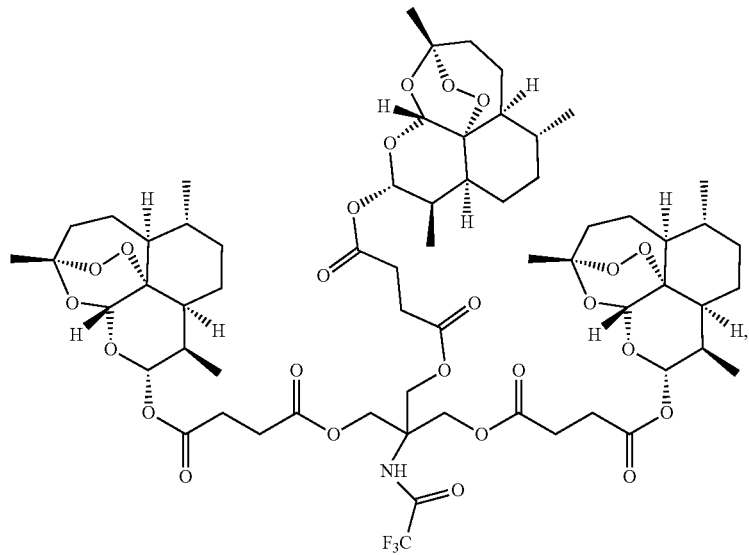

-continued
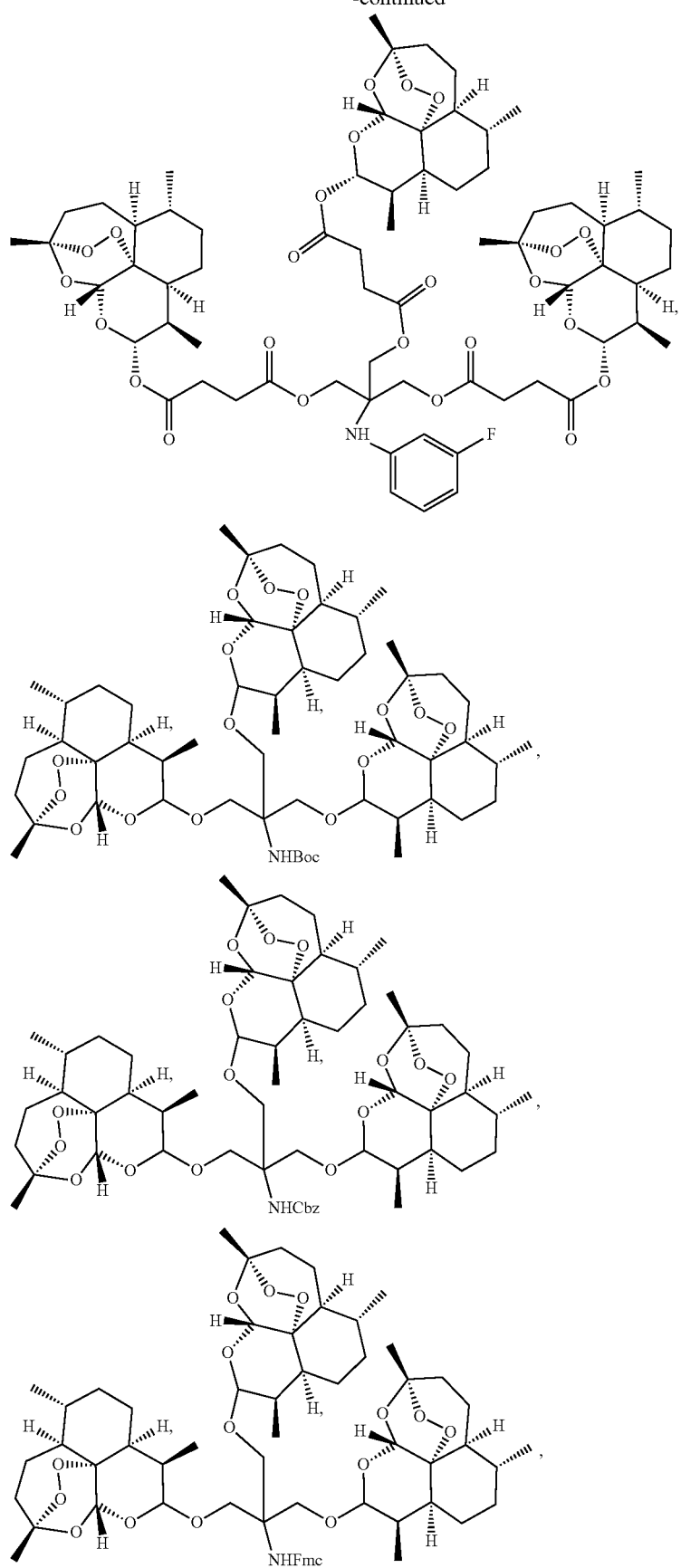

-continued
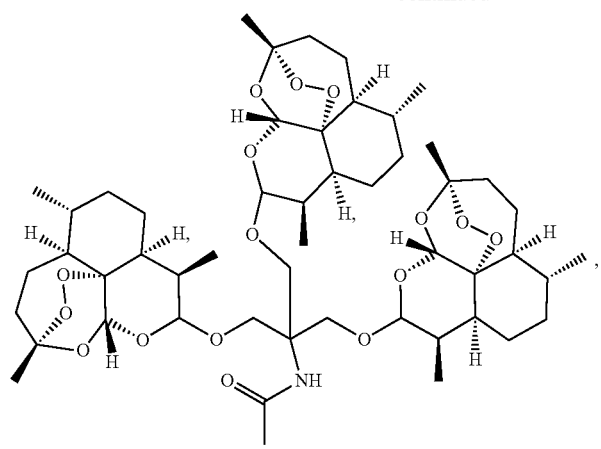
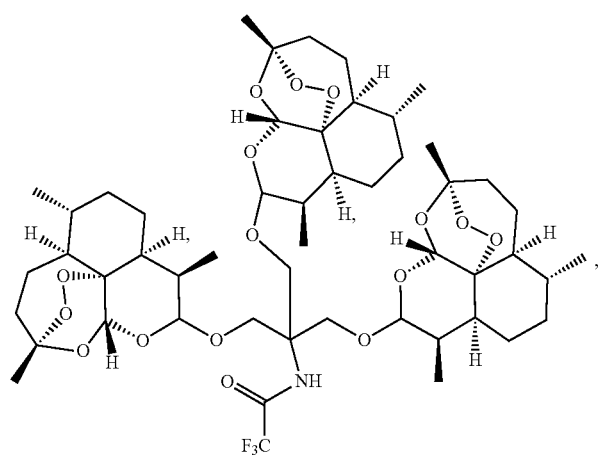
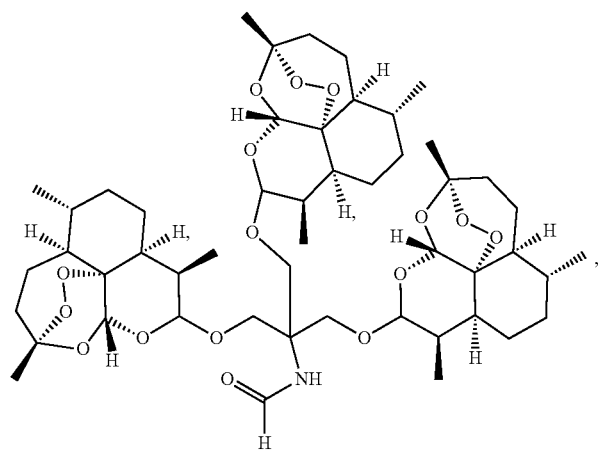

-continued
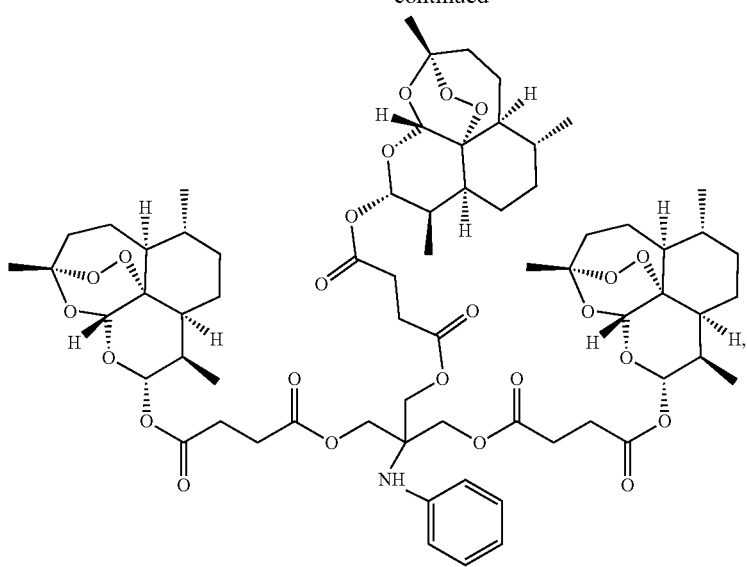
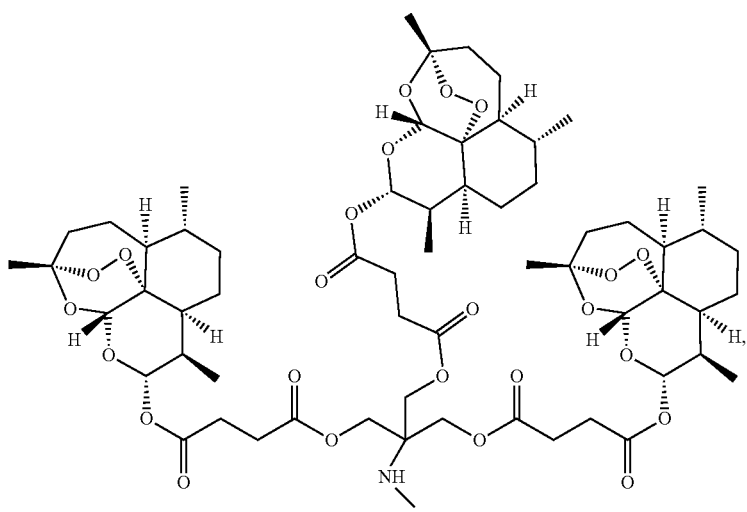
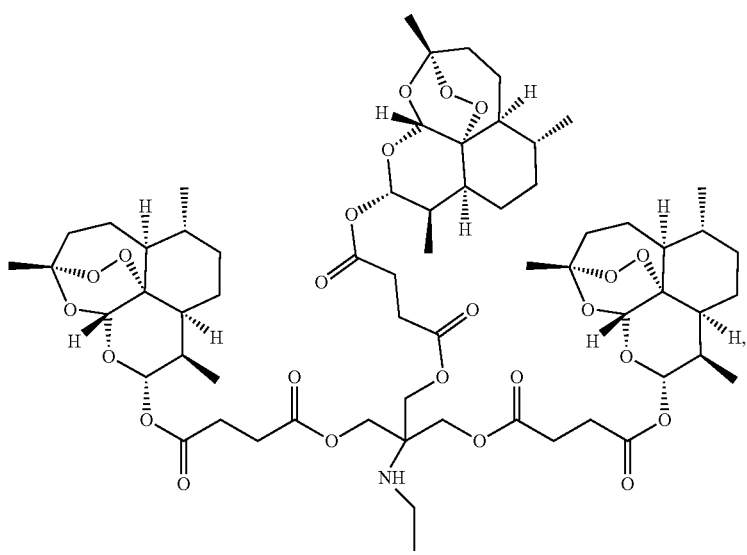

-continued
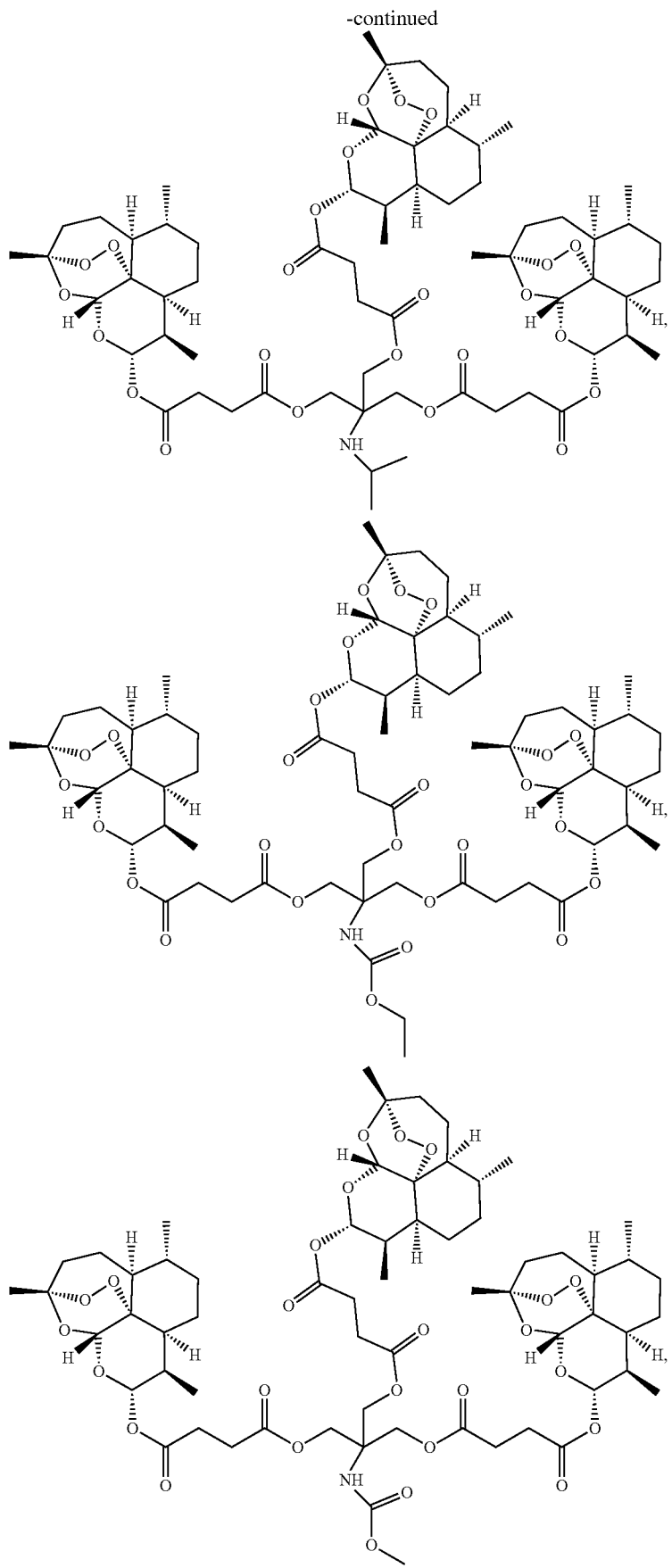

-continued
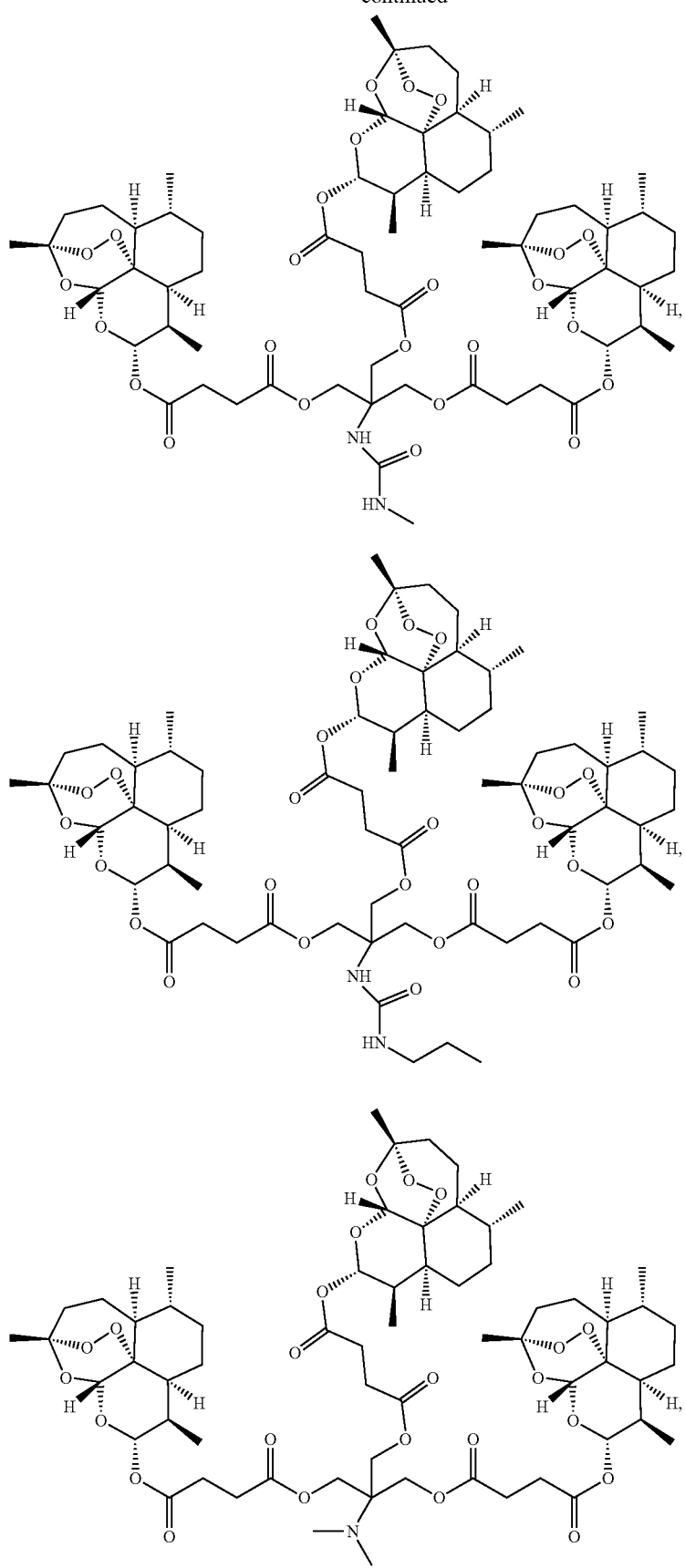

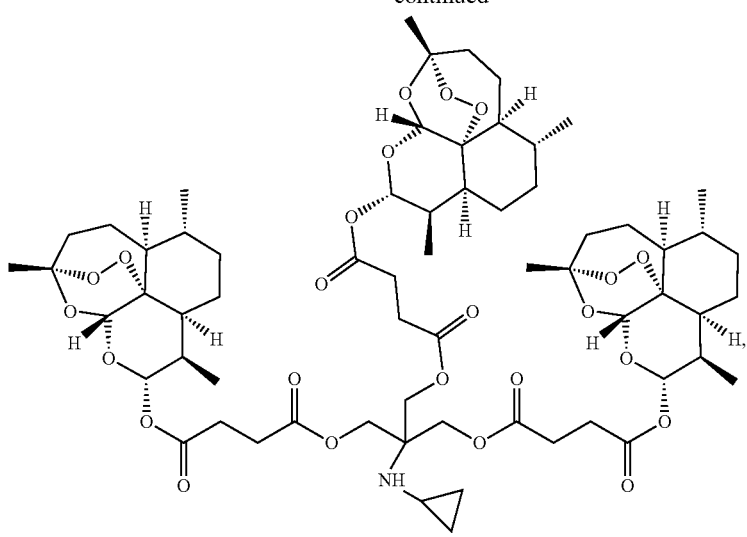
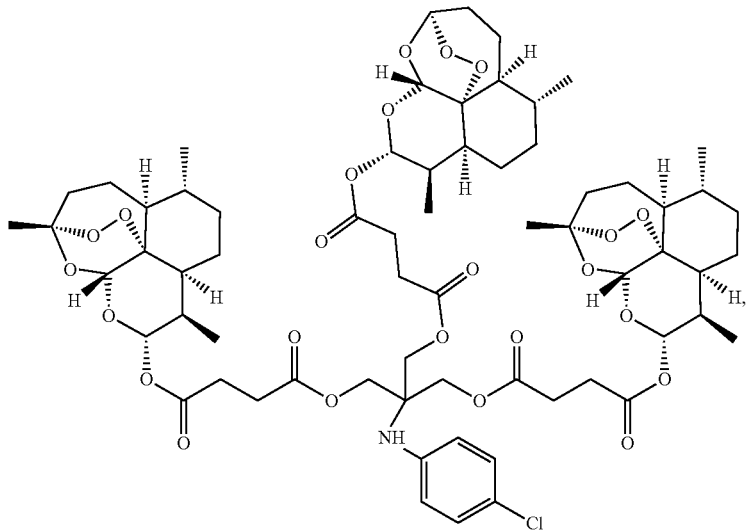
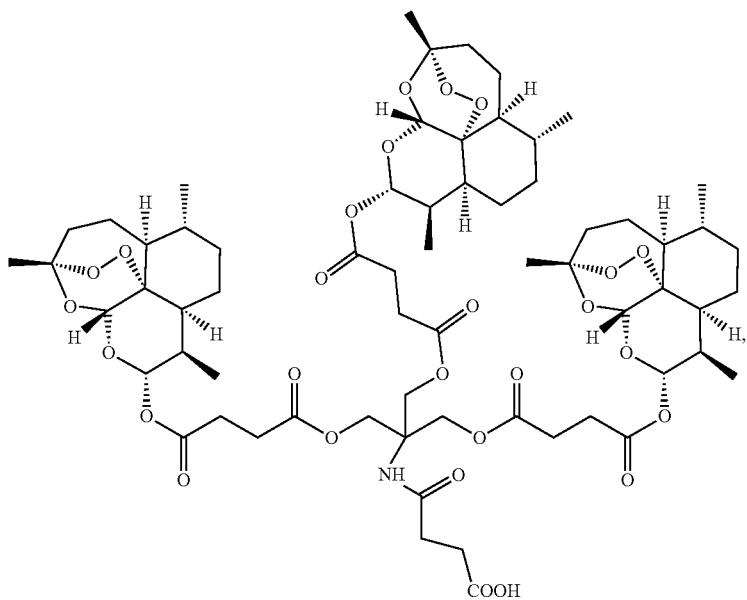

-continued
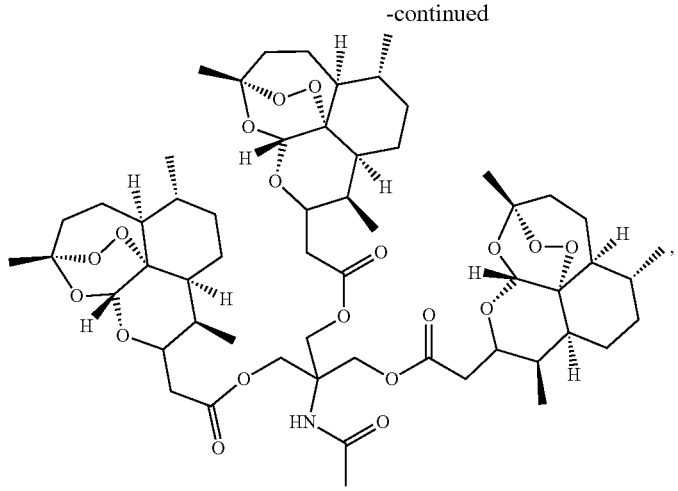
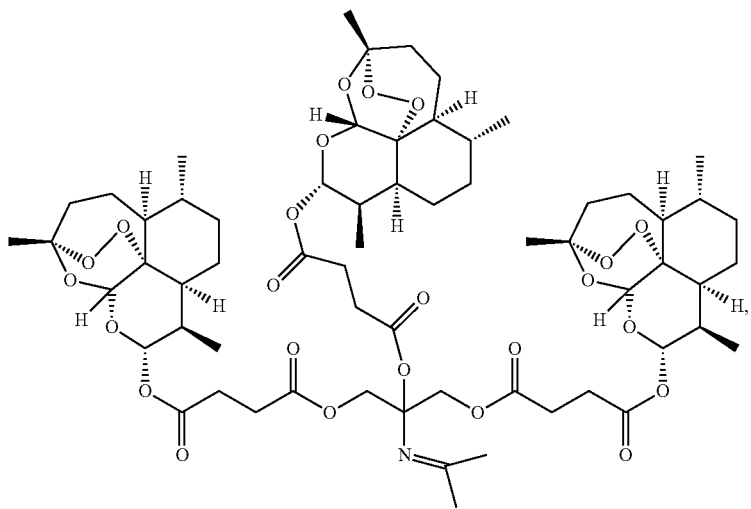
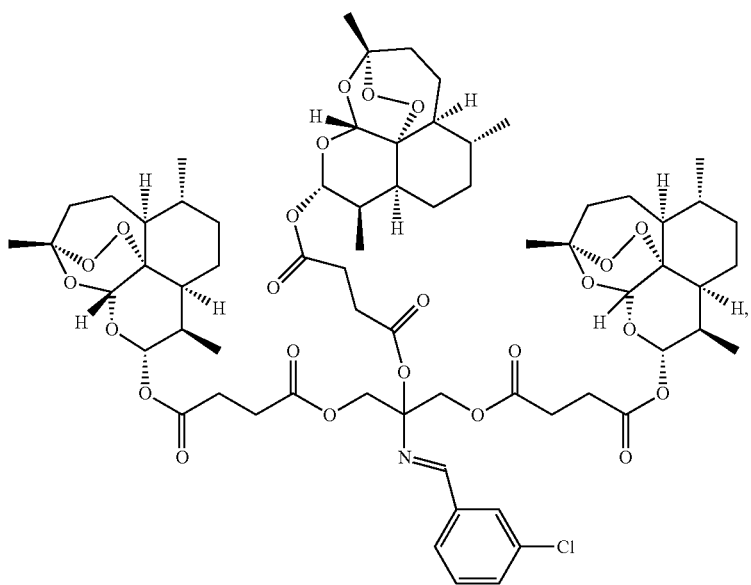

-continued
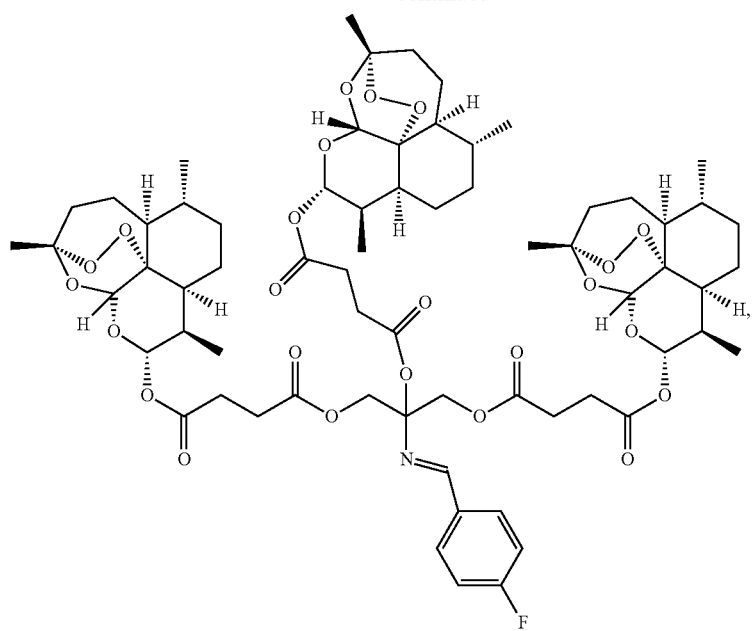
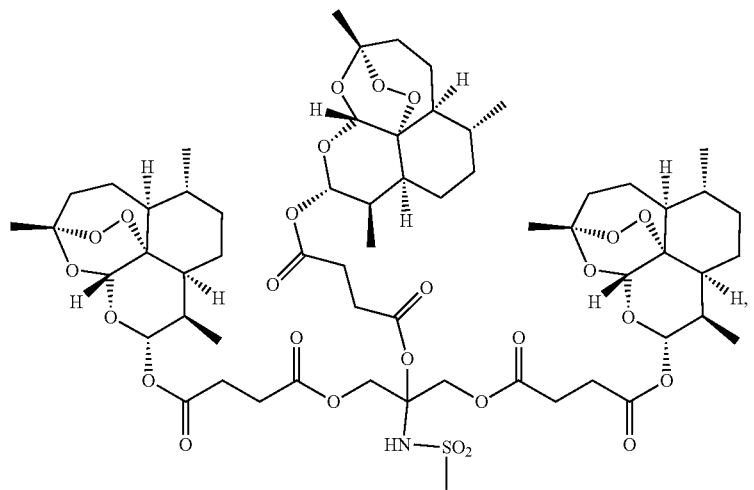
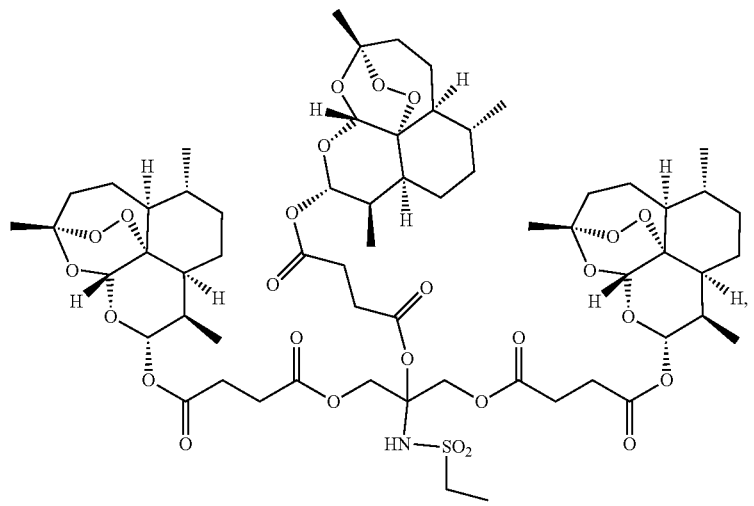

-continued
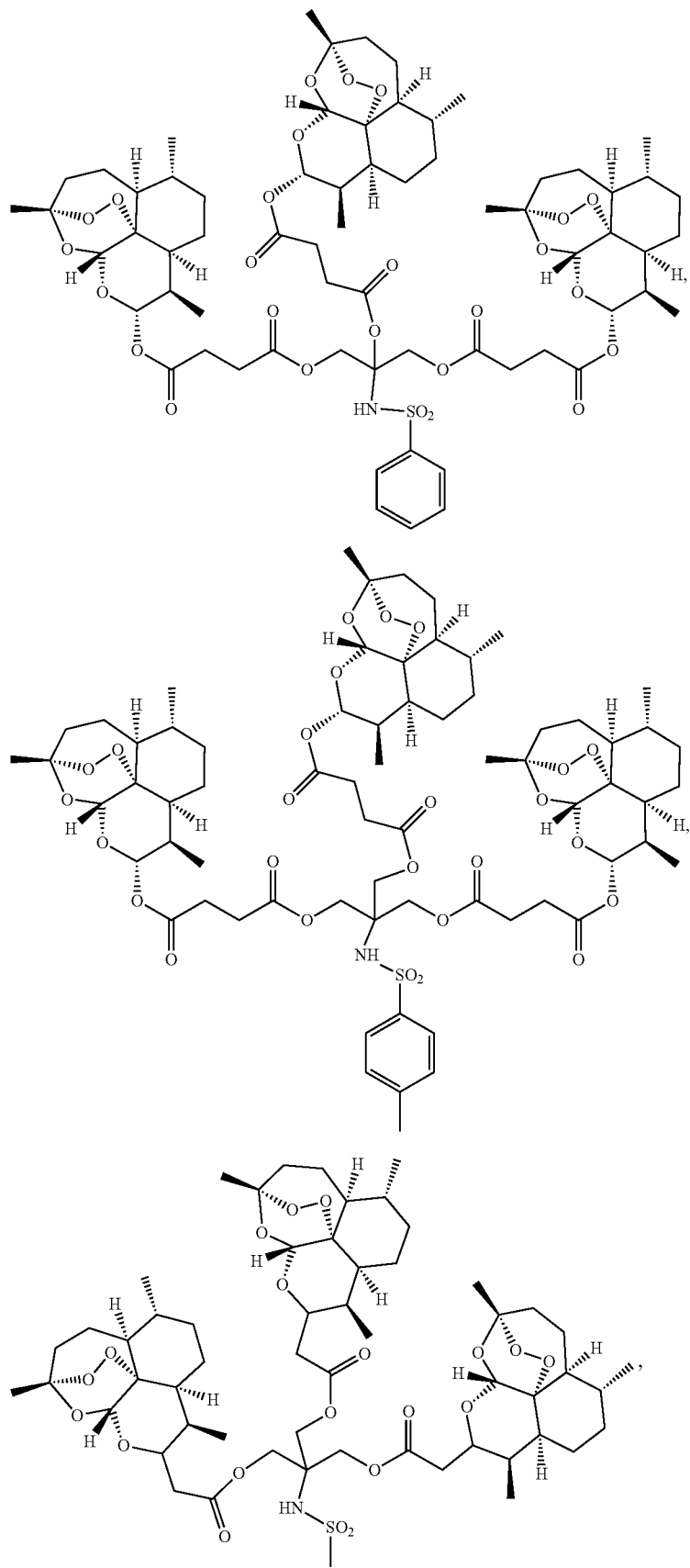

-continued
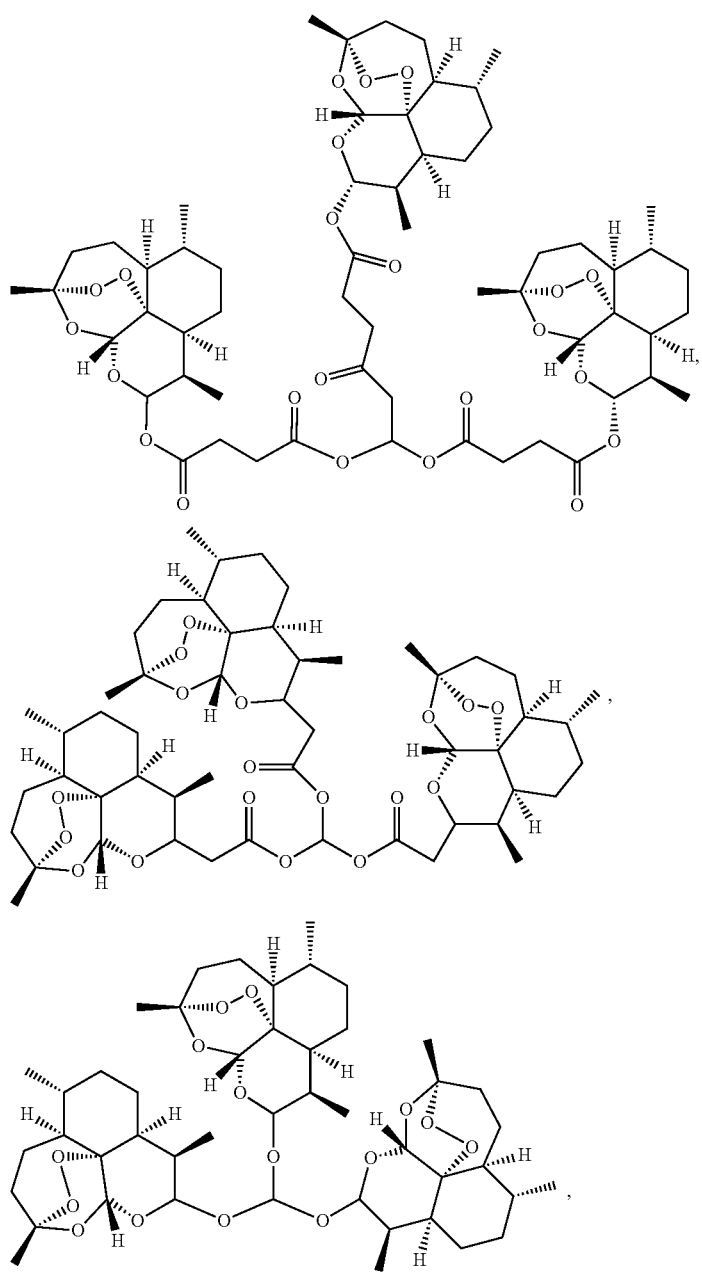
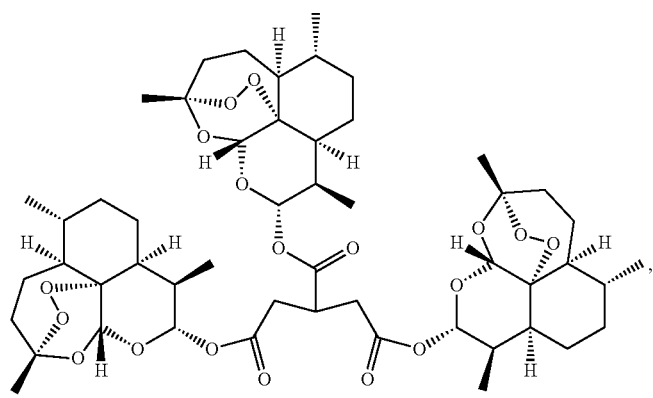
14

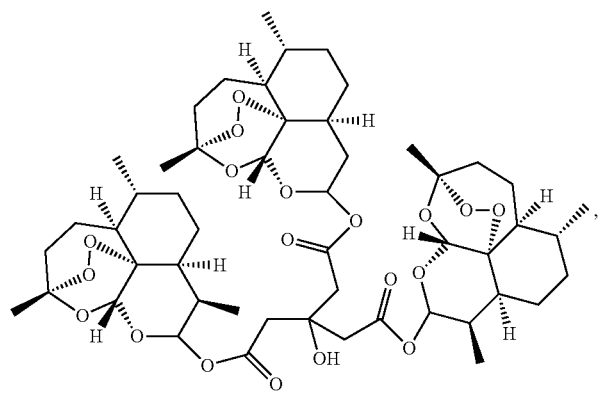
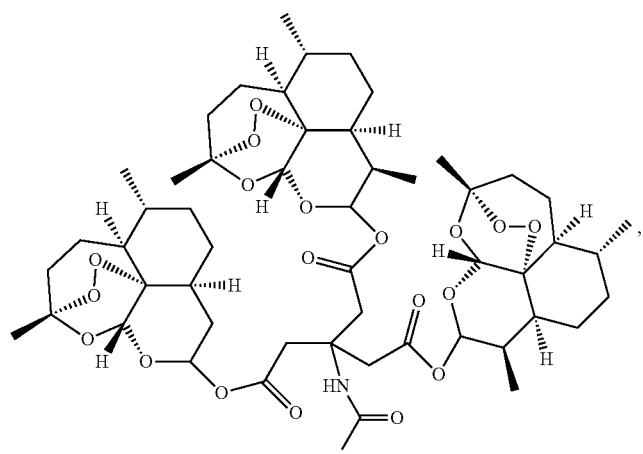
3. A compound, or a pharmaceutically acceptable salt thereof, wherein the compound is selected from:
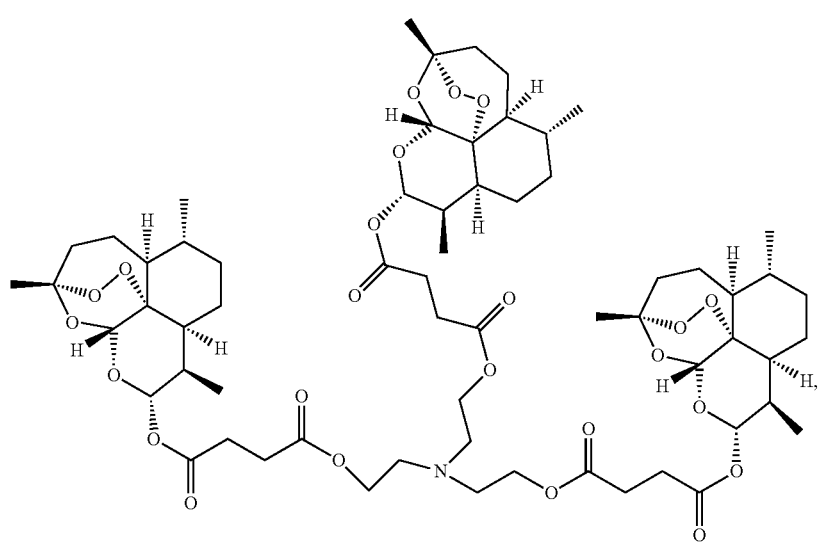

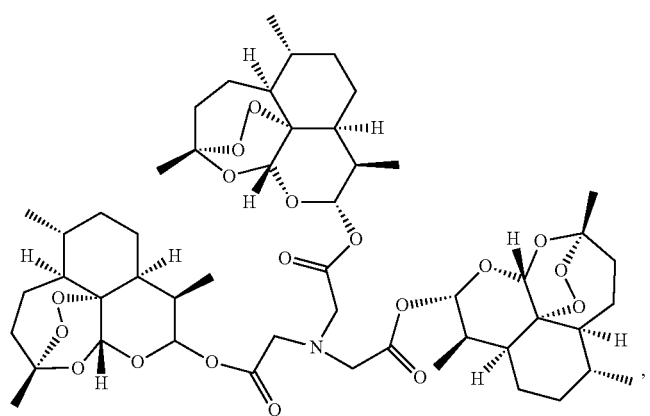
2
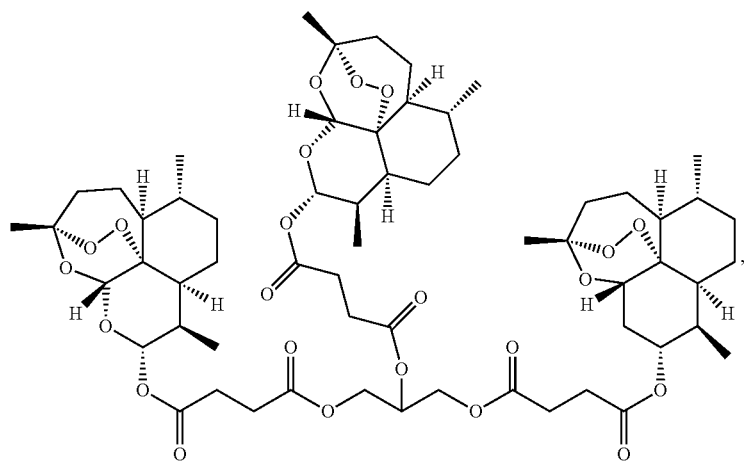
3
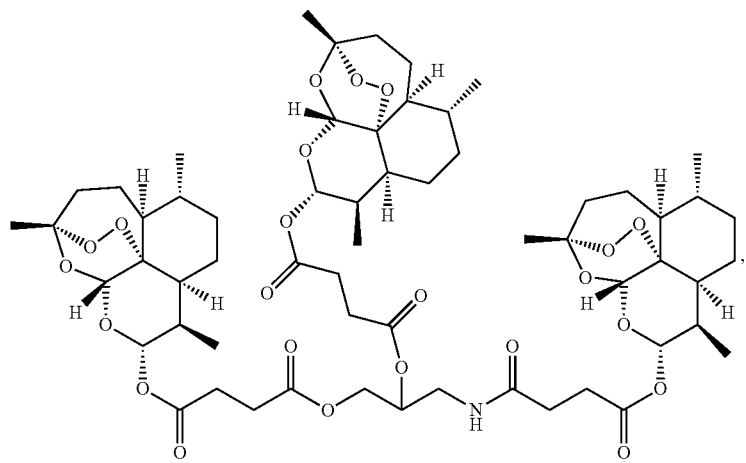

4
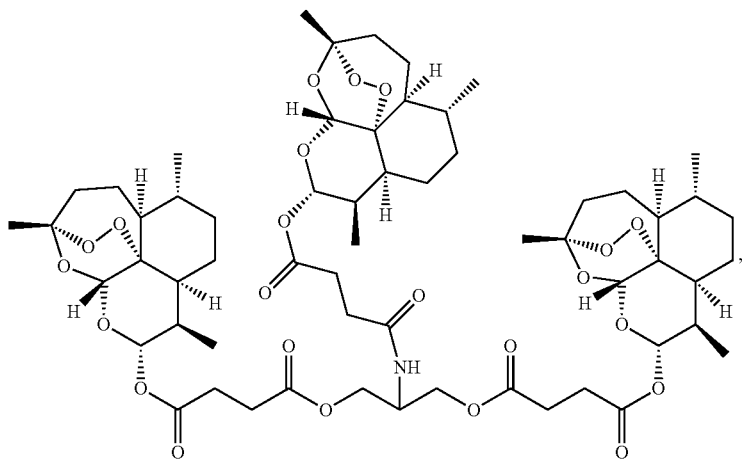
5
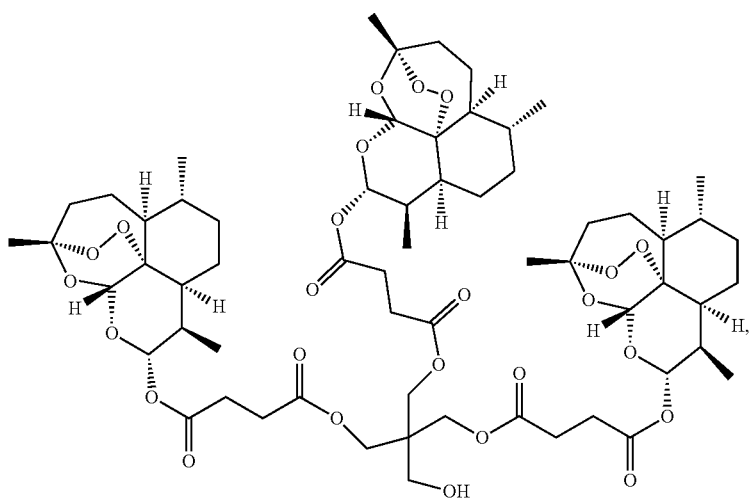
6
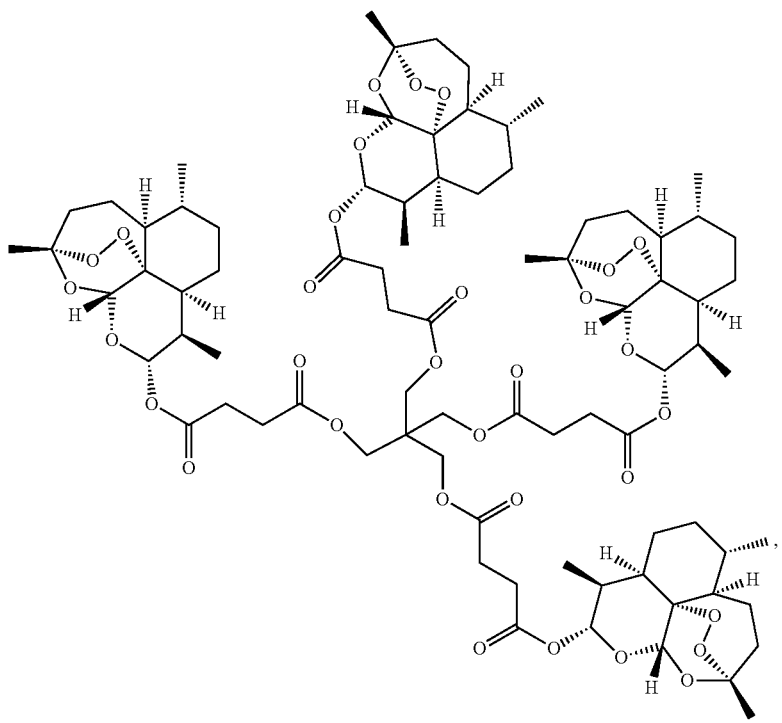

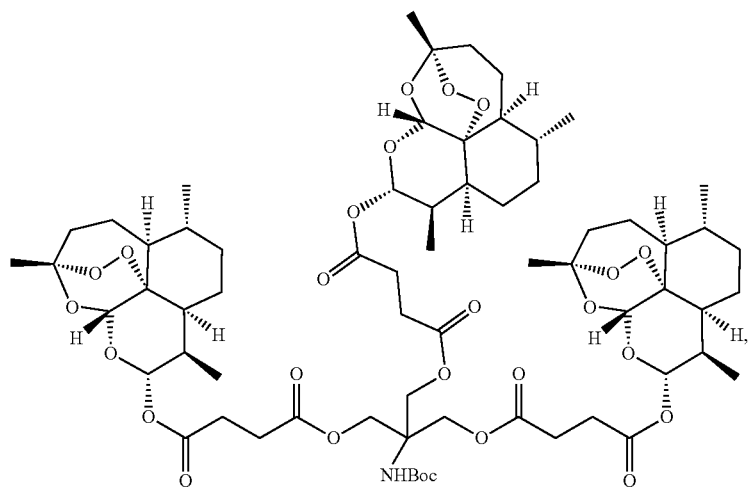
7
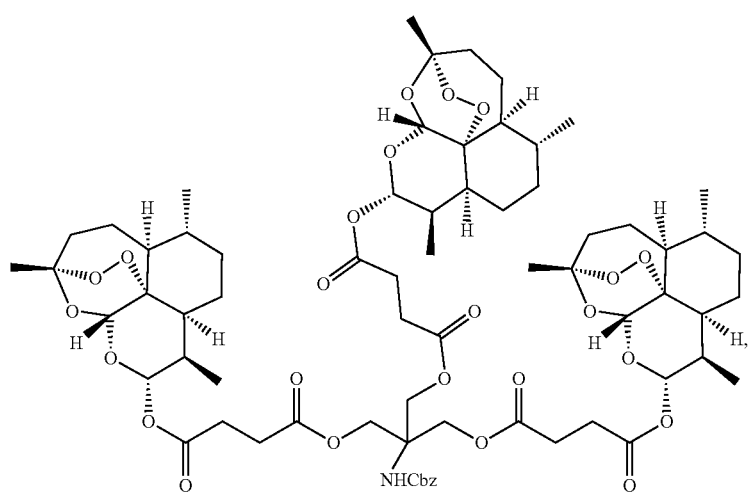
8
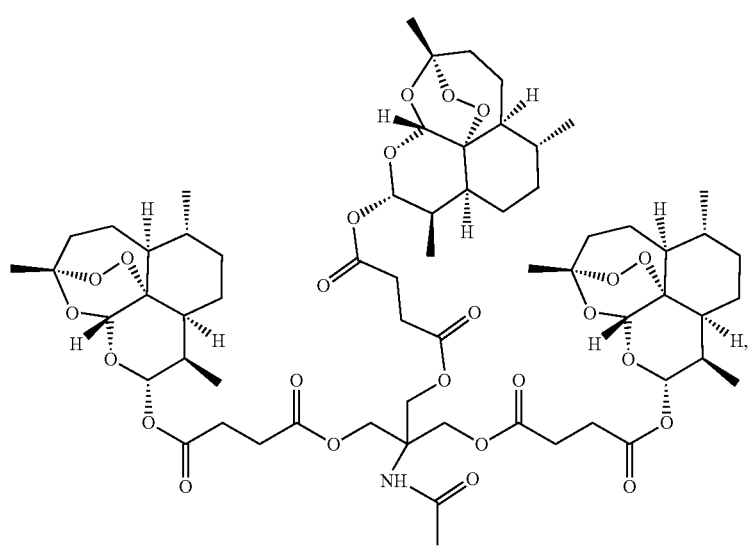
9

-continued
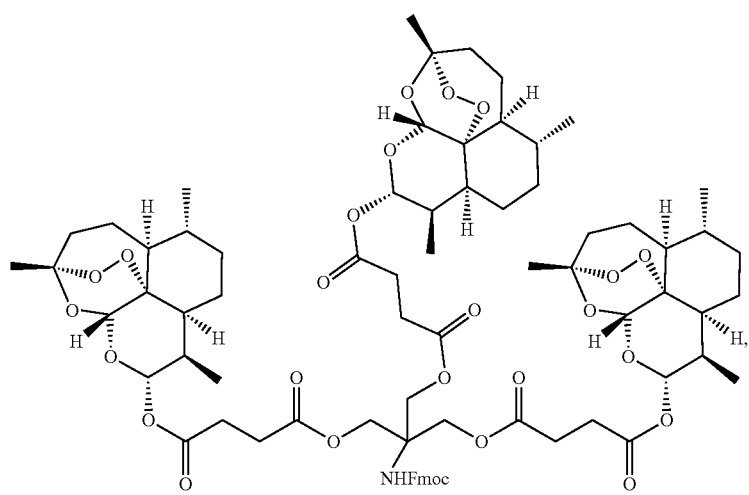
10
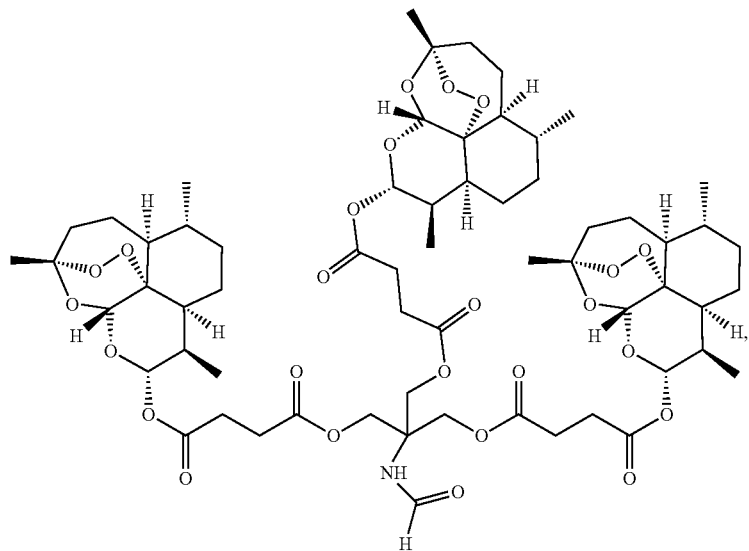
11
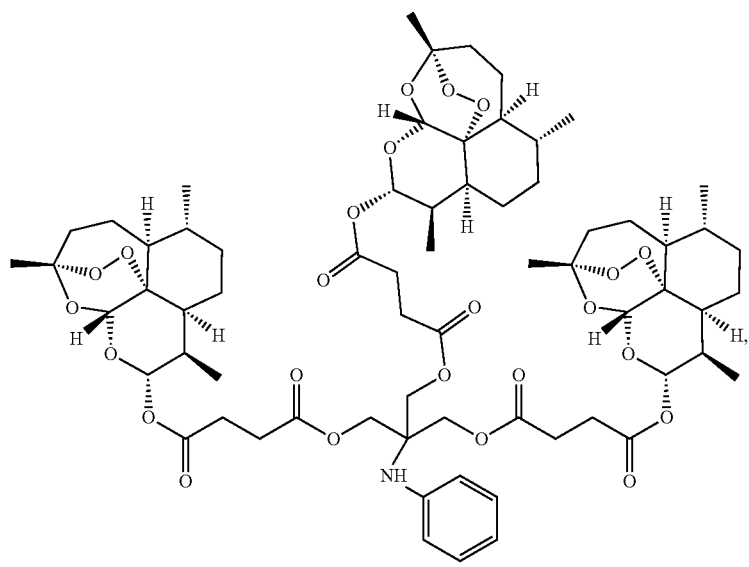

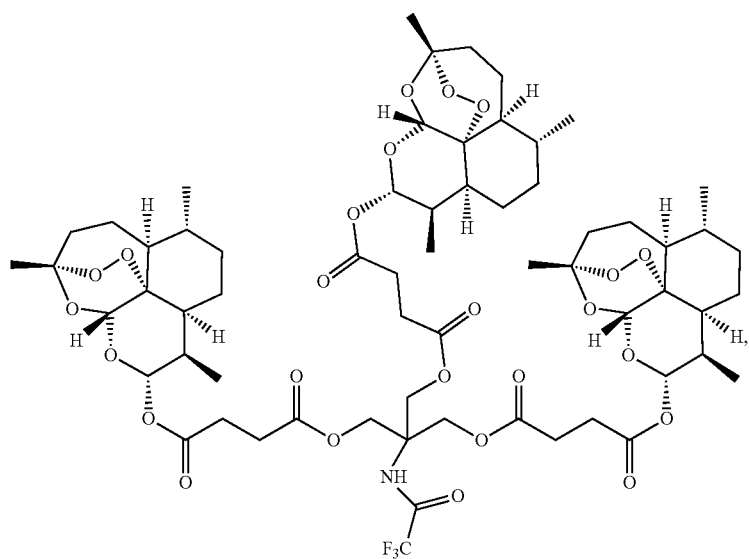
12
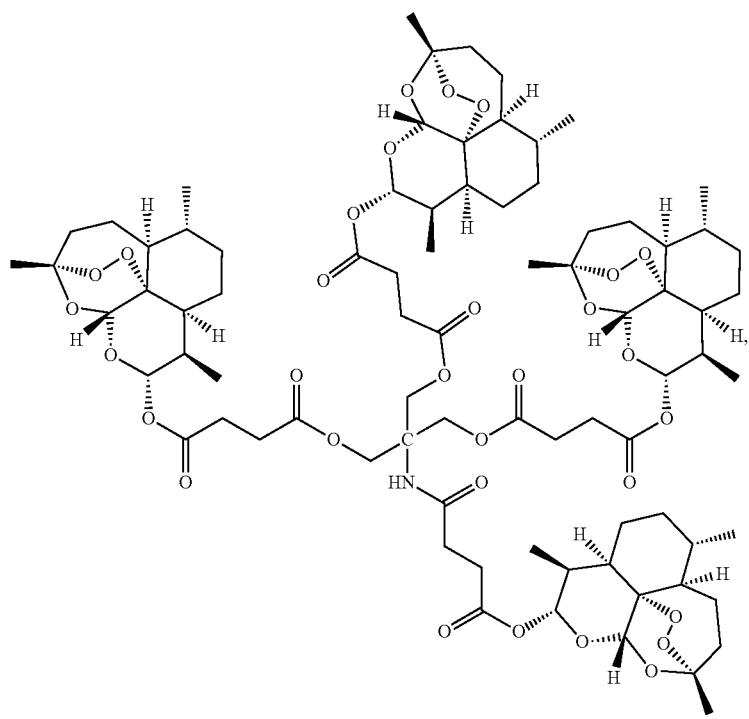
13
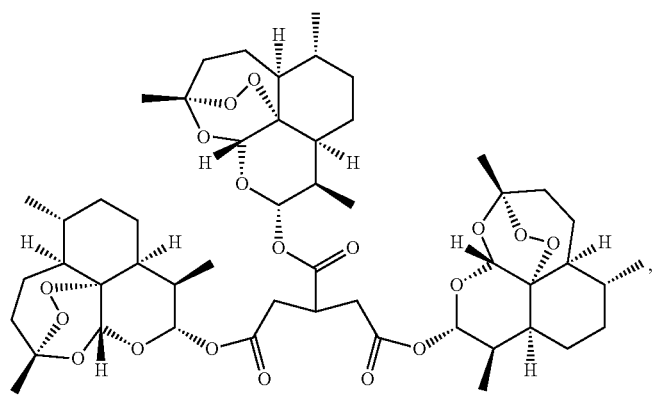
14

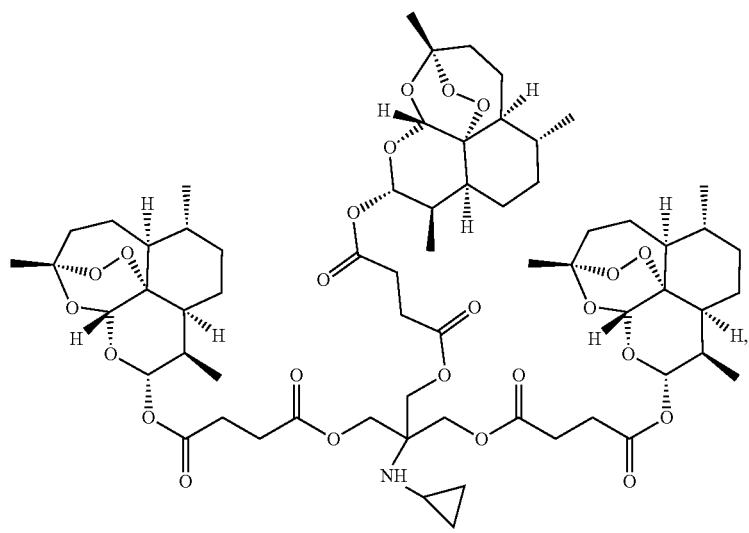
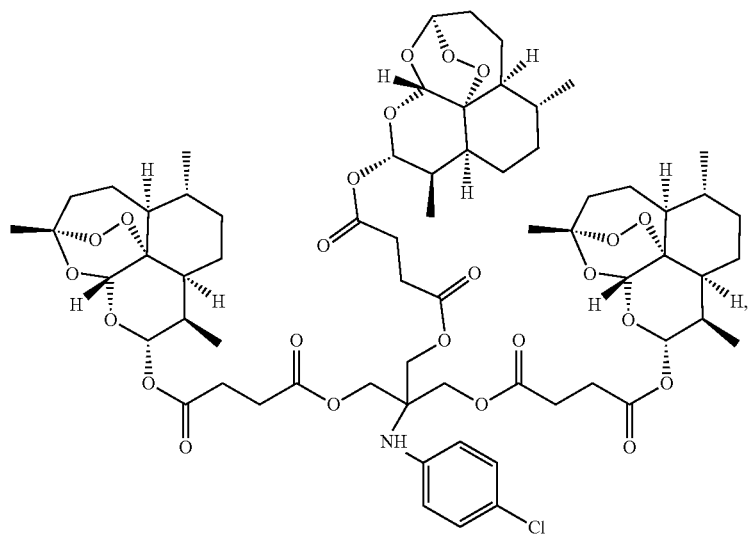
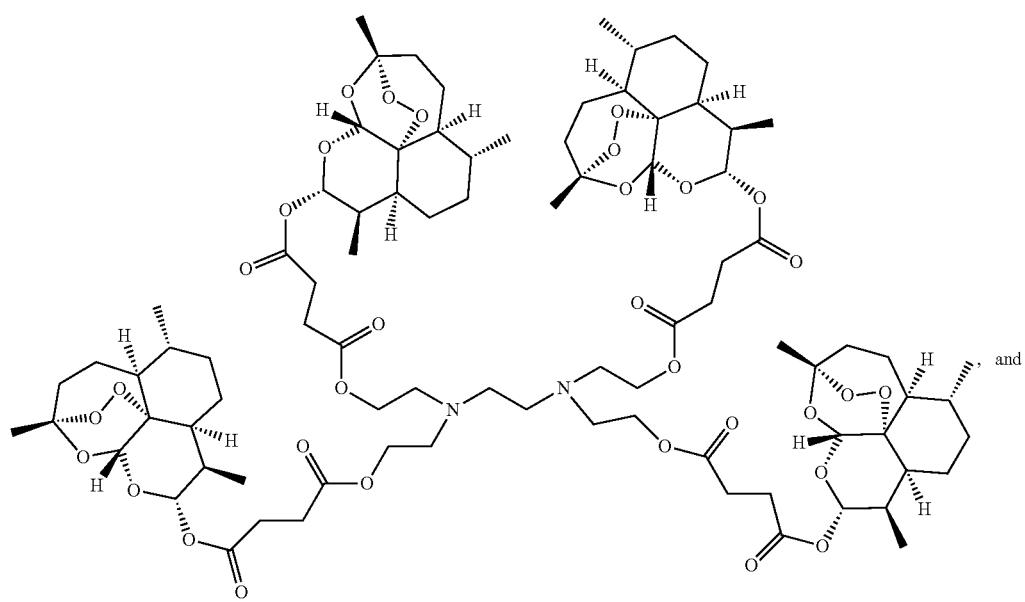

16
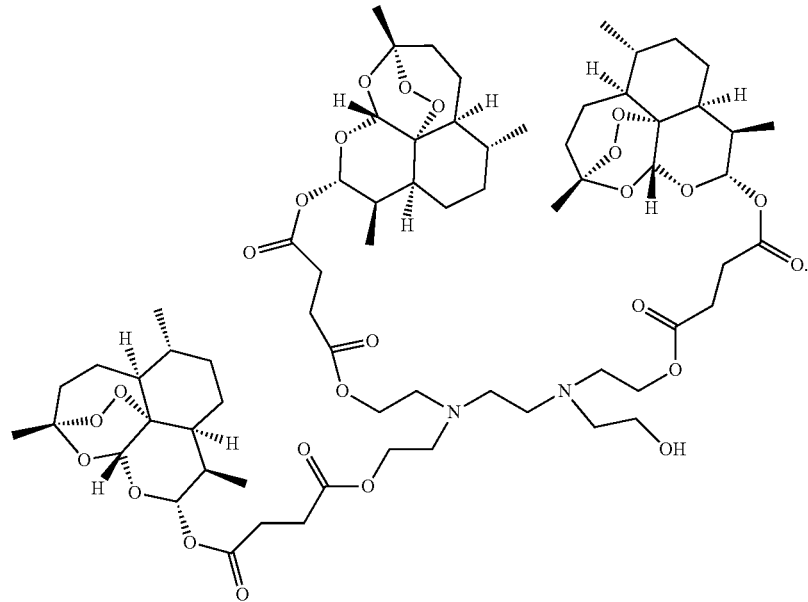
4. The compound of claim 1, or a pharmaceutically acceptable salt thereof, wherein the compound is selected from:
3
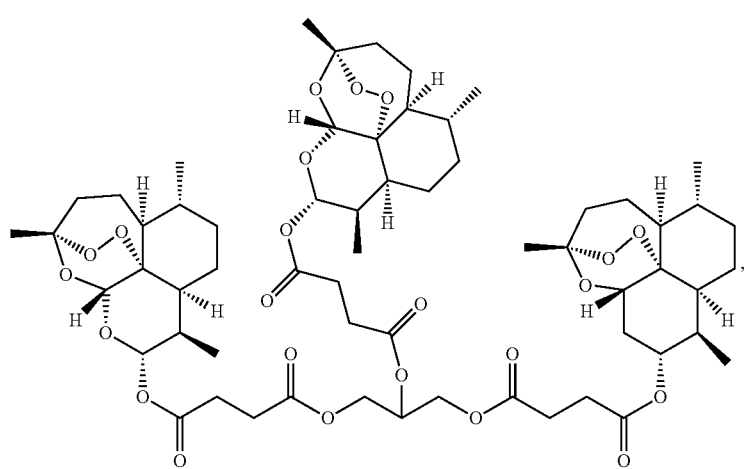

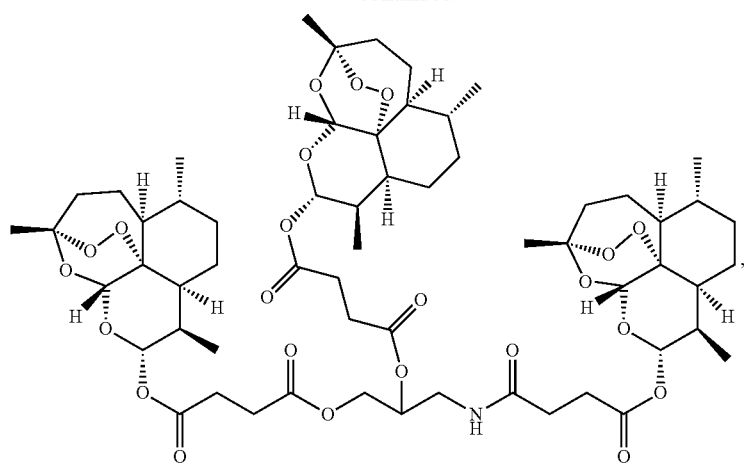
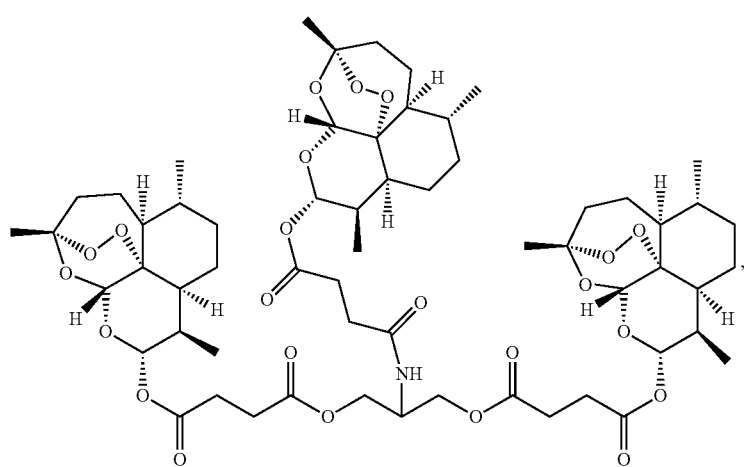
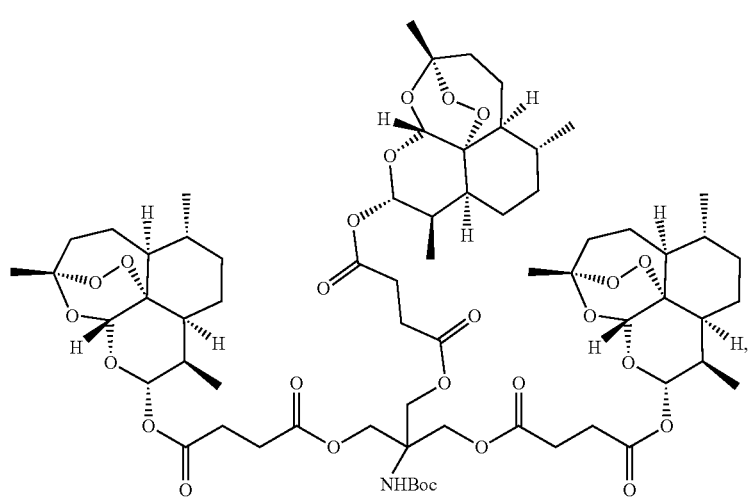

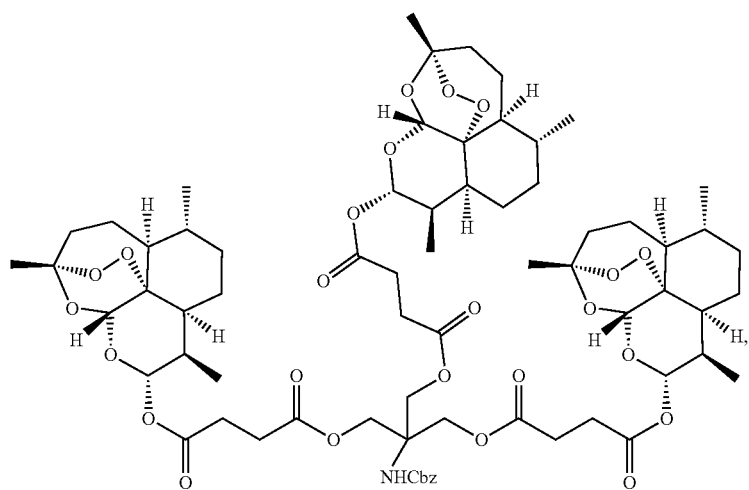
8
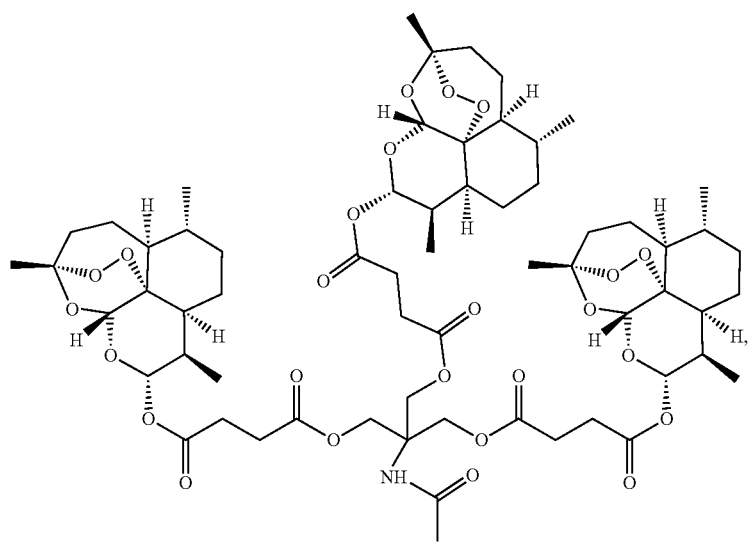
9
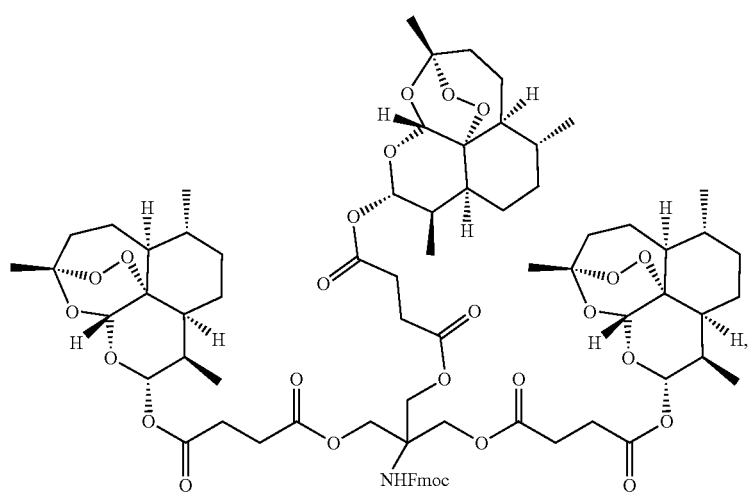
10

-continued
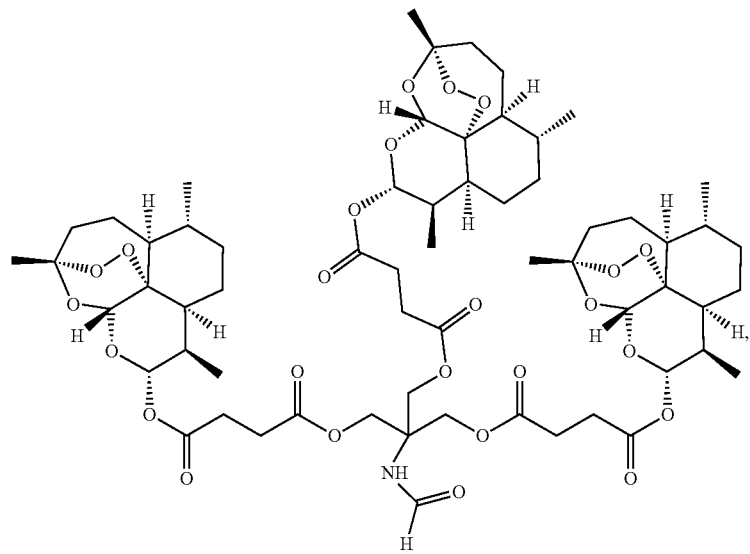
11
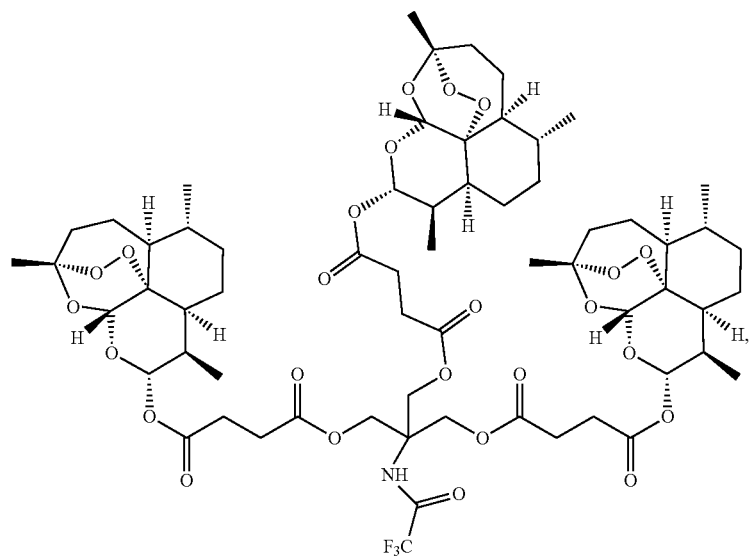
12

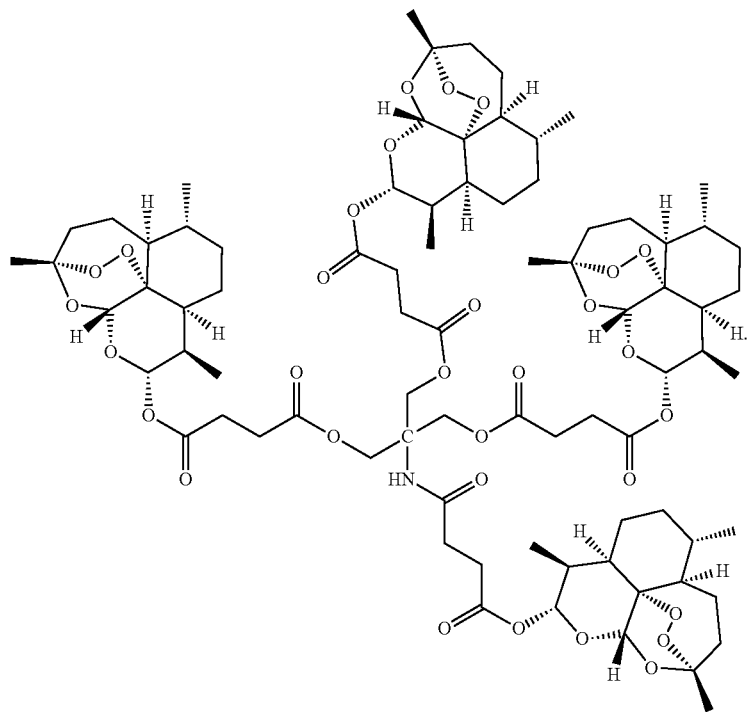
13
5. The compound of claim 1, or a pharmaceutically acceptable salt thereof, wherein the compound is selected from:
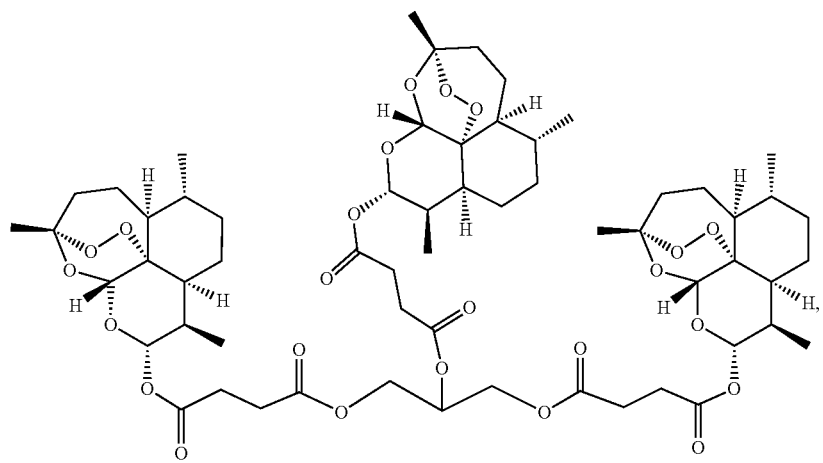
3

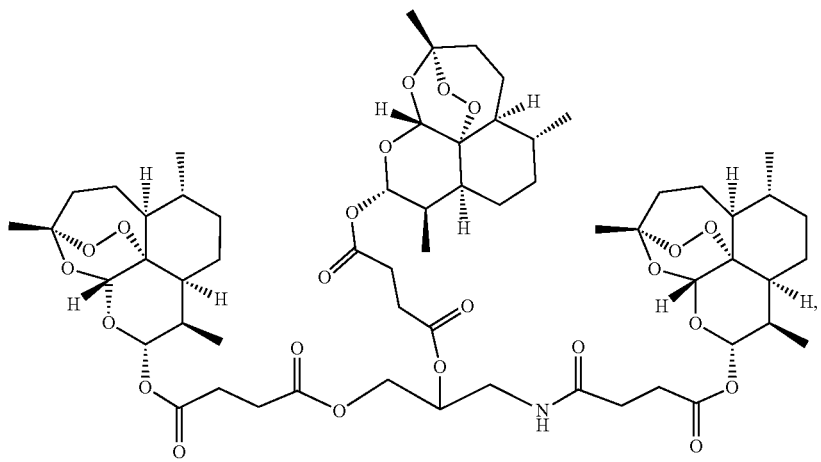
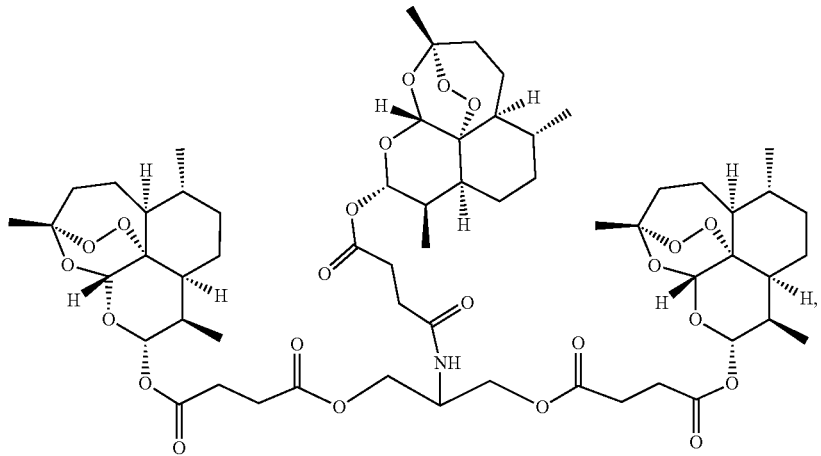
6. The compound of claim 1, or a pharmaceutically acceptable salt thereof, wherein the compound is selected from:
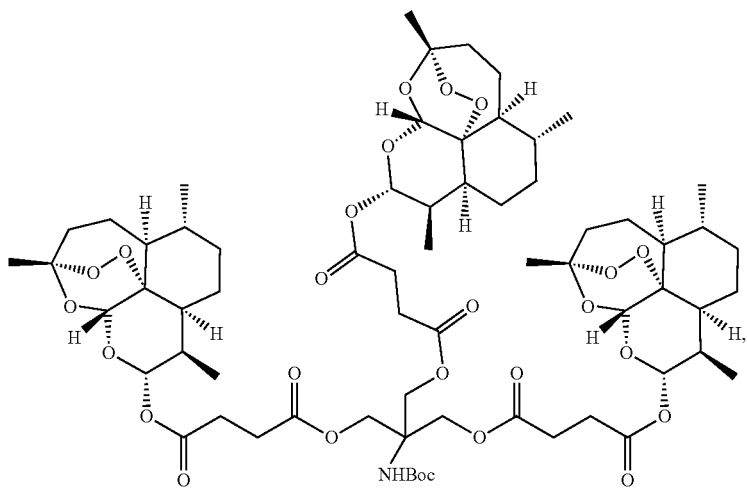

8
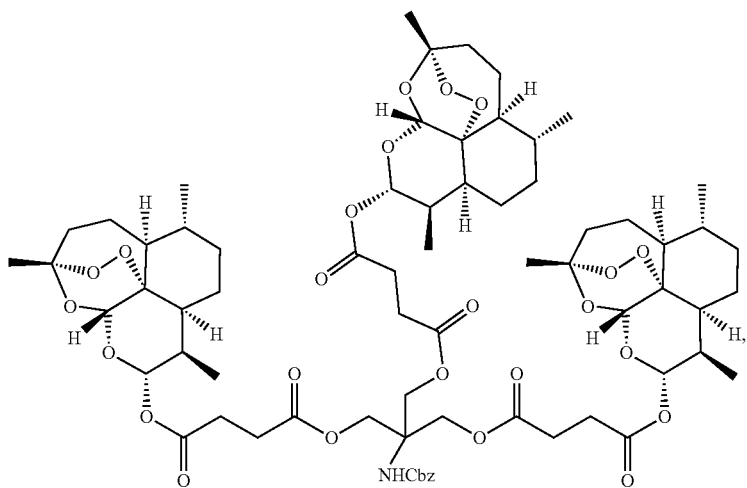
9
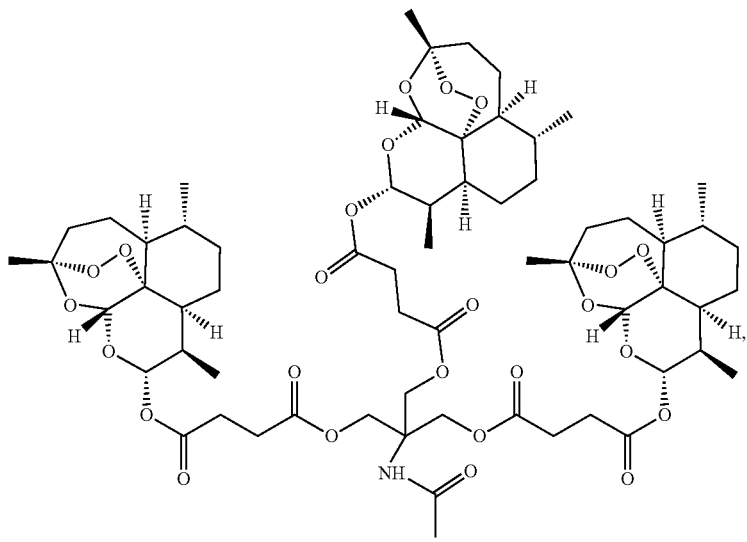
10
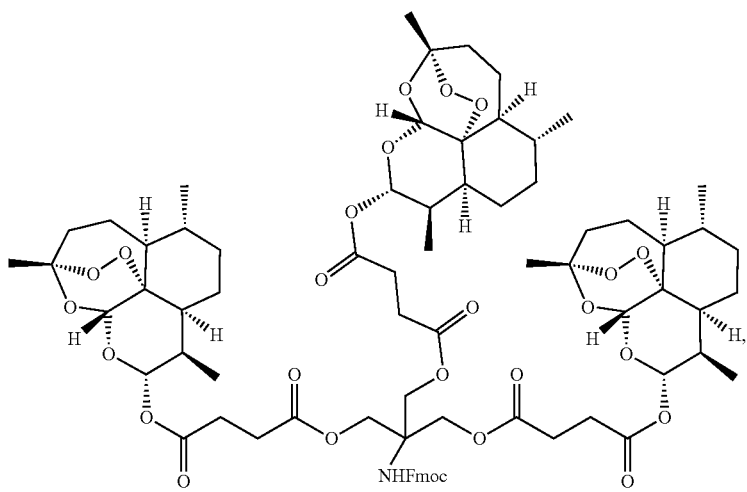

-continued
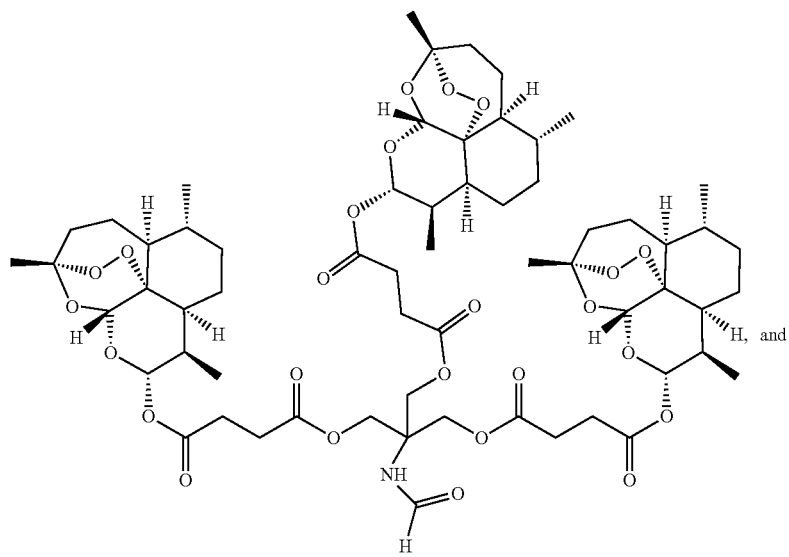
11
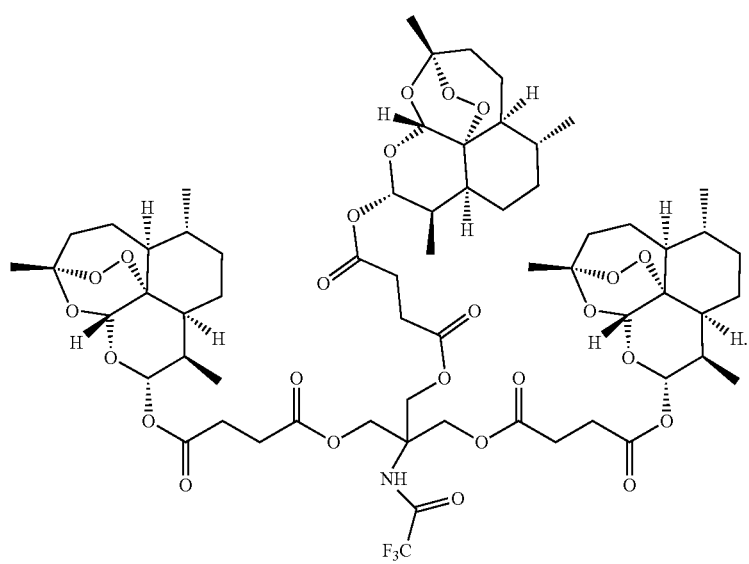
12

7. The compound of claim 2, or a pharmaceutically acceptable salt thereof, wherein the compound is selected from:
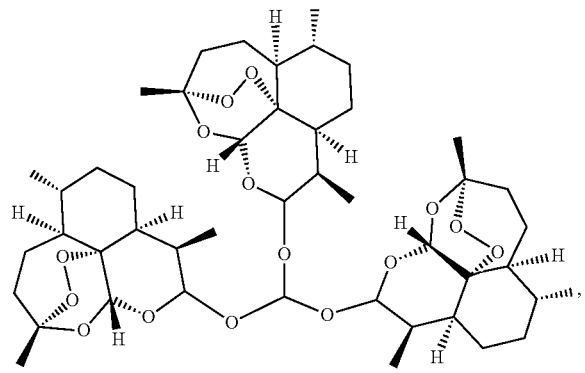
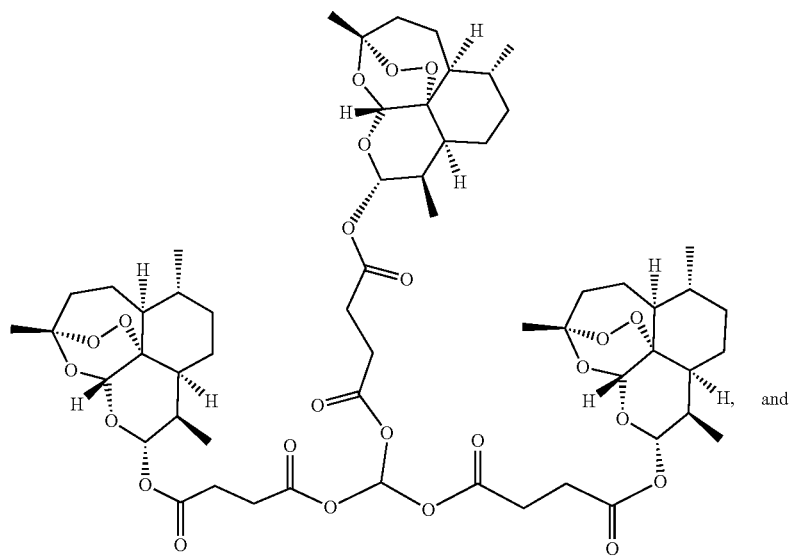
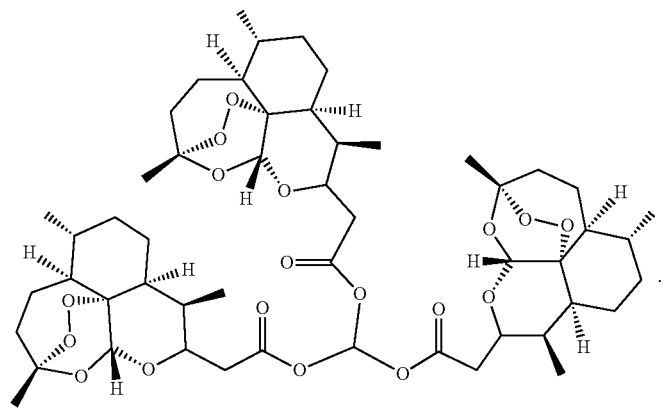

8. The compound of claim 1, or a pharmaceutically acceptable salt thereof, wherein the compound is selected from:
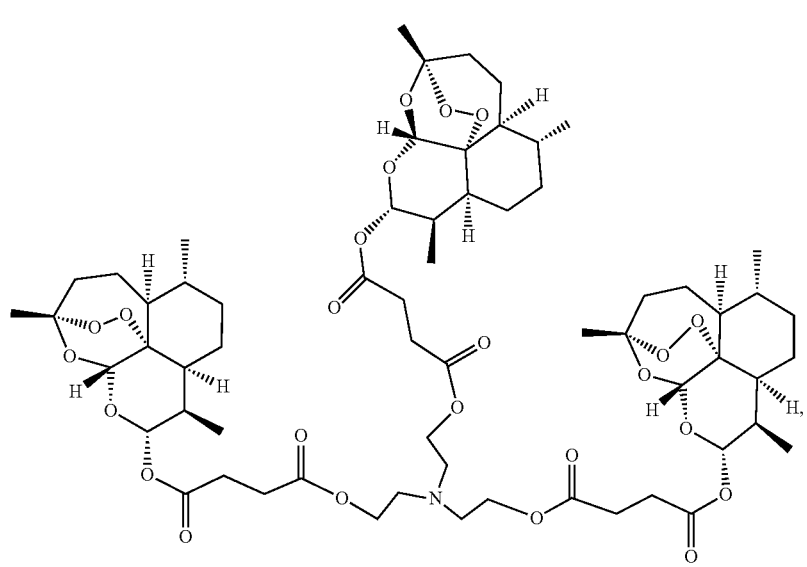
1
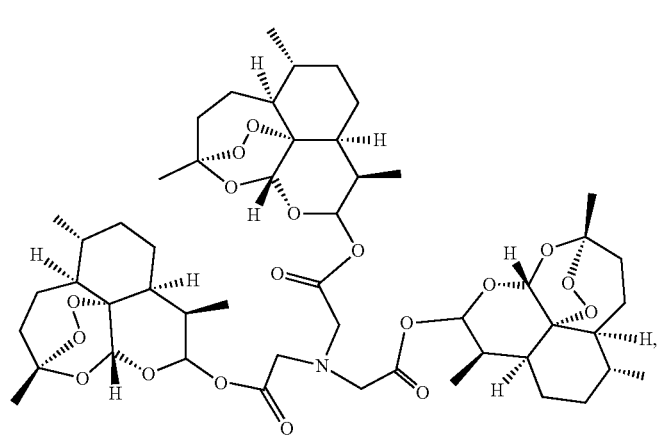
2
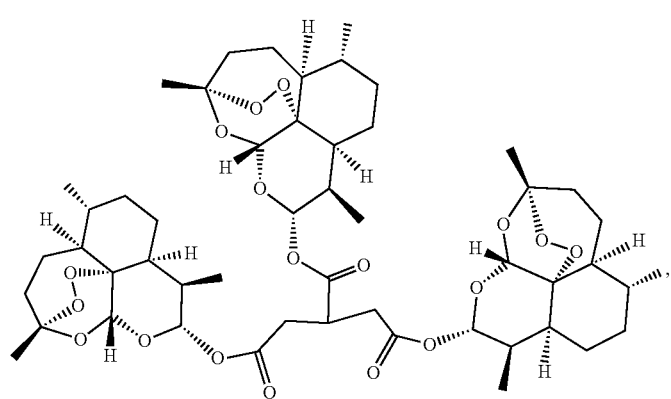
14

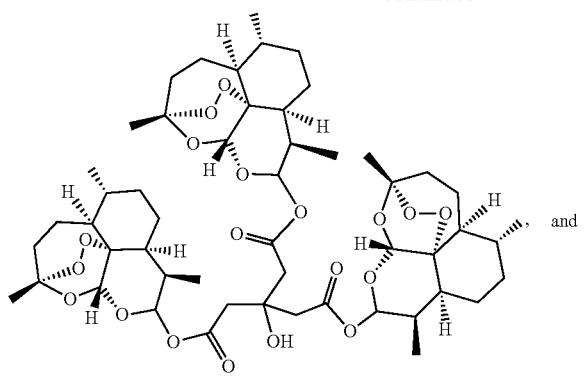
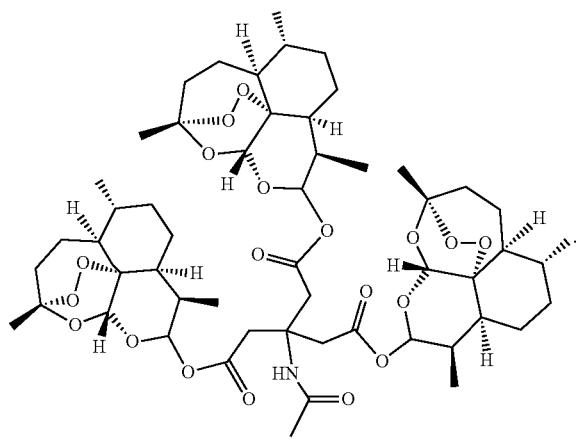
9. The compound of claim 1, or a pharmaceutically acceptable salt thereof, wherein the compound is selected from:
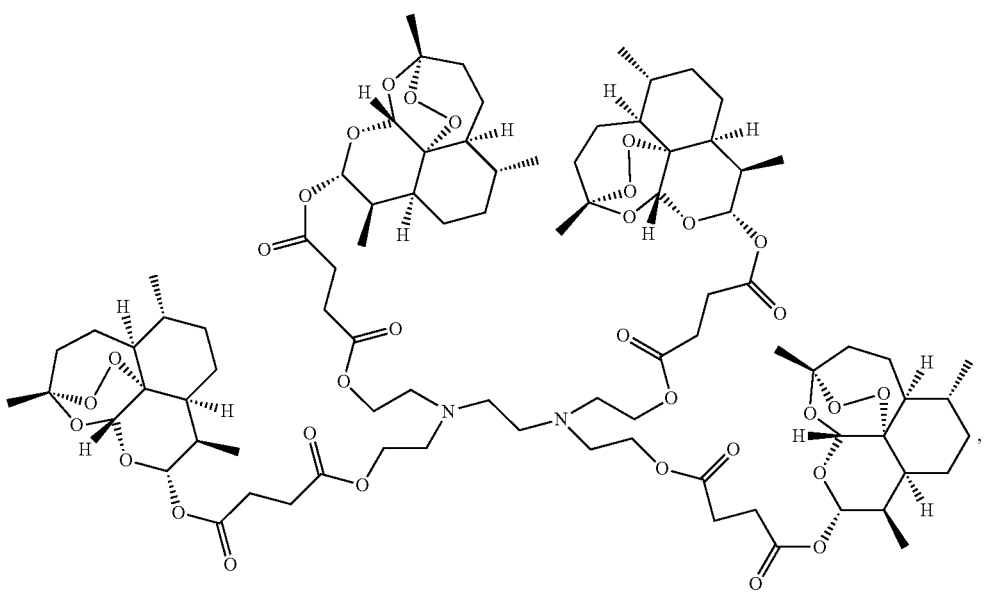

-continued
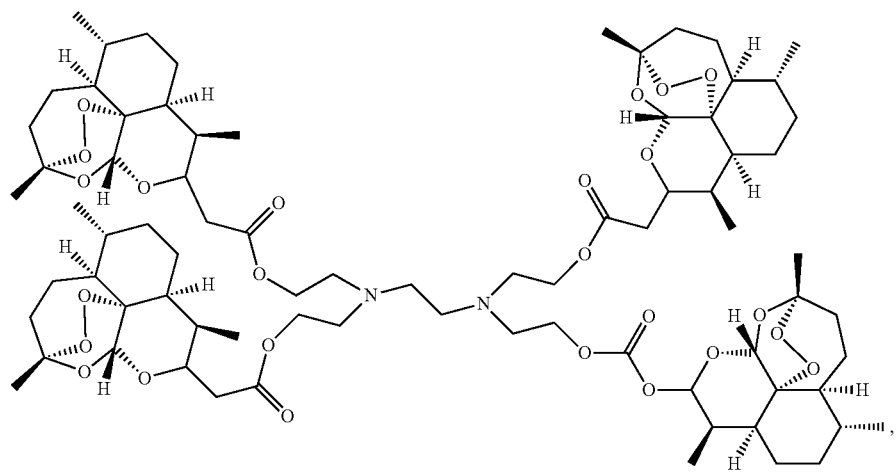
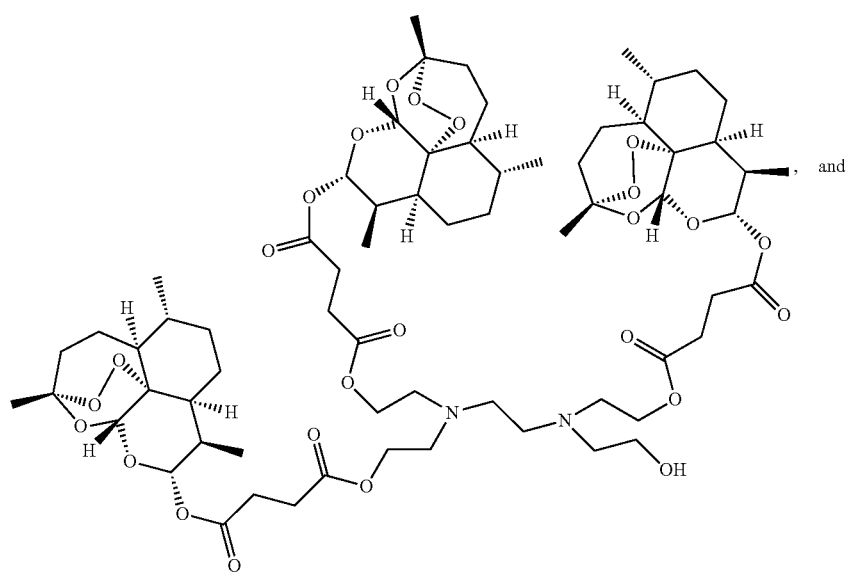
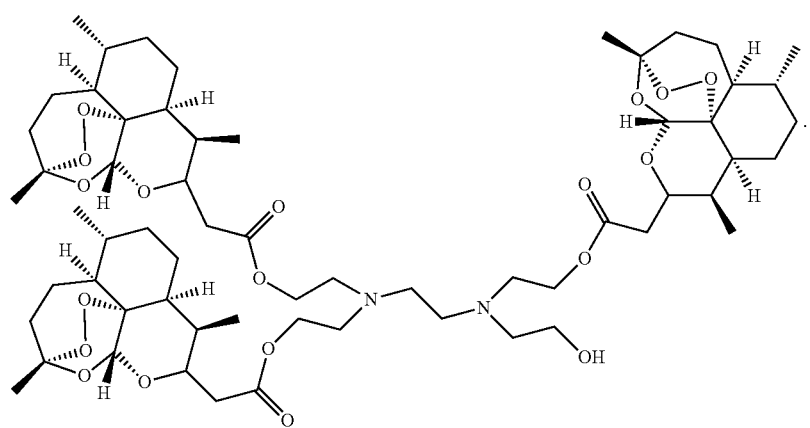

10. The compound of claim 1, or a pharmaceutically acceptable salt thereof, wherein A is carbon; Y is selected from —CH$_2$O—, or O; and R is selected from hydrogen, —CH$_2$OH, —CH$_2$OC(=O)CH$_2$CH$_2$COOH, —CH$_2$-Art1, or —CH$_2$O-Art1.

11. The compound of claim 1, or a pharmaceutically acceptable salt thereof, wherein R is selected NHR$^1$, —NR$^2$C(O)R$^1$, or —NR$^2$C(O)OR$^1$.

12. The compound of claim 1, or a pharmaceutically acceptable salt thereof, wherein A is nitrogen, or

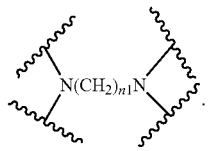

13. A pharmaceutical composition comprising the compound of claim 1 and one or more pharmaceutically acceptable excipients.

14. A method for treating cancer in a subject in need of treatment thereof, the method comprising administering to the subject a therapeutically effective amount of a compound of claim 1.

15. The method of claim 14, wherein the cancer is selected from leukemia, lung cancer, colorectal cancer, central nervous system cancer, melanoma cancer, ovarian cancer, cervical cancer, endometrial cancer, sarcoma, renal cancer, prostate cancer, breast cancer, and pancreatic cancer, nasopharyngeal carcinoma, esophageal cancer, oral cancer, and liver cancer.

16. A method of treating disease or disorders associated with parasitic infection in a subject in need of treatment thereof, the method comprising administering to the subject a pharmaceutically effective amount of the compound of claim 1.

17. The method of claim 16, wherein the parasitic infection is selected from malarial infections, *Schistosoma japonicum* infections, and toxoplasma infections.

18. A method for treating virus infections in a subject in need of treatment, thereof the method comprising administering to the subject a therapeutically effective amount of a compound of claim 1.

19. The method of claim 18, wherein the viruses are herpes simplex virus, cytomegalovirus, human papillomavirus.

* * * * *

UNITED STATES PATENT AND TRADEMARK OFFICE
CERTIFICATE OF CORRECTION

PATENT NO. : 11,358,970 B2  
APPLICATION NO. : 16/755562  
DATED : June 14, 2022  
INVENTOR(S) : Zhao et al.

Page 1 of 1

It is certified that error appears in the above-identified patent and that said Letters Patent is hereby corrected as shown below:

In the Claims

Column 56, Lines 15 to 25, " 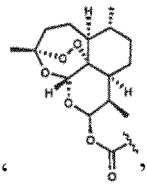 " should be changed to 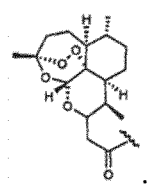 .

Column 93, the first structure, " 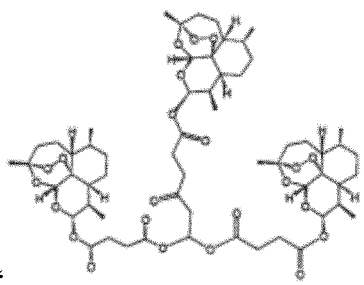 " should be changed to

Signed and Sealed this  
Twenty-first Day of November, 2023

Katherine Kelly Vidal  
*Director of the United States Patent and Trademark Office*